United States Patent
Ohtsuka et al.

(10) Patent No.: US 6,313,150 B1
(45) Date of Patent: Nov. 6, 2001

(54) α-SUBSTITUTED PHENYLACETIC ACID DERIVATIVE, ITS PRODUCTION AND AGRICULTURAL FUNGICIDE CONTAINING IT

(75) Inventors: Toshikazu Ohtsuka; Takami Murashi; Shinji Suzuki; Michio Masuko, all of Shiga; Hideyuki Takenaka, Nabari, all of (JP)

(73) Assignee: Shionogi & Co., Ltd., Osaka (JP)

( * ) Notice: Subject to any disclaimer, the term of this patent is extended or adjusted under 35 U.S.C. 154(b) by 0 days.

(21) Appl. No.: 09/590,293

(22) Filed: Jun. 9, 2000

Related U.S. Application Data

(62) Division of application No. 09/175,440, filed on Oct. 20, 1998, now abandoned, which is a division of application No. 08/718,472, filed as application No. PCT/JP95/00663 on Apr. 6, 1995, now Pat. No. 5,948,819.

(30) Foreign Application Priority Data

| Apr. 6, 1994 | (JP) | 6-068432 |
| Jul. 7, 1994 | (JP) | 6-155791 |
| Nov. 4, 1994 | (JP) | 6-271198 |
| Jan. 27, 1995 | (JP) | 7-011790 |

(51) Int. Cl.$^7$ .............. A61K 31/165; A61K 31/216; A61K 31/19; C07D 213/55; C07D 213/56
(52) U.S. Cl. .............. 514/345; 514/357; 546/290; 546/304
(58) Field of Search .............. 546/290, 304; 514/345, 357

(56) References Cited

U.S. PATENT DOCUMENTS 3,444,140 * 5/1969 Molindal et al. .............. 560/60
3,600,437 * 8/1971 Marshall et al. .............. 560/60
5,583,147 * 12/1996 Ko et al. .............. 514/336

OTHER PUBLICATIONS

Ito et al. JP 61010563, Jan. 18, 1986, CA 104: 168491, 1986. CAPLUS abstract. (1986).*

* cited by examiner

*Primary Examiner*—Mukund J. Shah
*Assistant Examiner*—Venkataraman Balasubramanian
(74) *Attorney, Agent, or Firm*—Foley & Lardner

(57) ABSTRACT

An α-substituted phenylacetic acid derivative useful as an agricultural fungicide, represented by general formula (I), or a salt thereof, a process for producing the same, an intermediate for the production thereof, and an agricultural fungicide containing the same as the active ingredient, wherein $R^1$ represents halogen, alkyl, OH, alkylthio, alkylsulfinyl, alkylsulfonyl, amino or nitro; Q represents aryl, heterocycle, mono- or disubstituted methyleneamino, (substituted amino-)methyl, alkyl, alkenyl, alkynyl, substituted carbonyl or substituted sulfonyl; X represents hydrogen, halogen, alkyl or OH; Y represents OH, alkylthio or amino; Z represents oxygen or sulfur; M represents oxygen, S(O)i (i being 0, 1 or 2), $NR^2$ ($R^2$ being hydrogen, alkyl or acyl) or a single bond; and n represents 0, 1 or 2.

(I)

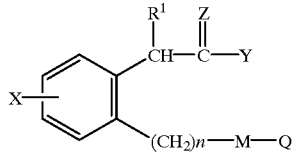

20 Claims, No Drawings

α-SUBSTITUTED PHENYLACETIC ACID DERIVATIVE, ITS PRODUCTION AND AGRICULTURAL FUNGICIDE CONTAINING IT

This application is a divisional of application Ser. No. 09/175,440 filed Oct. 20, 1998 now abandoned; which is a divisional of Ser. No. 08/718,472 filed Oct. 7, 1996, now U.S. Pat. No. 5,948,819, which is the U.S. national stage of PCT/JP95/006663, filed Apr. 6, 1995.

TECHNICAL FIELD

The present invention relates to a novel α-substituted phenylacetic acid derivative, a process for producing it, and an agricultural fungicide containing it as an active ingredient.

BACKGROUND OF THE INVENTION

Certain kinds of α-substituted phenyl acetic acid ester derivatives have been disclosed in JP-A 60-54949 and DE2742065. However, each of these compounds has a substituent at the 3-position of the phenyl group, and no compounds having a substituent at the 2-position have been disclosed. JP-A 3-17052 and JP-A 3-157350 also disclose α-substituted phenylacetic acid ester derivatives. However, they only disclose 2-hydroxy-2-phenylacetic acid or its acetic acid ester as an intermediate or insecticide, and do not disclose its fungicidal activity at all.

JP-A 4-288045, JP-A 4-261147, WO93/15046, EP-A-498396, JP-A 3-169842, EP-A-532022, JP-A 7-17930, and EP-A-619301 also disclose related compounds.

The present invention is to provide a novel compound having potent fungicidal activity, a process for producing it, and an agricultural fungicide containing it as an active ingredient.

DISCLOSURE OF THE INVENTION

Under these circumstances, the present inventors have intensively studied to obtain compounds having potent fungicidal activity. As a result, it has been found that a novel α-substituted phenylacetic acid derivative having a substituent at the 2-position in the phenyl group has potent fungicidal activity. Thus, the present invention has been completed.

The present invention provides:

1. A compound of the formula (I):

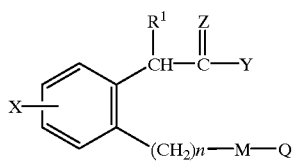

(I)

wherein $R^1$ is a halogen atom, optionally substituted alkyl, optionally substituted hydroxyl, alkylthio, alkylsulfinyl, alkylsulfonyl, optionally substituted amino or nitro; Q is optionally substituted aryl, an optionally substituted heterocyclic group, mono- or di-substituted methyleneamino, optionally substituted (substituted imino)methyl, optionally substituted alkyl, optionally substituted alkenyl, optionally substituted alkynyl, substituted carbonyl or substituted sulfonyl; X is a hydrogen atom, halogen atom, optionally substituted alkyl or optionally substituted hydroxyl; Y is optionally substituted hydroxyl, alkylthio or optionally substituted amino, provided that, when $R^1$ is hydroxyl, Y is not alkoxy; Z is an oxygen atom or sulfur atom; M is an oxygen atom, $S(O)_i$ (in which i is 0, 1 or 2), $NR^2$ (in which $R^2$ is a hydrogen atom, alkyl or acyl) or a single bond; and n is 0, 1 or 2; or a salt thereof;

2. A compound according to the above item 1, wherein $R^1$ is a halogen atom, alkyl, haloalkyl, alkoxyalkyl, hydroxyl, alkoxy, alkenyloxy, alkynyloxy, haloalkoxy, haloalkenyloxy, haloalkynyloxy, alkoxyalkoxy, alkylcarbonyloxy, (alkylthio)carbonyloxy, alkylsulfonyloxy, arylsulfonyloxy, mono- or di-alkyl-substituted carbamoyloxy, aryloxy, alkylthio, alkylsulfinyl, alkylsulfonyl, amino optionally substituted by alkyl, nitro or tetrahydropyranyloxy, or a salt thereof;

3. A compound according to the above item 1, wherein $R^1$ is alkoxy, or a salt thereof;

4. A compound according to the above item 1, wherein $R^1$ is methoxy, or a salt thereof;

5. A compound according to the above item 1, wherein Q is a group of the formula (XX):

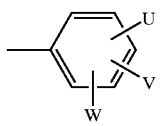

(XX)

wherein U, V and W are the same or different and are a hydrogen atom, halogen atom, optionally substituted alkyl, optionally substituted hydroxyl, alkylthio or optionally substituted amino, or a salt thereof;

6. A compound according to the above item 5, wherein U, V and W are the same or different and are a hydrogen, chlorine atom, methyl, trifluoromethyl or methoxy, or a salt thereof;

7. A compound according to the above item 1, wherein Q is pyridyl, pyrimidinyl, quinolyl, quinazolinyl, benzothiazolyl or pyrazolyl, each of which may be substituted, or a salt thereof;

8. A compound according to the above item 1, wherein Q is optionally substituted pyridyl, or a salt thereof;

9. A compound according to the above item 1, wherein Q is a group of the formula (a):

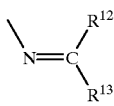

(a)

wherein $R^{12}$ and $R^{13}$ are the same or different and are a hydrogen atom, optionally substituted alkyl, acyl, alkylthio, alkylsulfinyl, alkylsulfonyl, optionally substituted amino, cycloalkyl, optionally substituted aryl or an optionally substituted heterocyclic group, or $R^{12}$ and $R^{13}$ are linked together to form a monocyclic or polycyclic ring which may contain a heteroatom, or a salt thereof;

10. A compound according to the above item 9, wherein $R^{12}$ and $R^{13}$ are the same or different and are a hydrogen atom, alkyl, haloalkyl, alkoxyalkyl, alkylcarbonyl, optionally substituted phenyl, optionally substituted naphthyl or an optionally substituted heterocyclic group, or $R^{12}$ and $R^{13}$ are linked together to form a cyclopentane ring or cyclohexane ring each of which may form a condensed ring with another ring, or a salt thereof;

11. A compound according to the above item 9, wherein $R^{12}$ is alkyl, or a salt thereof;

12. A compound according to the above item 9, wherein $R^{12}$ is methyl or ethyl, or a salt thereof;

13. A compound according to the above item 9, wherein $R^{13}$ is phenyl optionally substituted by 1 to 3 substituents selected from the group consisting of a halogen atom, optionally substituted alkyl, optionally substituted hydroxyl, alkylthio, optionally substituted amino, nitro, phenyl and cyano, or a salt thereof;

14. A compound according to the above item 9, wherein $R^{13}$ is phenyl optionally substituted by 1 to 3 substituents selected from the group consisting of a chlorine atom, methyl, trifluoromethyl and methoxy, or a salt thereof;

15. A compound according to the above item 9, wherein R13 is pyridyl, pyridazinyl, pyrazolyl, pyrimidinyl, furyl, thienyl, oxazolyl, isoxazolyl, benzothiazolyl, quinolyl, quinazolinyl, pyrazinyl, morpholino or piperazinyl, each of which may substituted, or a salt thereof;

16. A compound according to the above item 1, wherein X is a hydrogen atom, or a salt thereof;

17. A compound according to the above item 1, wherein Y is alkoxy, or a salt thereof;

18. A compound according to the above item 1, wherein Y is methoxy, or a salt thereof;

19. A compound according to the above item 1, wherein Y is monoalkylamino, or a salt thereof;

20. A compound according to the above item 1, wherein Y is monomethylamino, or a salt thereof;

21. A compound according to the above item 1, wherein Z is an oxygen atom, or a salt thereof;

22. A compound according to the above item 1, wherein M is an oxygen atom, sulfur atom or optionally substituted amino, or a salt thereof;

23. A compound according to the above item 1, wherein n is 0, or a salt thereof;

24. A compound according to the above item 1, wherein n is 1, or a salt thereof;

25. An agricultural fungicidal composition comprising a compound according to the above item 1 as an active ingredient;

26. A process for producing a compound of the formula (I-1):

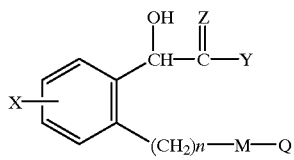

(I-1)

wherein each symbol is as defined in the above item 1, which comprises reducing a compound of the formula (II):

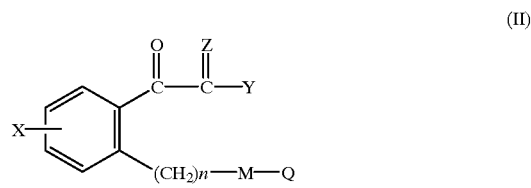

(II)

wherein each symbol is as defined in the above 1;

27. A process for producing a compound of the formula (I-2):

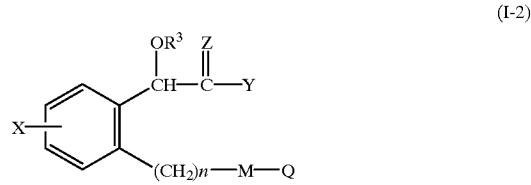

(I-2)

wherein $R^3$ is alkyl, alkenyl, alkynyl, haloalkyl, alkoxyalkyl, alkylcarbonyl, (alkylthio)carbonyl, alkylsulfonyl, arylsulfonyl, or mono- or di-alkyl-substituted carbamoyl, and the other symbols are as defined in the above item 1, which comprises reacting a compound of the formula (I-1):

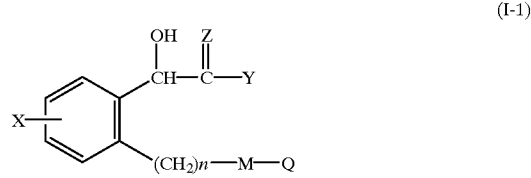

(I-1)

wherein each symbol is as defined in the above item 1, with a compound of the formula (XXII):

$R^3$—L (XXII)

wherein L is a leaving group, and the other symbols are as defined above;

28. A process for producing a compound of the formula (IV-2):

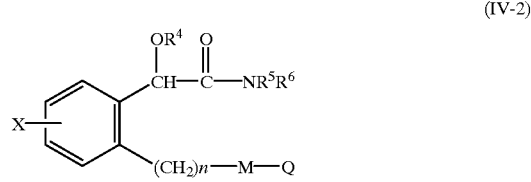

(IV-2)

wherein $R^4$ is alkyl, alkenyl, alkynyl, haloalkyl or alkoxyalkyl, $R^5$ is a hydrogen atom or alkyl, $R^6$ is a hydrogen atom, alkyl or hydroxylalkyl, and the other symbols are as defined in the above item 1, which comprises reacting a compound of the formula (IV-1):

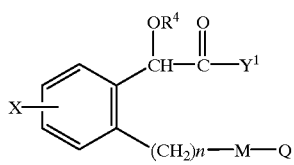

(IV-1)

wherein $Y^1$ is alkoxy or alkylthio and the other symbols are as defined above, with an amine;

29. A process for producing a compound of the formula (I-5):

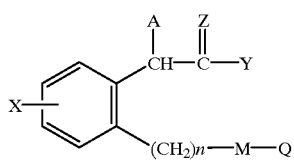

(I-5)

wherein A is a halogen atom, and the other symbols are as defined in the above item 1, which comprises halogenating a compound of the formula (I-1):

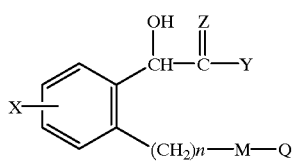

(I-1)

wherein each symbol is as defined in the above item 1;

30. A process for producing a compound of the formula (I-6):

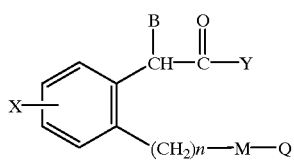

(I-6)

wherein B is alkoxy, alkenyloxy, alkynyloxy, haloalkoxy, alkoxyalkoxy, alkylthio, amino optionally substituted by alkyl, or nitro, and the other symbols are as defined in the above item 1, which comprises reacting a compound of the formula (I-5):

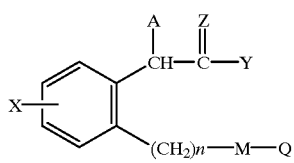

(I-5)

wherein A is a halogen atom and the other symbols are as defined in the above item 1, with a nucleophile;

31. A process for producing a compound of the formula (I):

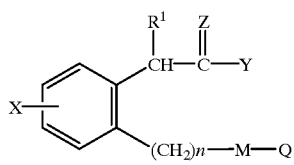

(I)

wherein each symbol is as defined in the above 1, which comprises reacting a compound of the formula (XVIII):

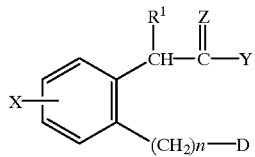

(XVIII)

wherein D is a halogen atom, and the other symbols are as defined in the above item 1, with a compound of the formula (XIX):

Q—MH  (XIX)

wherein each symbol is as defined in the above item 1;

32. A process for producing a compound of the formula (I):

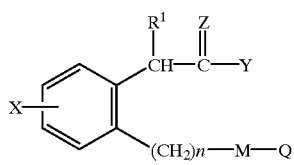

(I)

wherein each symbol is as defined in the above 1, which comprises reacting a compound of the formula (XXIII):

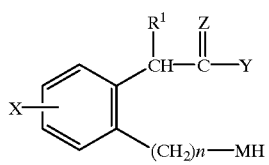

(XXIII)

wherein each symbol is as defined in the above item 1, with a compound of the formula (XXIV):

Q—L  (XXIV)

wherein L is a leaving group, and Q is as defined in the above item 1;

33. A compound of the formula (XXXIX):

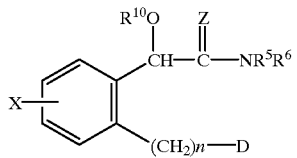
(XXXIX)

wherein $R^5$ is a hydrogen atom or alkyl, $R^6$ is a hydrogen atom, alkyl or hydroxylalkyl, $R^{10}$ is optionally substituted alkyl, optionally substituted alkenyl or optionally substituted alkynyl, D is a halogen atom, and the other symbols are as defined in the above item 1, or a salt thereof;

34. A compound of the formula (XXXII):

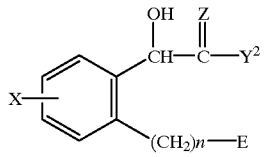
(XXXII)

wherein $Y^2$ is alkoxy, E is a protected hydroxyl, and the other symbols are as defined in the above item 1, or a salt thereof;

35. A compound according to the above item 34, wherein E is tetrahydropyranyloxy or 1-ethoxyethoxy, or a salt thereof;

36. A compound of the formula (XXXV):

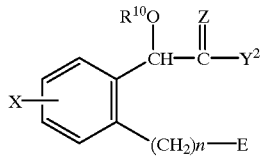
(XXXV)

wherein $R^{10}$ is optionally substituted alkyl, optionally substituted alkenyl or optionally substituted alkynyl, $Y^2$ is alkoxy, E is a protected hydroxyl, and the other symbols are as defined in the above item 1, or a salt thereof;

37. A compound according to the above item 36, wherein E is tetrahydropyranyloxy or 1-ethoxyethoxy, or a salt thereof;

38. A compound of the formula (XXXVI):

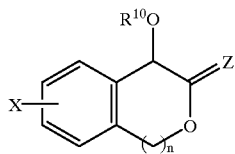
(XXXVI)

wherein $R^{10}$ is optionally substituted alkyl, optionally substituted alkenyl or optionally substituted alkynyl, and the other symbols are as defined in the above item 1, or a salt thereof;

39. A compound of the formula (XXXVII):

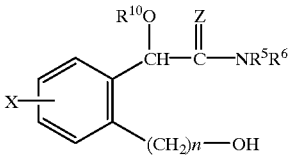
(XXXVII)

wherein $R^5$ is a hydrogen atom or alkyl, $R^6$ is a hydrogen atom, alkyl or hydroxylalkyl, $R^{10}$ is optionally substituted alkyl, optionally substituted alkenyl or optionally substituted alkynyl, and the other symbols are as defined in the above item 1, or a salt thereof; and 40. A compound according to any one of the above items 33 to 39, wherein Z is an oxygen atom, or a salt thereof.

The halogen atom represented by $R^1$ includes fluorine, chlorine, bromine and iodine.

The optionally substituted alkyl represented by $R^1$ includes, for example, alkyl having 1 to 8 carbon atoms, preferably 1 to 4 carbon atoms, such as methyl, ethyl, propyl, isopropyl, butyl, isobutyl, t-butyl, pentyl, hexyl, etc. In particular, methyl and ethyl are preferred. The substituted alkyl includes, for example, haloalkyl having as a substituent at least one halogen atom (e.g., fluorine, chlorine, bromine, iodine, preferably fluorine)(e.g., difluoromethyl, trifluoromethyl, chloromethyl, 2-bromoethyl, 2,3-dichloropropyl, etc.); alkoxyalkyl having as a substituent alkoxy having 1 to 8 carbon atoms, preferably 1 to 4 carbon atoms (e.g., methoxy, ethoxy, propoxy, butoxy, etc.)(e.g., methoxymethyl, ethoxymethyl, methoxyethyl, etc.), etc. In particular, trifluoromethyl is preferred for the haloalkyl, and methoxymethyl is preferred for the alkoxyalkyl.

The optionally substituted hydroxyl represented by $R^1$ includes, for example, hydroxyl, optionally substituted alkoxy, optionally substituted alkenyloxy, optionally substituted alkynyloxy, alkylcarbonyloxy, (alkylthio)carbonyloxy, alkylsulfonyloxy, arylsulfonyloxy, mono- or di-alkyl-substituted carbamoyloxy, aryloxy, tetrahydropyranyloxy, etc.

Examples of the optionally substituted alkoxy include alkoxy having 1 to 8 carbon atoms, preferably 1 to 4 carbon atoms, such as methoxy, ethoxy, propoxy, isopropoxy, butoxy, isobutoxy, t-butoxy, pentyloxy, hexyloxy, etc.: haloalkoxy having as a substituent at least one halogen atom (e.g., fluorine, chlorine, bromine, iodine, preferably fluorine) such as difluoromethoxy, trifluoromethoxy, chloromethoxy, etc.; alkoxyalkoxy having as a substituent alkoxy having 1 to 8 carbon atoms, preferably 1 to 4 carbon atoms (e.g., methoxy, ethoxy, propoxy, butoxy, etc.) such as methoxymethoxy, 2-methoxyethoxy, ethoxymethoxy, etc. Methoxy, ethoxy and butoxy, in particular methoxy, are preferred for the alkoxy. Difluoromethoxy is preferred for the haloalkoxy. Methoxymethoxy is preferred for the alkoxyalkoxy.

Examples of the optionally substituted alkenyloxy include alkenyloxy having 2 to 8 carbon atoms, preferably 2 to 4 carbon atoms, such as vinyloxy, allyloxy, propenyloxy, isopropenyloxy, butenyloxy, isobutenyloxy, pentenyloxy, hexenyloxy, hexadienyloxy, etc.; haloalkenyloxy having as a substituent at least one halogen atom (e.g., fluorine, chlorine, bromine, iodine) such as 3,3-dichloro-2-propenyloxy, 4,4,4-trifluoromethyl-2-butenyloxy, etc. In particular, allyloxy is preferred.

Examples of the optionally substituted alkynyloxy include alkynyloxy having 2 to 8 carbon atoms, preferably 2 to 4 carbon atoms, such as ethynyloxy, propargyloxy, butynyloxy, etc.; haloalkynyloxy having as a substituent at least one halogen atom (e.g., fluorine, chlorine, bromine, iodine) such as 3-chloro-2-propynyloxy, 4,4,4-trifluoromethyl-2-butynyloxy, etc. In particular, propargyloxy is preferred.

Examples of the alkylcarbonyloxy include alkylcarbonyloxy which contains alkyl having 1 to 8 carbon atoms, preferably 1 to 4 carbon atoms, such as acetoxy, propionyloxy, butyryloxy, etc. In particular, acetoxy is preferred.

Examples of the (alkylthio)carbonyloxy include (alkylthio)carbonyloxy which contains alkyl having 1 to 8 carbon atom, preferably 1 to 4 carbon atoms, such as (methylthio)carbonyloxy, (ethylthio)carbonyloxy, (propylthio)carbonyloxy, etc. In particular, (methylthio)carbonyloxy is preferred.

Examples of the alkylsulfonyloxy include alkylsulfonyloxy which contains alkyl having 1 to 8 carbon atom, preferably 1 to 4 carbon atom, such as methanesulfonyloxy, ethanesulfonyloxy, propanesulfonyloxy, etc. In particular, methanesulfonyloxy is preferred.

Examples of the arylsulfonyloxy include arylsulfonyloxy which contains aryl having 6 to 12, preferably 6 to 8 carbon atoms, such as benzenesulfonyloxy, p-toluenesulfonyloxy, etc. In particular, p-toluenesulfonyoxy is preferred.

Examples of the mono- or di-alkyl-substituted carbamoyloxy include mono- or di-alkyl-substituted carbamoyloxy which contains alkyl having 1 to 8 carbon atoms, preferably 1 to 4 carbon atoms, such as N-monomethylcarbamoyloxy, N,N-dimethylcarbamoyloxy, N-monoethylcarbamoyloxy, etc. In particular, N,N-dimethylcarbamoyloxy is preferred.

Examples of the aryloxy include aryloxy having 6 to 12, preferably 6 to 8 carbon atoms, such as phenoxy, 2-methylphenoxy, 2,5-dimethylphenoxy, etc.

Examples of the tetrahydropyranyloxy include 2-tetrahydropyranyloxy, etc.

The alkylthio represented by $R^1$ includes, for example, alkylthio having 1 to 8 carbon atoms, preferably 1 to 4 carbon atoms, such as methylthio, ethylthio, propylthio, and butylthio. In particular, methylthio is preferred.

The alkylsulfinyl represented by $R^1$ includes, for example, alkylsulfinyl having 1 to 8 carbon atoms, preferably 1 to 4 carbon atoms, such as methylsulfinyl, ethylsulfinyl, propylsulfinyl, etc. In particular, methylsulfinyl is preferred.

The alkylsulfonyl represented by $R^1$ includes, for example, alkylsulfonyl having 1 to 8 carbon atoms, preferably 1 to 4 carbon atoms, such as methylsulfonyl, ethylsulfonyl, propylsulfonyl, etc. In particular, methylsulfonyl is preferred.

The optionally substituted amino represented by $R^1$ includes, for example, amino, amino mono- or di-substituted by alkyl having 1 to 8 carbon atoms, preferably 1 to 4 carbon atoms (e.g., monomethylamino, dimethylamino, monoethylamino, etc.), amino mono-substituted by formyl, amino mono-substituted by alkylcarbonyl having 2 to 8 carbon atoms, preferably 2 to 4 carbon atom (e.g., methylcarbonylamino, etc.), etc. Amino substituted by alkyl having 1 to 4 carbon atoms is preferred. In particular, monomethylamino is preferred.

$R^1$ is preferably a halogen atom, alkyl, haloalkyl, alkoxyalkyl, hydroxyl, alkoxy, alkenyloxy, alkynyloxy, haloalkoxy, haloalkenyloxy, haloalkynyloxy, alkoxyalkoxy, alkylcarbonyloxy, (alkylthio)carbonyloxy, alkylsulfonyloxy, arylsulfonyloxy, mono- or di-alkyl-substituted carbamoyloxy, aryloxy, alkylthio, alkylsulfinyl, alkylsulfonyl, amino optionally substituted by alkyl, nitro, or tetrahydropyranyloxy. Alkoxy or hydroxy is more preferred. In particular, methoxy is preferred.

The optionally substituted aryl represented by Q includes, for example, aryl having 6 to 14 carbon atoms such as phenyl, naphthyl, etc. When the aryl is substituted, the substituent is selected from lower alkyl (wherein "lower" means $C_{1-8}$, preferably $C_{1-6}$, more preferably $C_{1-4}$; "lower" has the same meaning in other substituents described below) (e.g., methyl, ethyl, propyl, butyl, etc.), lower alkenyl (e.g., vinyl, allyl, crotyl, etc.), lower alkynyl (e.g., ethynyl, propargyl, butynyl, etc.), cycloalkyl (e.g., cyclopropyl, cyclopentyl, cyclohexyl, etc.), lower alkoxy lower alkyl (e.g., methoxymethyl, ethoxymethyl, 2-methoxyethyl, etc.), cycloalkenyl (e.g., cyclopentenyl, cyclohexenyl, etc.), lower alkanoyl (e.g., acetyl, propionyl, isobutyryl, etc.), lower alkylsilyl (e.g., trimethylsilyl, triethylsilyl, tripropylsilyl, tributylsilyl, etc.), halo(lower)alkyl (e.g., difluoromethyl, trifluoromethyl, chloromethyl, 2-bromoethyl, 2,3-dichloropropyl, etc.), di(lower)alkylamino (e.g., dimethylamino, diethylamino, etc.), phenyl, phenyl(lower)alkyl (e.g., benzyl, phenethyl, etc.), phenyl(lower)alkenyl (e.g., styryl, cinnamyl, etc.), furyl(lower)alkyl (e.g., 3-furylmethyl, 2-furylethyl, etc.), furyl(lower)alkenyl (e.g., 3-furylvinyl, 2-furylallyl, etc.), a halogen atom (e.g., fluorine, chlorine, bromine, iodine), nitro, cyano, lower alkylthio (e.g., methylthio, ethylthio, propylthio, etc.), lower alkoxycarbonyl (e.g., methoxycarbonyl, ethoxycarbonyl, propoxycarbonyl, etc.), formyl, amino, mono(lower)alkylamino (e.g., methylamino, ethylamino, etc.), —OR [wherein R is a hydrogen atom, lower alkyl (e.g., methyl, ethyl, propyl, butyl, etc.), lower alkenyl (e.g., vinyl, allyl, crotyl, etc.), lower alkynyl (e.g., ethynyl, 2-propynyl, 3-butynyl, etc.), halo(lower)alkyl (e.g., difluoromethyl, trifluoromethyl, chloromethyl, 2-bromoethyl, 2,3-dichloropropyl, etc.), lower alkanoyl (e.g., acetyl, propionyl, butyryl, etc.), phenyl, lower alkoxyphenyl (e.g., 3-methoxyphenyl, 4-ethoxyphenyl, etc.), nitrophenyl (e.g., 3-nitrophenyl, 4-nitrophenyl, etc.), phenyl(lower)alkyl (e.g., benzyl, phenethyl, phenylpropyl, etc.), cyanophenyl(lower)alkyl (e.g., 3-cyanophenylmethyl, 4-cyanophenylethyl, etc.), benzoyl, tetrahydropyranyl, pyridyl, trifluoromethylpyridyl, pyrimidinyl, benzothiazolyl, quinolyl, benzoyl(lower)alkyl (e.g., benzoylmethyl, benzoylethyl, etc.), benzenesulfonyl, or lower alkylbenzenesulfonyl (e.g., toluenesulfonyl, etc.)], —CH$_2$—G—R' (wherein G is —O—, —S—, or —NR"— (in which R" is a hydrogen atom or lower alkyl), R' is phenyl, halophenyl (e.g., 2-chlorophenyl, 4-fluorophenyl, etc.), lower alkoxyphenyl (e.g., 2-methoxyphenyl, 4-ethoxyphenyl, etc.), pyridyl, or pyrimidinyl], etc.

The substituent may be at any possible position in the ring. The number of the substituent(s) is 1 to 5, preferably 1 to 4, more preferably 1 to 3, and the substituents are the same or different.

Preferably, the optionally substituted aryl represented by Q is represented by the formula (XX):

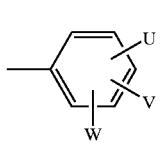

(XX)

wherein U, V and W are the same or different and are a hydrogen atom, halogen atom, optionally substituted alkyl, optionally substituted hydroxyl, alkylthio, or optionally substituted amino.

The halogen atom represented by U, V and W includes, for example, fluorine, chlorine, bromine, and iodine. In particular, chlorine is preferred.

The optionally substituted alkyl represented by U. V and W includes, for example, the above optionally substituted alkyl represented by $R^1$. The optionally substituted alkyl is preferably alkyl, haloalkyl or alkoxyalkyl, more preferably methyl, ethyl or trifluoromethyl, particularly preferably methyl.

The optionally substituted hydroxyl represented by U, V and W includes, for example, the above optionally substituted hydroxyl represented by $R^1$. The optionally substituted hydroxyl is preferably alkoxy, alkenyloxy, alkynyloxy, haloalkoxy or phenoxy, more preferably alkoxy, particularly preferably methoxy.

The alkylthio and optionally substituted amino represented by U, V and W include the above alkylthio and optionally substituted amino represented by $R^1$, respectively. In particular, they are preferably methylthio and dimethylamino, respectively.

The optionally substituted heterocyclic group represented by Q is, for example, a 5- to 7-membered heterocyclic group containing as a ring-constituting atom 1 to 4 heteroatoms selected from nitrogen, oxygen and sulfur. The heterocyclic group may form a condensed ring with another heterocyclic ring or a benzene ring. Examples of the heterocyclic group include pyridyl (e.g., pyridin-2-yl, pyridin-3-yl, etc), pyrimidinyl (e.g., pyrimidin-4-yl, pyrimidin-2-yl), quinolyl (e.g., quinolin-4-yl), quinazolinyl (e.g., quinazolin-4-yl), benzothiazolyl (e.g., benzothiazol-2-yl), pyrazolyl (e.g., pyrazol-5-yl), etc., each of which is optionally substituted. In particular, optionally substituted pyridyl is preferred.

When the heterocyclic group is substituted, the substituent includes, for example, the above substituents of the aryl represented by Q. The substituent is preferably a halogen atom, halo(lower)alkyl, alkoxy, alkoxycarbonyl or formyl, more preferably a chlorine atom or trifluoromethyl. The substituent may be at any possible position in the ring. The number of the substituent(s) is 1 to 5, preferably 1 to 4, more preferably 1 to 3. The substituents are the same or different.

The mono- or di-substituted methyleneamino represented by Q is represented, for example, by the formula

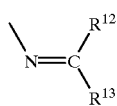

(a)

wherein $R^{12}$ and $R^{13}$ are the same or different and are a hydrogen atom, optionally substituted alkyl, acyl, alkylthio, alkylsulfinyl, alkylsulfonyl, optionally substituted amino, cycloalkyl, optionally substituted aryl or an optionally substituted heterocyclic group, or $R^{12}$ and $R^{13}$ are linked together to form a monocyclic or polycyclic ring which may contain a heteroatom, provided that at least one of $R^{12}$ and $R^{13}$ is not a hydrogen atom.

The alkyl represented by $R^{12}$ or $R^{13}$ in the formula (a) includes, for example, the alkyl or substituted alkyl represented by $R^1$. In particular, methyl and ethyl are preferred.

The acyl represented by $R^{12}$ or $R^{13}$ includes, for example, alkylcarbonyl, arylcarbonyl, etc. The alkylcarbonyl includes, for example, $C_{1-6}$ alkyl-carbonyl, preferably $C_{1-4}$ alkyl-carbonyl, such as acetyl, trifluoroacetyl, propionyl, butyryl, etc. The arylcarbonyl includes, for example, $C_{6-14}$ aryl-carbonyl such as benzoyl, naphthoyl, etc.

The alkylthio, alkylsulfinyl, alkylsulfonyl and optionally substituted amino represented by $R^{12}$ or $R^{13}$ are, for example, the alkylthio, alkylsulfinyl, alkylsulfonyl and optionally substituted amino represented by $R^1$, respectively.

The cycloalkyl represented by $R^{12}$ or $R^{13}$ includes cycloalkyl having 3 to 7 carbon atoms, preferably 5 to 6 carbon atoms, such as cyclopropyl, cyclobutyl, cyclopentyl, cyclohexyl, cycloheptyl, etc.

The optionally substituted aryl represented by $R^{12}$ or $R^{13}$ includes, for example, $C_{6-14}$ aryl such as phenyl, naphthyl (e.g., 1-naphthyl, etc.), fluorenyl, etc. In particular, phenyl is preferred. The aryl may be substituted at any possible position in the ring. The number of the substituent(s) is 1 to 3. Examples of the substituent include halogen atoms, optionally substituted alkyl, optionally substituted hydroxyl, alkylthio, optionally substituted amino, nitro, phenyl, cyano, etc.

Examples of the halogen atom as the substituent of the optionally substituted aryl represented by $R^{12}$ or $R^{13}$ include fluorine, chlorine, bromine, and iodine.

Examples of the optionally substituted alkyl as the substituent of the optionally substituted aryl represented by $R^{12}$ or $R^{13}$ include the above optionally substituted alkyl represented by $R^1$. The optionally substituted alkyl is preferably alkyl or haloalkyl, particularly preferably methyl or trifluoromethyl.

Examples of the optionally substituted hydroxyl as the substituent of the optionally substituted aryl represented by $R^{12}$ or $R^{13}$ include hydroxyl, alkoxy, alkenyloxy, alkynyloxy, haloalkoxy, aryloxy, etc. The alkoxy includes, for example, alkoxy having 1 to 8 carbon atoms, preferably 1 to 4 carbon atoms, such as methoxy, ethoxy, propoxy, butoxy, etc. In particular, methoxy is preferred. The alkenyloxy includes, for example, alkenyloxy having 2 to 8 carbon atoms, preferably 2 to 4 carbon atoms, such as vinyloxy, allyloxy, crotyloxy, etc. In particular, allyloxy is preferred. The alkynyloxy includes, for example, alkynyloxy having 2 to 8 carbon atoms, preferably 2 to 4 carbon atoms, such as ethynyloxy, propargyloxy, butynyloxy, etc. In particular, propargyloxy is preferred. The haloalkoxy includes, for example, the above alkoxy which is substituted by at least one halogen atom (e.g., fluorine, chlorine, bromine, iodine) such as difluoromethoxy, trifluoromethoxy, chloromethoxy, etc. In particular, difluoromethoxy is preferred. The aryloxy includes, for example, aryloxy having 6 to 12 carbon atoms, preferably 6 to 8 carbon atoms, such as phenoxy, naphthoxy, etc.

Examples of the alkylthio as the substituent of the optionally substituted aryl represented by $R^{12}$ or $R^{13}$ include alkylthio having 1 to 8 carbon atoms, preferably 1 to 4 carbon atoms, more preferably 1 to 2 carbon atoms, such as methylthio, ethylthio, propylthio, butylthio, etc. In particular, methylthio is preferred.

Examples of the optionally substituted amino as the substituent of the optionally substituted aryl represented by $R^{12}$ or $R^{13}$ include amino, amino which is mono- or di-substituted by alkyl having 1 to 8 carbon atoms, preferably 1 to 4 carbon atoms (e.g., monomethylamino, dimethylamino, monoethylamino, etc.), etc.

The optionally substituted heterocyclic group represented by $R^{12}$ or $R^{13}$ includes, for example, heterocyclic groups containing 1 to 4, preferably 1 to 2 heteroatoms (e.g., oxygen, nitrogen, sulfur, etc.). At any possible position, the heterocycle has the bond to the methylene carbon atom in the formula (a). Examples of the heterocyclic group include pyridyl, pyridazinyl, pyrazolyl, pyrimidinyl, furyl, thienyl, oxazolyl, isoxazolyl, benzothiazolyl, quinolyl, quinazolinyl, pyrazinyl, morpholino, piperazinyl, etc. Preferred examples thereof include furyl (e.g., 2-furyl, etc.), thienyl (e.g., 2-thienyl, etc.), pyridyl (2-pyridyl, etc.), pyrazinyl (e.g., 2-pyrazinyl, etc.), pyrimidinyl (e.g., 2-pyrimidinyl, etc.), and morpholino. The heterocyclic group is unsubstituted or substituted. The substituent includes the above substituents of the optionally substituted aryl represented by $R^{12}$ or $R^{13}$.

The monocyclic or polycyclic ring which is formed by $R^{12}$ and $R^{13}$ and may contain (a) heteroatom(s) is a 4- to 8-membered ring which is formed by $R^{12}$ and $R^{13}$ with the carbon atom to which they are attached. The ring may contain at least one heteroatom (e.g., oxygen, nitrogen, sulfur, etc) and may form a condensed ring with another ring. Examples of the ring include cyclopentane, cyclohexane, indan, 1,2,3,4-tetrahydronaphthalene, 5,6,7,8-tetrahydroquinoline, 4,5,6,7-tetrahydrobenzo[b]furan, etc. The ring has a bivalent bond at any possible position.

The optionally substituted (substituted imino)methyl represented by Q is represented, for example, by the formula (b):

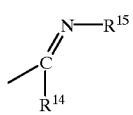

(b)

wherein $R^{14}$ and $R^{15}$ have the same meanings as the above $R^{12}$ and $R^{13}$, respectively.

The alkyl of the optionally substituted alkyl represented by Q includes the alkyl represented by $R^1$. The alkenyl of the optionally substituted alkenyl represented by Q includes, for example, alkenyl having 2 to 8 carbon atoms, preferably 3 to 6 carbon atoms, such as allyl, propenyl, isopropenyl, butenyl, isobutenyl, pentenyl, hexenyl, hexadienyl, etc. The alkynyl of the optionally substituted alkynyl represented by Q includes, for example, alkynyl having 2 to 6 carbon atoms, preferably 2 to 4 carbon atoms, such as propargyl, ethynyl, butynyl, etc. When the alkyl, alkenyl and alkynyl are substituted, the substituents are, for example, the above halogen atom, alkoxy, alkylthio, alkylsulfinyl, alkylsulfonyl and substituted amino, each of which is represented by $R^1$; the above optionally substituted phenyl, optionally substituted naphthyl, and optionally substituted heterocyclic group, each of which is represented by Q; etc.

The substituted carbonyl represented by Q includes, for example, (optionally substituted alkyl)carbonyl, (optionally substituted phenyl)carbonyl, (optionally substituted naphthyl)carbonyl, (optionally substituted heterocyclic group)carbonyl, etc.

The substituted sulfonyl represented by Q includes, for example, (optionally substituted alkyl)sulfonyl, (optionally substituted phenyl)sulfonyl, (optionally substituted naphthyl)sulfonyl, (optionally substituted heterocyclic group)sulfonyl, etc.

The optionally substituted alkyl in the above substituted carbonyl or substituted sulfonyl includes the above optionally substituted alkyl represented by $R^1$. The optionally substituted phenyl, optionally substituted naphthyl, and optionally substituted heterocyclic group include the corresponding groups represented by Q.

Q is preferably a group of the formula (XX); pyridyl, pyrimidinyl, quinolyl, quinazolinyl, benzothiazolyl or pyrazolyl, each of which is unsubstituted or substituted; or a group of the formula (a).

X is a hydrogen atom, halogen atom, optionally substituted alkyl or optionally substituted hydroxyl. This is intended to include a case where the phenylene group in the above formula (I) is unsubstituted, i.e., X is a hydrogen atom; and a case wherein the phenylene group is substituted at any possible position by 1 to 3 substituents selected from a halogen atom, optionally substituted alkyl and optionally substituted hydroxyl. When the phenylene group is substituted by 2 or 3 substituents, the substituents are the same or different.

The halogen atom, optionally substituted alkyl and optionally substituted hydroxyl represented by X include, for example, the corresponding groups represented by $R^1$, respectively.

X is preferably a hydrogen atom.

The optionally substituted hydroxyl and alkylthio represented by Y include, for example, the corresponding groups represented by $R^1$. In particular, methoxy is preferred.

The optionally substituted amino represented by Y is represented, for example, by the formula (XXI):

$$—NR^5R^6 \qquad (XXI)$$

wherein $R^5$ is a hydrogen atom or alkyl; $R^6$ is a hydrogen atom, alkyl or hydroxylalkyl. The alkyl represented by $R^5$ or $R^6$ and the alkyl of the hydroxylalkyl represented by $R^6$ include, for example, the above alkyl represented by $R^1$. Preferably, $R^5$ and $R^6$ are the same or different and are a hydrogen atom or alkyl (preferably methyl). More preferably, the group of the formula (XXI) as Y is monoalkylamino, particularly preferably monomethylamino.

Y is preferably alkoxy or a group of the formula (XXI), more preferably methoxy or monoalkylamino (preferably monomethylamino).

Z is preferably an oxygen atom.

The alkyl represented by $R^2$ includes, for example, the above alkyl represented by $R^1$. In particular, methyl is preferred.

The acyl represented by $R^2$ includes formyl; alkylcarbonyl containing alkyl having 1 to 8 carbon atoms, preferably 1 to 4 carbon atoms (e.g., acetyl, propionyl, butyryl, etc.); benzoyl; etc. In particular, acetyl is preferred.

M is preferably an oxygen atom, sulfur atom or $NR^2$, more preferably an oxygen atom.

n is preferably 0 or 1.

The compound of the formula (I) of the present invention has an asymmetric carbon atom at the 2-position. Each optical isomer and mixtures thereof are included in the present invention.

Preferred examples of the compound of the formula (I) are that wherein:

X is a hydrogen atom, $R^1$ is hydroxyl, Z is an oxygen atom, Y is amino optionally substituted by alkyl, M is an oxygen atom, Q is optionally substituted phenyl, and n is 0 or 1;

X is a hydrogen atom, $R^1$ is alkoxy, Z is an oxygen atom, Y is alkoxy or optionally substituted amino, M is an oxygen atom, Q is optionally substituted phenyl, and n is 0 or 1;

X is a hydrogen atom, $R^1$ is hydroxyl, Z is an oxygen atom, Y is amino optionally substituted by alkyl, M is an oxygen atom, Q is an optionally substituted heterocyclic group, and n is 0 or 1;

X is a hydrogen atom, $R^1$ is alkoxy, Z is an oxygen atom, Y is alkoxy or optionally substituted amino, M is an oxygen atom, Q is an optionally substituted heterocyclic group, and n is 0 or 1;

X is a hydrogen atom, $R^1$ is alkoxy, Z is an oxygen atom, Y is amino optionally substituted by alkyl, M is an oxygen atom, Q is a group of the formula (a), $R^{12}$ is alkyl, $R^{13}$ is optionally substituted phenyl or optionally substituted morpholino, and n is 1; or X is a hydrogen atom, $R^1$ is alkoxy, Z is an oxygen atom, Y is amino optionally substituted by alkyl, M is acylamino, Q is a group of the formula (a), $R^{12}$ is alkyl, $R^{13}$ is optionally substituted phenyl or optionally substituted morpholino, and n is 1.

More preferred examples of the compound of the formula (I) are that wherein:

X is a hydrogen atom, $R^1$ is hydroxyl, Z is an oxygen atom, Y is monomethylamino, M is an oxygen atom, Q is phenyl, and n is 0 (Compound No. 1);

X is a hydrogen atom, $R^1$ is hydroxyl, Z is an oxygen atom, Y is amino, M is an oxygen atom, Q is phenyl, and n is 0 (Compound No. 2);

X is a hydrogen atom, $R^1$ is hydroxyl, Z is an oxygen atom, Y is monomethylamino, M is an oxygen atom, Q is 3,4-dimethylphenyl, and n is 0 (Compound No. 15);

X is a hydrogen atom, $R^1$ is hydroxyl, Z is an oxygen atom, Y is monomethylamino, M is an oxygen atom, Q is 3,5-dimethylphenyl, and n is 0 (Compound No. 16);

X is a hydrogen atom, $R^1$ is hydroxyl, Z is an oxygen atom, Y is monomethylamino, M is an oxygen atom, Q is 2-methylphenyl, and n is 1 (Compound No. 64);

X is a hydrogen atom, $R^1$ is hydroxyl, Z is an oxygen atom, Y is monomethylamino, M is an oxygen atom, Q is 2,5-dimethylphenyl, and n is 1 (Compound No. 75);

X is a hydrogen atom, $R^1$ is hydroxyl, Z is an oxygen atom, Y is monomethylamino, M is an oxygen atom, Q is 4-chloro-2-methylphenyl, and n is 1 (Compound No. 113);

X is a hydrogen atom, $R^1$ is methoxy, z is an oxygen atom, Y is methoxy, M is an oxygen atom, Q is 2,5-dimethylphenyl, and n is 1 (Compound No. 139);

X is a hydrogen atom, $R^1$ is methoxy, Z is an oxygen atom, Y is monomethylamino, M is an oxygen atom, Q is 2,5-dimethylphenyl, and n is 1 (Compound No. 140);

X is a hydrogen atom, $R^1$ is methoxy, Z is an oxygen atom, Y is monomethylamino, M is an oxygen atom, Q is 4-chloro-2-methylphenyl, and n is 1 (Compound No. 186);

X is a hydrogen atom, $R^1$ is methoxy, Z is an oxygen atom, Y is monomethylamino, M is an oxygen atom, Q is 2-methylphenyl, and n is 1 (Compound No. 197);

X is a hydrogen atom, $R^1$ is methoxy, Z is an oxygen atom, Y is monomethylamino, M is an oxygen atom, Q is 3-chloro-5-trifluoromethylpyridin-2-yl, and n is 1 (Compound No. 427);

X is a hydrogen atom, $R^1$ is methoxy, Z is an oxygen atom, Y is monomethylamino, M is an oxygen atom, Q is 3,5-dichloropyridin-2-yl, and n is 1 (Compound No. 433);

X is a hydrogen atom, $R^1$ is methoxy, Z is an oxygen atom, Y is monomethylamino, M is an oxygen atom, Q is 3-trifluoromethyl- 5-chloropyridin-2-yl, and n is 1 (Compound No. 448);

X is a hydrogen atom, $R^1$ is methoxy, Z is an oxygen atom, Y is monomethylamino, M is an oxygen atom, Q is 3-chloropyridin-2-yl, and n is 1 (Compound No. 466);

X is a hydrogen atom, $R^1$ is methoxy, Z is an oxygen atom, Y is monomethylamino, M is an oxygen atom, Q is α-methyl-4-chlorobenzylideneamino, and n is 1 (Compound No. 474);

X is a hydrogen atom, $R^1$ is methoxy, Z is an oxygen atom, Y is monomethylamino, M is an oxygen atom, Q is α-methyl-4-methoxybenzylideneamino, and n is 1 (Compound No. 492);

X is a hydrogen atom, $R^1$ is methoxy, Z is an oxygen atom, Y is monomethylamino, M is an oxygen atom, Q is 4, α-dimethylbenzylideneamino, and n is 1 (Compound No. 498); or X is a hydrogen atom, $R^1$ is methoxy, Z is an oxygen atom, Y is monomethylamino, M is an oxygen atom, Q is α-methyl-4-trifluoromethylbenzylideneamino, and n is 1 (Compound No. 526).

The compounds of the present invention included in the formula (I) can preferably be prepared as follows.

METHOD A

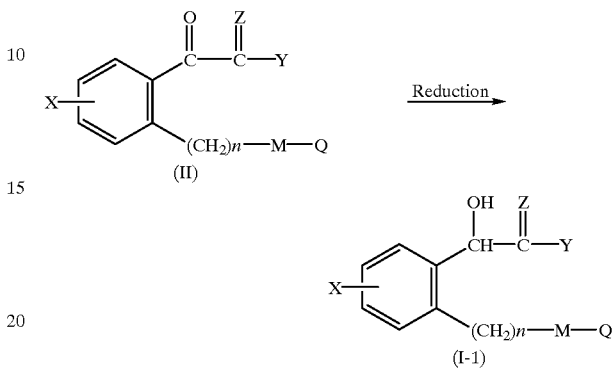

wherein each symbol is as defined above.

The compound of the formula (I-1) of the present invention can be prepared by reducing the compound (II).

The reducing agent to be used is a conventional reducing agent for reduction of ketones, such as metal hydrides, metal hydride complex compounds, etc. Examples of the reducing agent include three-coordinate borane (e.g., borane, etc.), four-coordinate borate (e.g., sodium borohydride, lithium borohydride, etc.), three-coordinate aluminium (e.g., diisobutylaluminum hydride, etc.), four-coordinate alumininate complex (e.g., lithium aluminum hydride, etc.), etc. The amount of the reducing agent to be used is 0.25 to 3 mol, preferably 1.0 to 1.2 mol, per mol of the compound (II).

Examples of the solvent include alcohols such as methanol, ethanol, etc.; ethers such as diethyl ether, tetrahydofuran, etc.; water, etc. These solvents can be used alone or as a mixture thereof.

The reaction temperature is appropriately selected from the range of −20° C. to a reflux temperature of the solvent, and is preferably 0 to 50° C. The reaction time is 0.5 hour to 24 hours, preferably 0.5 to 2 hours.

The compound (I-1) of the present invention thus obtained can be separated and purified by known methods (e.g., chromatography, recrystallization, etc.).

The compound (II) used as the starting material in this reaction can be prepared, for example, according to JP-A 3-246268, JP-A 5-97768 or JP-A 5-331124, for example, by reacting the corresponding halogenated phenyl with butyllithium or magnesium, and then reacting the resulting compound with dialkyl oxalate. Alternatively, it can be prepared by Method Q described below.

METHOD B

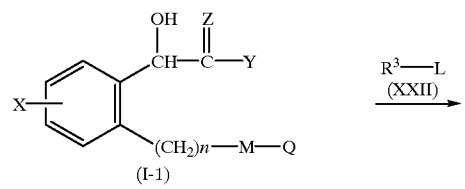

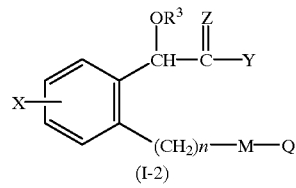

(I-2)

wherein $R^3$ is alkyl, alkenyl, alkynyl, haloalkyl, haloalkenyl, haloalkynyl, alkoxyalkyl, alkylcarbonyl, (alkylthio) carbonyl, alkylsulfonyl, arylsulfonyl or mono- or di-alkyl-substituted carbamoyl, L is a leaving group or $R^3$-L represents dihydropyran, and the other symbols are as defined above.

The groups represented by $R^3$ are, for example, groups corresponding to the substituents of the above substituted hydroxyl represented by $R^1$. The leaving group represented by L includes, for example, halogen atoms (e.g., fluorine, chlorine, bromine, iodine), alkylsulfonyloxy (e.g., methanesulfonyloxy, etc.), etc.

The compound (I-2) of the present invention can be prepared by reacting the compound (I-1) of the present invention with the compound (XXII) to introduce alkyl, alkenyl, alkynyl, carbonyl, sulfonyl, carbamoyl or tetrahydropyranyl into the compound (I-1).

The alkyl, alkenyl and alkynyl can be introduced, for example, by using as the compound (XXII) an alkyl halide, alkenyl halide and alkynyl halide, respectively, in the presence of a base. The alkyl halide includes, for example, methyl chloride, methyl bromide, methyl iodide, ethyl chloride, ethyl bromide, ethyl iodide, 1-iodopropane, 2-iodopropane, 1-iodobutane, chlorotrifluoromethane, 1,2-dibromoethane, chloromethyl ether, etc. The alkenyl halide includes, for example, allyl bromide, etc. The alkynyl halide includes, for example, propargyl bromide, etc. The amount of the halide to be used is 1 to 5 mol, preferably 1 to 2 mol, per mol of the compound (I-1).

Examples of the base include organic bases (e.g., sodium methoxide, sodium ethoxide, potassium t-butoxide, etc.), inorganic bases (e.g., sodium hydroxide, potassium hydroxide, sodium hydride, potassium hydride, etc.), etc. The amount of the base to be used is 1 to 5 mol, preferably 1 to 2 mol, per mol of the compound (I-1).

Examples of the solvent include ethers such as diethyl ether, tetrahydrofuran, etc.; N,N-dimethylformamide, dimethyl sulfoxide, toluene, etc.

The reaction temperature is appropriately selected from the range of −20° C. to a reflux temperature of the solvent, and is preferably 0 to 50° C. The reaction time is 0.5 hour to 48 hours, preferably 0.5 to 10 hours.

The carbonyl can be introduced, for example, by using as the compound (XXII) an acid halide (e.g., acetyl chloride, acetyl bromide, propionyl chloride, thioacetyl chloride, etc.) or acid anhydride (e.g., acetic anhydride, propionic anhydride, etc.) in the presence of a base. The amount of the acid halide or acid anhydride to be used is 1 to 5 mol, preferably 1 to 2 mol, per mol of the compound (I-1).

Examples of the base include organic bases (e.g., triethylamine, N,N-dimethylaniline, pyridine, etc.) or inorganic bases (sodium carbonate, potassium carbonate, sodium hydride, etc.). The amount of the base to be used is 1 to 5 mol, preferably 1 to.2 mol, per mol of the compound (I-1).

Examples of the solvent include halogenated hydrocarbons such as methylene chloride, chloroform, etc.; ethers such as diethyl ether, tetrahydrofuran, etc.; N,N-dimethylformamide, dimethyl sulfoxide, toluene, etc.

The reaction temperature is appropriately selected from the range of −20° C. to a reflux temperature of the solvent, and is preferably 0 to 50° C. The reaction time is 0.5 hour to 24 hours, preferably 0.5 to 5 hours.

The sulfonyl can be introduced, for example, by using as the compound (XXII) an alkylsulfonyl halide (e.g., alkylsulfonyl chloride such as methanesulfonyl chloride, ethanesulfonyl chloride, etc.) or arylsulfonyl halide (e.g., arylsulfonyl chloride such as benzenesulfonyl chloride, p-toluenesulfonyl chloride, etc.) in the presence of a base. The amount of the alkylsulfonyl halide or arylsulfonyl halide to be used is 1 to 5 mol, preferably 1 to 2 mol, per mol of the compound (I-1).

Examples of the base include organic bases (e.g., triethylamine, N,N-dimethylaniline, pyridine, etc.) or inorganic bases (e.g., sodium carbonate, potassium carbonate, sodium hydride, etc.). The amount of the base to be used is 1 to 5 mol, preferably 1 to 2 mol, per mol of the compound (I-1).

Examples of the solvent include halogenated hydrocarbons such as methylene chloride, chloroform, etc.; ethers such as diethyl ether, tetrahydrofuran, etc.; N,N-dimethylformamide, dimethyl sulfoxide, toluene, etc.

The reaction temperature is appropriately selected from the range of −20° C. to a reflux temperature of the solvent, and is preferably 0 to 50° C. The reaction time is 0.5 hour to 24 hours, preferably 0.5 to 5 hours.

The carbamoyl can be introduced, for example, by using as the compound (XXII) an N-unsubstituted or N-alkyl substituted carbamoyl halide (e.g., monoethylcarbamoyl chloride, dimethylcarbamoyl chloride, etc.). The amount of the carbamoyl halide to be used is 1 to 5 mol, preferably 1 to 2 mol, per mol of the compound (I-1).

Examples of the base include organic bases (e.g., triethylamine, N,N-dimethylaniline, pyridine, etc.) or inorganic bases (e.g., sodium carbonate, potassium carbonate, sodium hydride, etc.). The amount of the base to be used is 1 to 5 mol, preferably 1 to 2 mol, per mol of the compound (I-1).

Examples of the solvent include halogenated hydrocarbons such as methylene chloride, chloroform, etc.; ethers such as diethyl ether, tetrahydrofuran, etc.; N,N-dimethylformamide, dimethyl sulfoxide, toluene, etc.

The reaction temperature is appropriately selected from the range of −20° C. to a reflux temperature of the solvent, and is preferably 20 to 70° C. The reaction time is 0.5 hour to 48 hours, preferably 0.5 to 12 hours.

The tetrahydropyranyl can be introduced by a conventional method for protecting a hydroxyl group with tetrahydropyranyl, for example, according to the same manner as in Method Y described below.

The compound (I-2) of the present invention thus obtained can be separated and purified by conventional methods (e.g., chromatography, recrystallization, etc.).

METHOD C

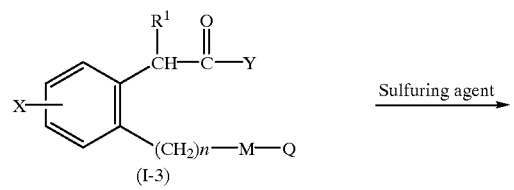

(I-3)

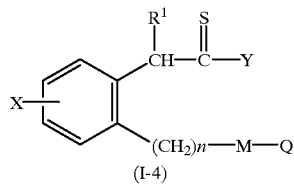

wherein each symbol is as defined above.

The compound (I-4) of the present invention can be prepared by reacting the compound (I-3) of the present invention with a sulfuring agent (i.e., sulfur-introducing agent).

The sulfuring agent includes, for example, phosphorus pentasulfide and Lawesson's reagent. The amount of the sulfuring agent to be used is 1 to 5.mol, preferably 1 to 2 mol. per mol of the compound (I-3).

Examples of the solvent include aromatic hydrocarbons such as toluene, xylene, etc; and pyridine. These solvents can be used alone or as a mixture thereof.

The reaction temperature is appropriately selected from the range of room temperature to a reflux temperature of the solvent, and is preferably 80° C. to 150° C. The reaction time is 0.5 hour to 48 hours, preferably 0.5 to 12 hours.

The compound (I-4) of the present invention thus obtained can be separated and purified by known methods (e.g., chromatography, recrystallization, etc.).

METHOD D

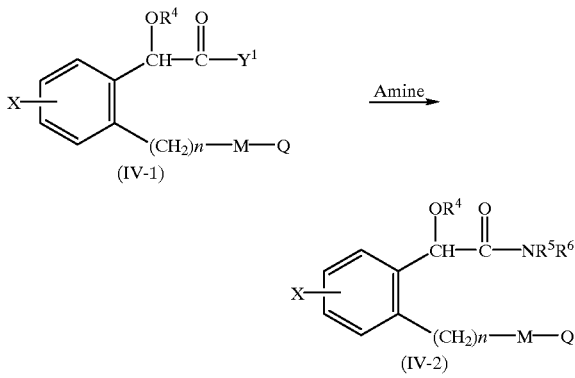

wherein $R^4$ is alkyl, alkenyl, alkynyl, haloalkyl, haloalkenyl, haloalkynyl or alkoxyalkyl, $R^5$ is a hydrogen atom or alkyl, $R^6$ is a hydrogen atom, alkyl or hydroxyalkyl, $Y^1$ is alkoxy or alkylthio, and the other symbols are as defined above.

The groups represented by $R^4$ are, for example, groups corresponding to the substituents of the above substituted hydroxyl represented by $R^1$. The alkoxy and alkylthio represented by Y1 include, for example, the above alkoxy and alkylthio represented by $R^1$, respectively.

The compound (IV-2) of the present invention can be prepared by reacting the compound (IV-1) with an amine.

The amine includes compounds of the formula (V): $R^5R^6NH$ (wherein $R^5$ and $R^6$ are as defined above). Examples thereof include liquid ammonia; primary amines such as methylamine, ethylamine, etc.; secondary amines such as dimethylamine, diethylamine, etc. The amount of the amine to be used is 1 to 5 mol, preferably 1 to 2 mol, per mol of the compound (IV-1).

Examples of the solvent include alcohols such as methanol, ethanol, etc.; aromatic hydrocarbons such as toluene, xylene, etc.; halogenated hydrocarbons such as methylene chloride, chloroform, etc.; ethers such as ether, tetrahydrofuran, etc.; and water. These solvents can be used alone or as a mixture thereof.

The reaction temperature is appropriately selected from the range of 0° C. to a reflux temperature of the solvent, and is preferably 20° C. to 80° C. The reaction time is 0.5 hour to 48 hours, preferably 0.5 to 12 hours.

The compound (IV-2) of the present invention thus obtained can be separated and purified by known methods (e.g., chromatography, recrystallization, etc.).

METHOD E

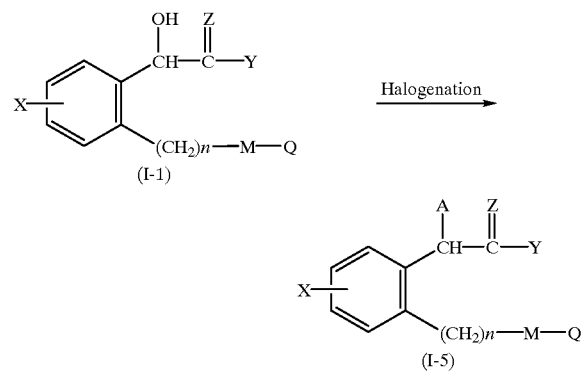

wherein A is a halogen atom, and the other symbols are as defined above.

The halogen atom represented by A includes, for example, fluorine, chlorine, bromine and iodine.

The compound (I-5) of the present invention can be prepared by halogenating the compound (I-1) of the present invention. The halogenating agent to be used in the halogenation includes, for example, chlorinating agents such as thionyl chloride, phosphorus oxychloride, phosphorus pentachloride, carbon tetrachloride-triphenylphosphine, etc.; brominating agents such as thionyl bromide, phosphorus tribromide, carbon tetrabromide-triphenylphosphine, etc. The amount of the halogenating agent to be used is 1 to 5 mol, preferably 1 to 2 mol, per mol of the compound (I-1).

Examples of the solvent include aromatic hydrocarbons such as toluene, xylene, etc.; halogenated hydrocarbons such as methylene chloride, chloroform, etc.; ethers such as ether, tetrahydrofuran, etc.

The reaction temperature is appropriately selected from the range of 0° C. to a reflux temperature of the solvent, and is preferably 20° C. to 80° C. The reaction time is 0.5 hour to 48 hours, preferably 0.5 to 12 hours.

The compound (I-5) of the present invention thus obtained can be separated and purified by known methods (e.g., chromatography, recrystallization, etc.).

METHOD F

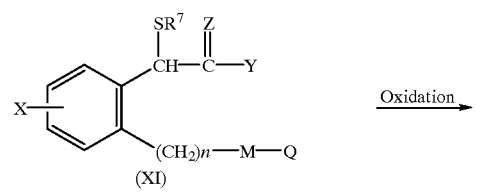

-continued

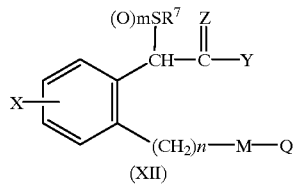

wherein $R^7$ is alkyl, m is 1 or 2, and the other symbols are as defined above.

The alkyl represented by $R^7$ includes, for example, the above alkyl represented by $R^1$.

The compound (XII) of the present invention can be prepared by oxidizing the compound (XI) of the present invention. The oxidizing agent to be used in the oxidation includes, for example, hydrogen peroxide, peracids such as peracetic acid, perbenzoic acid, m-chloroperbenzoic acid, etc., sodium metaperiodate, hydroperoxide, etc. The amount of the oxidizing agent to be used is 1 to 10 mol, preferably 1 to 3 mol, per mol of the compound (XI).

Examples of the solvent include aromatic hydrocarbons such as toluene, xylene, etc.; halogenated hydrocarbons such as methylene chloride, chloroform, etc.; ethers such as ether, tetrahydrofuran, etc., alcohols such as methanol, ethanol, etc.; and water. These solvents can be used alone or as a mixture thereof.

The reaction temperature is appropriately selected from the range of –20° C. to a reflux temperature of the solvent, and is preferably 0° C. to 50° C. The reaction time is 0.5 hour to 48 hours, preferably 0.5 to 12 hours.

The compound (XII) of the present invention thus obtained can be separated and purified by known methods (e.g., chromatography, recrystallization, etc.).

METHOD G

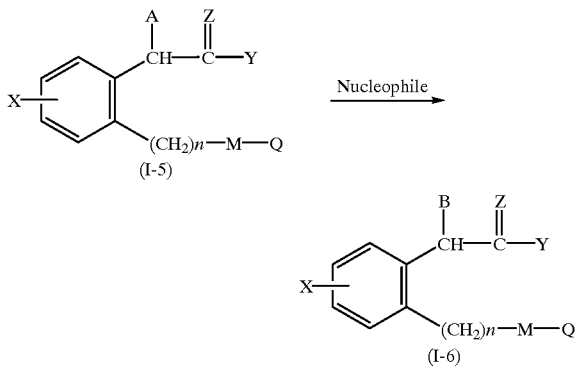

wherein A is a halogen atom, B is optionally substituted hydroxyl, alkylthio, amino optionally substituted by alkyl, or nitro, and the other symbols are as defined above.

The groups represented by B include, for example, the above corresponding groups represented by $R^1$.

The compound (I-6) of the present invention can be prepared by reacting the compound (I-5) of the present invention with a nucleophile to displace the group A.

For example, when A is displaced by substituted hydroxyl, for example, a metal salt of an alcohol (e.g., sodium methoxide, sodium 2-propenoxide, potassium 2-propynoxide, potassium 2,2,2-trifluoroethoxide, sodium methoxymethoxide, etc.) may directly be used as the nucleophile, or a metal salt of an alcohol is formed in the reaction mixture from an alcohol and a metal hydride (e.g., sodium hydride, potassium hydride, etc.) to use it in the reaction. In both cases, the amount of the metal salt of an alcohol to be used is 1 to 5 mol, preferably 1 to 2 mol, per mol of the compound (I-5).

Examples of the solvent to be used include aromatic hydrocarbons such as toluene, xylene, etc.; halogenated hydrocarbons such as methylene chloride, chloroform, etc.; ethers such as ether, tetrahydrofuran, etc.; N,N-dimethylformamide, and dimethyl sulfoxide.

The reaction temperature is appropriately selected from the range of 0° C. to a reflux temperature of the solvent, and is preferably 20° C. to 80° C. The reaction time is 0.5 hour to 48 hours, preferably 0.5 to 12 hours.

When the group A is displaced by alkylthio, for example, a metal salt of an alkylmercaptan (e.g., sodium thiomethoxide, sodium thioethoxide, etc.) may directly be used as the nucleophile, or a metal salt of an alkylmercaptan is formed in the reaction mixture from an alkylmercaptan and a metal hydride (e.g., sodium hydride, potassium hydride, etc.) or a hydroxide (e.g., sodium hydroxide, potassium hydroxide, etc.) to use it in the reaction. In both cases, the amount of the metal salt of an alkylmercaptan to be used is 1 to 5 mol, preferably 1 to 2 mol, per mol of the compound (I-5)

Examples of the solvent to be used include aromatic hydrocarbons such as toluene, xylene, etc.; ethers such as ether, tetrahydrofuran, etc.; acetonitrile, N,N-dimethylformamide, dimethyl sulfoxide, and water. These solvents can be used alone or as a mixture thereof.

The reaction temperature is appropriately selected from the range of 0° C. to a reflux temperature of the solvent, and is preferably 20° C. to 80° C. The reaction time is 0.5 hour to 48 hours, preferably 0.5 to 12 hours.

When the group A is displaced by amino optionally substituted by alkyl, for example, an amine (e.g., liquid ammonia, ammonia water, monomethylamine, dimethylamine, etc.) is used as the nucleophile in an amount of 1 to 5 mol, preferably 1 to 2 mol, per mol of the compound (I-5).

Examples of the solvent to be used include aromatic hydrocarbons such as toluene, xylene, etc.; ethers such as ether, tetrahydrofuran, etc.; alcohols such as methanol, ethanol, etc.; N,N-dimethylformamide, dimethyl sulfoxide, and water. These solvents can be used alone or as a mixture thereof.

The reaction temperature is appropriately selected from the range of –20° C. to a reflux temperature of the solvent, and is preferably 0° C. to 80° C. The reaction time is 0.5 hour to 48 hours, preferably 0.5 to 12 hours.

When the group A is displaced by nitro, for example, a nitrite (e.g., sodium nitrite, potassium nitrite, etc.) is used as the nucleophile in an amount of 1 to 5 mol, preferably 1 to 2 mol, per mol of the compound (I-5). In addition, phloroglucinol is used in an amount of 1 to 5 mol, preferably 1 to 2 mol. per mol of the compound (I-5).

Examples of the solvent to be used include aromatic hydrocarbons such as toluene, xylene, etc.; ethers such as ether, tetrahydrofuran, etc.; alcohols such as methanol, ethanol, etc.; N,N-dimethylformamide, and dimethyl sulfoxide.

The reaction temperature is appropriately selected from the range of 0° C. to a reflux temperature of the solvent, and is preferably 20° C. to 80° C. The reaction time is 0.5 hour to 48 hours, preferably 0.5 to 12 hours.

The compound (I-6) of the present invention thus obtained can be separated and purified by known methods (e.g., chromatography, recrystallization, etc.).

METHOD H

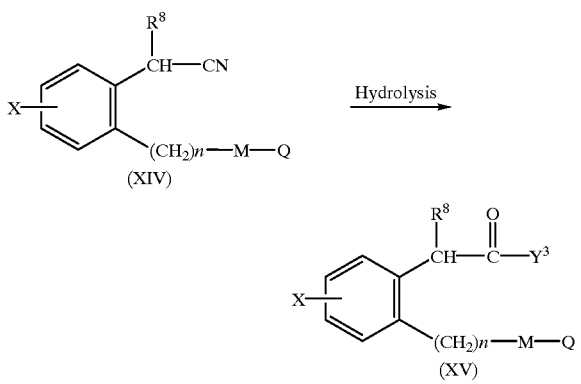

wherein $R^8$ is alkyl, haloalkyl or alkoxyalkyl, $Y^3$ is hydroxyl or amino, and the other symbols are as defined above.

The groups represented by $R^8$ include, for example, the above corresponding groups represented by $R^1$.

The compound (XV) of the present invention can be prepared by hydrolyzing the compound (XIV) with an acid or base.

Examples of the acid include mineral acids (e.g., hydrochloric acid, hydrobromic acid, sulfuric acid, nitric acid, phosphoric acid, etc.) and organic acids (e.g., formic acid, acetic acid, etc.). These acids can be used alone or as a mixture thereof. Examples of the base include organic bases (e.g., sodium ethoxide, etc.) and inorganic bases (e.g., sodium hydroxide, potassium hydroxide, etc.). The amount of the acid or base to be used is 1 to 10 mol, preferably 1 to 3 mol, per mol of the compound (XIV).

Examples of the solvent to be used include aromatic hydrocarbons such as toluene, xylene, etc.; ethers such as ether, tetrahydrofuran, etc.; alcohols such as methanol, ethanol, etc.; N,N-dimethylformamide, dimethyl sulfoxide, water, etc. These solvents can be used alone or as a mixture thereof.

The reaction temperature is appropriately selected from the range of –80° C. to a reflux temperature of the solvent, and is preferably 0° C. to 80° C. The reaction time is 0.5 hour to 48 hours, preferably 0.5 to 6 hours.

The compound (XV) of the present invention thus obtained can be separated and purified by known methods (e.g., chromatography, recrystallization, etc.).

The compound (XIV) used as the starting material in this reaction can be prepared, for example, by Method R described below.

METHOD I

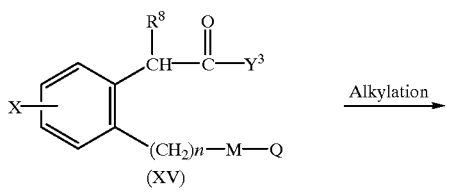

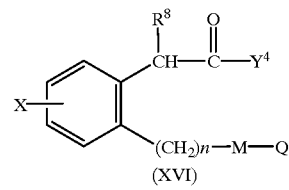

wherein $Y^4$ is alkoxy, mono- or di-alkyl-substitiuted amino, and the other symbols are as defined above.

The groups represented by $Y^4$ include the above corresponding groups represented by $R^1$.

The compound (XVI) of the present invention can be prepared by alkylating the compound (XV) of the present invention. The alkylation can be carried out using an alkyl halide in the presence of a base. Examples of the alkyl halide include methyl chloride, methyl bromide, methyl iodide, ethyl chloride, ethyl bromide, ethyl iodide, 1-iodopropane, 2-iodopropane, 1iodobutane, etc. The amount of the alkyl halide to be used is 1 to 5 mol, preferably 1 to 2 mol, per mol of the compound (XV).

Examples of the base include organic bases (e.g., butyllithium, sodium ethoxide, etc.) and inorganic bases (e.g., sodium hydroxide, potassium hydroxide, sodium amide, sodium hydride, etc.). The amount of the base to be used is 1 to 5 mol, preferably 1 to 2 mol, per mol of the compound (XV).

Examples of the solvent to be used include aromatic hydrocarbons such as toluene, xylene, etc.; halogenated hydrocarbons such as methylene chloride, chloroform, etc.; ethers such as ether, tetrahydrofuran, etc.; alcohols such as methanol, ethanol, etc.; N,N-dimethylformamide, dimethyl sulfoxide, etc.

The reaction temperature is appropriately selected from the range of –80° C. to a reflux temperature of the solvent, and is preferably 0° C. to 80° C. The reaction time is 0.5 hour to 48 hours, preferably 0.5 to 6 hours.

The compound (XVI) of the present invention thus obtained can be separated and purified by known methods (e.g., chromatography, recrystallization, etc.).

METHOD J

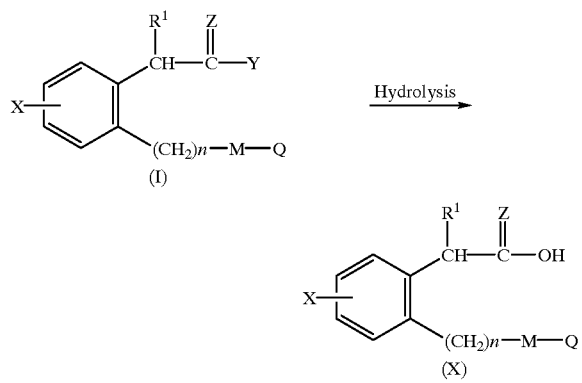

wherein each symbol is as defined above.

The compound (X) of the present invention can be prepared by hydrolyzing the compound (I) of the present invention in an appropriate solvent.

The hydrolysis can be carried out by treating the compound (I) with a base. Examples of the base include organic bases (e.g., metal alkoxides such as sodium ethoxide, etc.)

and inorganic bases (e.g., metal hydroxides such as sodium hydroxide, potassium hydroxide, etc.). The amount of the base to be used is 1 to 10 mol, preferably 1 to 3 mol, per mol of the compound (I).

Examples of the solvent to be used include aromatic hydrocarbons such as toluene, xylene, etc.; ethers such as ether, tetrahydrofuran, etc.; alcohols such as methanol, ethanol, etc.; N,N-dimethylformamide, dimethyl sulfoxide, water, etc. These solvents can be used alone or in combination thereof.

The reaction temperature is appropriately selected from the range of −80° C. to a reflux temperature of the solvent, and is preferably 0° C. to 80° C. The reaction time is 0.5 hour to 48 hours, preferably 0.5 to 6 hours.

The compound (X) of the present invention thus obtained can be separated and purified by known methods (e.g., chromatography, recrystallization, etc.).

METHOD K

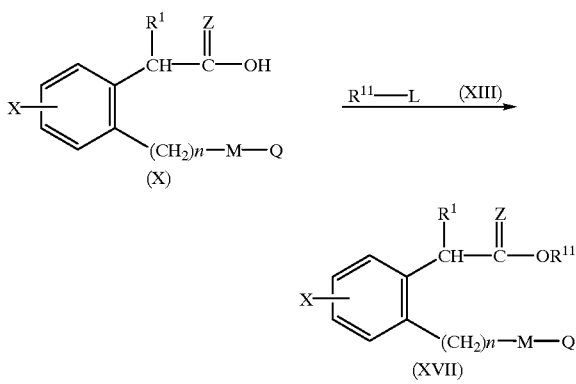

wherein $R^{11}$ is alkyl, alkenyl or alkynyl, and the other symbols are as defined above.

The compound (XVII) of the present invention can be prepared by reacting the compound (X) of the present invention with the compound (XIII).

This reaction can be carried, for example, by using an alkyl halide, alkenyl halide or alkynyl halide as the compound (XIII) in the presence of a base. The alkyl halide includes, for example, methyl chloride, methyl bromide, methyl iodide, ethyl chloride, ethyl bromide, ethyl iodide, 1-iodopropane, 2-iodopropane, 1-iodobutane, chlorotrifluoromethane, 1,2-dibromoethane, chloromethyl ether, etc. The alkenyl halide includes, for example, allyl bromide, etc. The alkynyl halide includes, for example, propargyl bromide, etc. The amount of the halide to be used is 1 to 5 mol, preferably 1 to 2 mol, per mol of the compound Examples of the base include organic bases (e.g., sodium methoxide, sodium ethoxide, potassium t-butoxide, etc.), inorganic bases (e.g., sodium hydroxide, potassium hydroxide, sodium hydride, potassium hydride, etc.), etc. The amount of the base to be used is 1 to 5 mol, preferably 1 to 2 mol, per mol of the compound (X).

Examples of the solvent to be used include ethers such as diethyl ether, tetrahydrofuran, etc.; N,N-dimethylformamide, dimethyl sulfoxide, toluene, etc.

The reaction temperature is appropriately selected from the range of −20° C. to a reflux temperature of the solvent, and is preferably 0° C. to 50° C. The reaction time is 0.5 hour to 48 hours, preferably 0.5 to 10 hours.

The compound (XVII) of the present invention thus obtained can be separated and purified by known methods (e.g., chromatography, recrystallization, etc.).

METHOD L

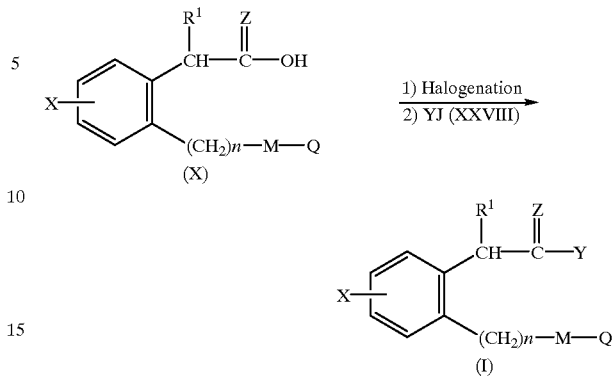

wherein J is a hydrogen atom or a metal salt, and the other symbols are as defined above.

The compound (I) of the present invention can be prepared by halogenating the compound (X) of the present invention, and then reacting the resulting compound with the compound (XXVIII).

Examples of the metal salt represented by J include alkaline metal salts (sodium salt, potassium salt, etc.), alkaline earth metal salts (magnesium salt, calcium salt, etc.), etc.

The halogenation is carried out, for example, by using a sulfonyl halide in an amount of 1 to 5 mol, preferably 1 to 2 mol, per mol of the compound (X) in the presence of a catalytic amount of a base such as N,N-dimethylformamide.

The sulfonyl halide includes, for example, sulfonyl chloride and sulfonyl bromide.

Examples of the solvent to be used include halogenated hydrocarbons such as methylene chloride, 1,2-dichloroethane, etc.; ethers such as diethyl ether, etc.; aromatic hydrocarbons such as toluene, etc.

The reaction temperature is appropriately selected from the range of room temperature to a reflux temperature of the solvent. The reaction time is 0.5 hour to 24 hours, preferably 1 to 5 hours.

The acid halide thus obtained can be used in the next step without purification.

The acid halide can be reacted with an alcohol, mercaptan, amine or its metal salt YJ (XXVIII) in the presence of a base to convert it to the compound (I).

Examples of the base include organic bases (e.g., triethylamine, N,N-dimethylaniline, pyridine, etc.) and inorganic bases (e.g., sodium carbonate, potassium carbonate, sodium hydride, etc.). The amount of the base to be used is 1 to 5 mol, preferably 1 to 2 mol, per mol of the acid halide.

Examples of the solvent to be used include halogenated hydrocarbons such as methylene chloride, 1,2-dichloroethane, etc.; ethers such as diethyl ether, etc.; aromatic hydrocarbons such as toluene, etc.; dimethyl sulfoxide, N,N-dimethylformamide, etc.

The reaction temperature is appropriately selected from the range of 0° C. to a reflux temperature of the solvent, and is preferably 0° C. to room temperature. The reaction time is 0.5 hour to 24 hours, preferably 0.5 to 2 hours.

The compound (I) of the present invention thus obtained can be separated and purified by known methods (e.g., chromatography, recrystallization, etc.).

METHOD M

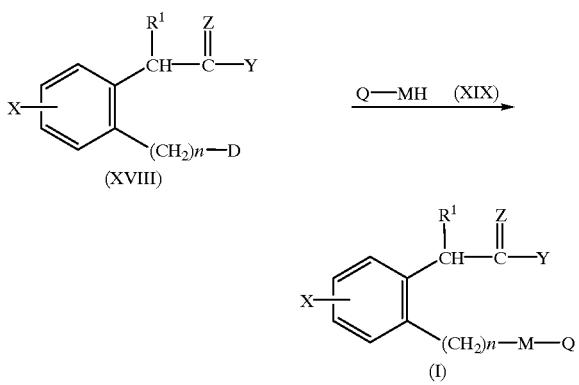

wherein D is a halogen atom, and the other symbols are as defined above.

The compound (I) of the present invention can be prepared by reacting the compound (XVIII) with the compound (XIX) in an appropriate solvent.

The halogen atom represented by D in the above formula includes, for example, fluorine, chlorine, bromine, and iodine.

The amount of the compound (XIX) to be used is 1 to 3 mol, preferably 1 to 1.5 mol, per mol of the compound (XVIII).

This reaction is preferably carried out in the presence of a base. Examples of the base include organic bases (e.g., alkoxides such as sodium methoxide, sodium ethoxide, potassium t-butoxide, etc.; amines such as pyridine, triethylamine, etc.), inorganic bases (e.g., metal hydroxides such as sodium hydroxide, potassium hydroxide, etc.; metal carbonates such as sodium carbonate, potassium carbonate, etc.; hydrides such as sodium hydride, potassium hydride, etc.), etc. The amount of the base to be used is 1 to 5 mol, preferably 1 to 2 mol, per mol of the compound (XVIII).

Examples of the solvent to be used include ethers such as diethyl ether, tetrahydrofuran, etc.; N,N-dimethylformamide, dimethyl sulfoxide, toluene, etc.

The reaction temperature is appropriately selected from the range of −20° C. to a reflux temperature of the solvent, and is preferably 0 to 50° C. The reaction time is 0.5 hour to 72 hours, preferably 0.5 to 10 hours.

The compound (I) of the present invention thus obtained can be separated and purified by known methods (e.g., chromatography, recrystallization, etc.).

METHOD N

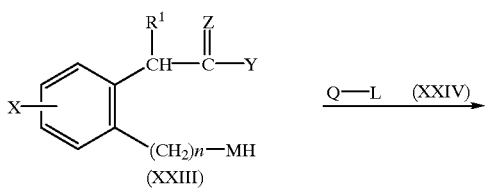

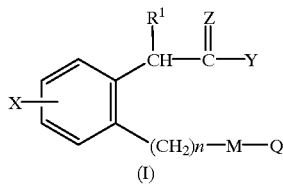

wherein L is a leaving group, and the other symbols are as defined above.

The compound (I) of the present invention can be prepared by reacting the compound (XXIII) with the compound (XXIV).

In the compound (XXIV), L is attached to any possible position in Q. Preferred examples of the compound (XXIV) include alkyl halides (e.g., methyl chloride, methyl bromide, methyl iodide, ethyl chloride, ethyl bromide, ethyl iodide, 1-iodopropane, 2-iodopropane, 1-iodobutane, chlorotrifluoromethane, 1,2-dibromoethane, chloromethyl ether, etc.); alkenyl halides (e.g., allyl bromide, etc.); alkynyl halides (e.g., propargyl bromide, etc.); acid halides (e.g., acetyl chloride, acetyl bromide, propionyl chloride, thioacetyl chloride, etc.); acid anhydrides (e.g., acetic anhydride, propionic anhydride, etc.); alkylsulfonyl halides (e.g., alkylsulfonyl chlorides such as methanesulfonyl chloride, ethanesulfonyl chloride, etc.); arylsulfonyl halides (e.g., arylsulfonyl chlorides such as benzenesulfonyl chloride, p-toluenesulfonyl chloride, etc.); N-unsubstituted or N-alkyl substituted carbamoyl halides (e.g., monoethylcarbamoyl chloride, dimethylcarbamoyl chloride, etc.); pyridine and its derivatives (e.g., 2,3-dichloropyridine, 2,5-dichloropyridine, 2-chloro-3-trifluoromethylpyridine, 2-chloro-5-trifluoromethylpyridine, 2-chloro-3-methylpyridne, 2,3,5-trichloropyridine, 2,3-dichloro-5-trifluoromethylpyridine, 2,5-dichloro-3-trifluoromethylpyridine, etc.); pyrimidine and its derivatives (e.g., 4,6-dichloropyrimidine, 2-chloro-4,6-dimethylpyrimidine, 4-chloro-5-ethoxycarbonyl-6-ethylpyrimidine, etc.); pyrazole and its derivatives (e.g., 5-chloro-4-formyl-1-methylpyrazole, 5-chloro-4-methoxycarbonyl-1,3-dimethylpyrazole, etc.); quinoline and its derivatives (e.g., 4-chloroquinoline, etc.); benzothiazole and its derivatives (e.g., 2-chlorobenzothiazole, etc.); quinazoline and its derivatives (e.g., 4-chloroquinazoline, etc.); benzene and its derivatives (e.g., 1-iodo-4-nitrobenzene, 1-bromo-4-trifluoromethylbenzene, etc.), etc.

For example, when Q is an optionally substituted aryl group, this reaction is carried out using the compound (XXIV) in an amount of 1 to 5 mol, preferably 1 to 2 mol, per mol of the compound (XXIII) in the presence of a base. Examples of the base include organic bases (e.g., triethylamine, N,N-dimethylaniline, pyridine, etc.), inorganic bases (e.g., sodium carbonate, potassium carbonate, sodium hydride, etc.), etc. The amount of the base to be used is 1 to 5 mol, preferably 1 to 2 mol, per mol of the compound (XXIII). Examples of the solvent include ethers such as tetrahydrofuran, etc.; aromatic hydrocarbons such as toluene, etc.; dimethyl sulfoxide; N,N-dimethylformamide; etc. The temperature is room temperature to 200° C., preferably 100 to 150° C., and the reaction time is 1 to 48 hours, preferably 2 to 24 hours.

For example, when Q is an optionally substituted heterocyclic group, this reaction is carried out using the compound (XXIV) in an amount of 1 to 5 mol, preferably 1 to 2 mol, per mol of the compound (XXIII) in the presence of a base. Examples of the base include organic bases (e.g., triethylamine, N,N-dimethylaniline, pyridine, etc.), inorganic bases (e.g., sodium carbonate, potassium carbonate, sodium hydride, etc.), etc. The amount of the base to be used is 1 to 5 mol, preferably 1 to 2 mol, per mol of the compound (XXIII). Examples of the solvent include ethers such as tetrahydrofuran, etc.; aromatic hydrocarbons such as toluene, etc.; dimethyl sulfoxide; N,N-dimethylformamide; etc. The reaction temperature is 0 to 150° C., preferably room temperature to 80° C. The reaction time is 0.5 to 48 hours, preferably 2 to 12 hours.

For example, when Q is alkyl, alkenyl or alkynyl each of which may be substituted, this reaction is carried out using the compound (XXIV) in an amount of 1 to 5 mol, preferably 1 to 2 mol, per mol of the compound (XXIII) in the presence of a base. Examples of the base include organic bases (e.g., sodium methoxide, sodium ethoxide, potassium t-butoxide, etc.), inorganic bases (e.g., sodium hydroxide, potassium hydroxide, sodium hydride, potassium hydride, etc.), etc. The amount of the base to be used is 1 to 5 mol, preferably 1 to 2 mol, per mol of the compound (I-1). Examples of the solvent include ethers such as diethyl ether, tetrahydrofuran, etc.; N,N-dimethylformamide, dimethyl sulfoxide, toluene, etc. The reaction temperature is appropriately selected from the range of −20° C. to a reflux temperature of the solvent, and is preferably 0 to 50° C. The reaction time is 0.5 hour to 48 hours, preferably 0.5 to 10 hours.

For example, when Q is a substituted carbonyl group, this reaction is carried out using the compound (XXIV) in an amount of 1 to 5 mol, preferably 1 to 2 mol, per mol of the compound (XXIII) in the presence of a base. Examples of the base include organic bases (e.g., triethylamine, N,N-dimethylaniline, pyridine, etc.) and inorganic bases (e.g., sodium hydroxide, potassium hydroxide, sodium hydride, etc.). The amount of the base to be used is 1 to 5 mol, preferably 1 to 2 mol, per mol of the compound (XXIII). Examples of the solvent to be used include halogenated hydrocarbons such as methylene chloride, chloroform, etc.; ethers such as diethyl ether, tetrahydrofuran, etc.; N,N-dimethylformamide, dimethyl sulfoxide, toluene, etc. The reaction temperature is appropriately selected from the range of −20° C. to a reflux temperature of the solvent, and is preferably 0 to 70° C., more preferably 20 to 50° C. The reaction time is 0.5 hour to 48 hours, preferably 0.5 to 12 hours, more preferably 0.5 to 5 hours.

For example, when Q is a substituted sulfonyl group, this reaction is carried out using the compound (XXIV) in an amount of 1 to 5 mol, preferably 1 to 2 mol, per mol of the compound (XXIII) in the presence of a base. Examples of the base include organic bases (e.g., triethylamine, N,N-dimethylaniline, pyridine, etc.) and inorganic bases (e.g., sodium carbonate, potassium carbonate, sodium hydride, etc.). The amount of the base to be used is 1 to 5 mol, preferably 1 to 2 mol, per mol of the compound (XXIII). Examples of the solvent to be used include halogenated hydrocarbons such as methylene chloride, chloroform, etc.; ethers such as diethyl ether, tetrahydrofuran, etc.; N,N-dimethylformamide, dimethyl sulfoxide, toluene, etc. The reaction temperature is appropriately selected from the range of −20° C. to a reflux temperature of the solvent, and is preferably 0 to 50° C. The reaction time is 0.5 hour to 24 hours, preferably 0.5 to 5 hours.

The compound (I) of the present invention thus obtained can be separated and purified by known methods (e.g., chromatography, recrystallization, etc.).

METHOD O

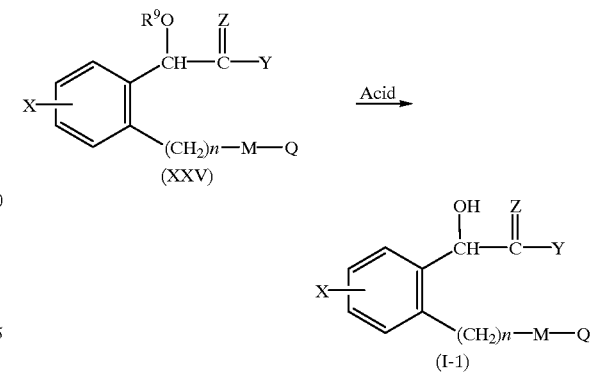

wherein $R^9$ is tetrahydropyranyl.

The compound (I-1) of the present invention can be prepared by treating the compound (XXV) with an acid.

The tetrahydropyranyl represented by $R^9$ includes, for example, 2-tetrahydropyranyl, etc.

The compound (I-1) of the present invention can be prepared by treating the compound (XXV) with an acid in an appropriate solvent.

Examples of the acid to be used in this reaction include mineral acids such as hydrochloric acid, hydrobromic acid, nitric acid, sulfuric acid, etc.; sulfonic acids such as p-toluenesulfonic acid, etc.; acid-base pairs such as pyridinium p-toluenesulfonate, etc.; etc. The amount of the acid to be used is 0.01 to 0.5 mol, preferably 0.05 to 0.2 mol, per mol of the compound (XXV).

Examples of the solvent to be used include alcohols such as methanol, ethanol, etc.; aromatic hydrocarbons such as toluene, xylene, etc.; halogenated hydrocarbons such as methylene chloride, chloroform, etc.; ethers such as ether, tetrahydrofuran, etc.; and water. These solvents can be used alone or as a mixture thereof.

The reaction temperature is appropriately selected from the range of 0° C. to a reflux temperature of the solvent, and is preferably 20° C. to 80° C. The reaction time is 0.5 hour to 48 hours, preferably 0.5 to 12 hours.

The compound (I-1) of the present invention thus obtained can be separated and purified by known methods (e.g., chromatography, recrystallization, etc.).

METHOD P

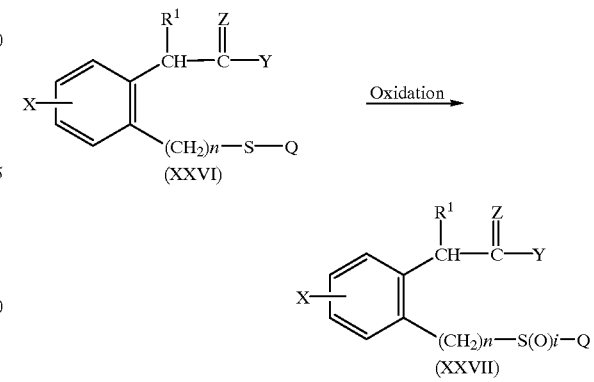

wherein each symbol is as defined above.

The compound (XXVII) of the present invention can be prepared by oxidizing the compound (XXVI) of the present invention. Examples of the oxidizing agent to be used in the oxidation include peracids such as hydrogen peroxide, peracetic acid, perbenzoic acid, m-chloroperbenzoic acid, etc., sodium metaperiodate, hydroperoxide, etc. The amount of the oxidizing agent to be used is 1 to 10 mol, preferably 1 to 3 mol, per mol of the compound (XXVI).

Examples of the solvent to be used include aromatic hydrocarbons such as toluene, xylene, etc.; halogenated hydrocarbons such as methylene chloride, chloroform, etc.; ethers such as ether, tetrahydrofuran, etc.; alcohols such as methanol, ethanol, etc.; and water. These solvents can be used alone or as a mixture thereof.

The reaction temperature is appropriately selected from the range of −20° C. to a reflux temperature of the solvent, and is preferably 0° C. to 50° C. The reaction time is 0.5 hour to 48 hours, preferably 0.5 to 12 hours.

The compound (XXVII) of the present invention thus obtained can be separated and purified by known methods (e.g., chromatography, recrystallization, etc.).

The following are processes for producing compounds used as the starting material in the above production of the compounds of the present invention.

The compound (II) which can be used as the starting material in the reaction of Method A can preferably be prepared by Method Q described below.

METHOD O

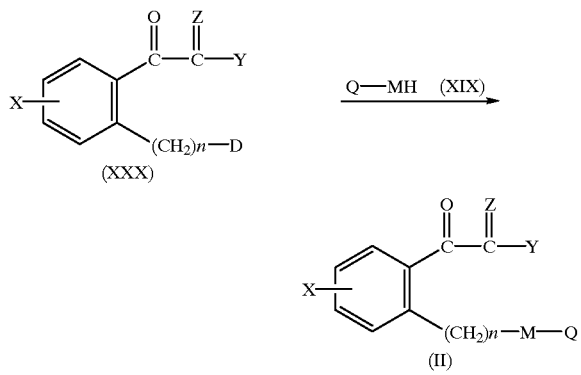

wherein each symbol is as defined above.

The compound (II) can be prepared by reacting the compound (XXX) with the compound (XIX) in an appropriate solvent in the presence of a base.

The amount of the compound (XIX) to be used is 1 to 3 mol, preferably 1 to 1.5 mol, per mol of the compound (XXX).

Examples of the base include organic bases (e.g., alkoxides such as sodium methoxide, sodium ethoxide, potassium t-butoxide, etc.; amines such as pyridine, triethylamine, etc.), inorganic bases (e.g., metal hydroxides such as sodium hydroxide, potassium hydroxide, etc.; metal carbonates such as sodium carbonate, potassium carbonate, etc.; hydrides such as sodium hydride, potassium hydride, etc.), etc. The amount of the base to be used is 1 to 5 mol, preferably 1 to 2 mol, per mol of the compound (XXX).

Examples of the solvent to be used include ethers such as diethyl ether, tetrahydrofuran, etc.; N,N-dimethylformamide, dimethyl sulfoxide, toluene, etc.

The reaction temperature is appropriately selected from the range of −20° C. to a reflux temperature of the solvent, and is preferably 0 to 50° C. The reaction time is 0.5 hour to 48 hours, preferably 0.5 to 10 hours.

The compound (II) thus obtained can be used in the next step as the reaction mixture or the crude product, or after separating and purifying it by known methods (e.g., chromatography, recrystallization, etc.).

The compound (XXX) used as the starting material in this reaction can be obtained by halogenating the corresponding alkylphenyl compound according to JP-A 2-3651 or JP-A 2-164866.

The compound (XIV) which can be used as the starting material in the reaction of Method H can preferably be prepared by Method R described below.

METHOD R

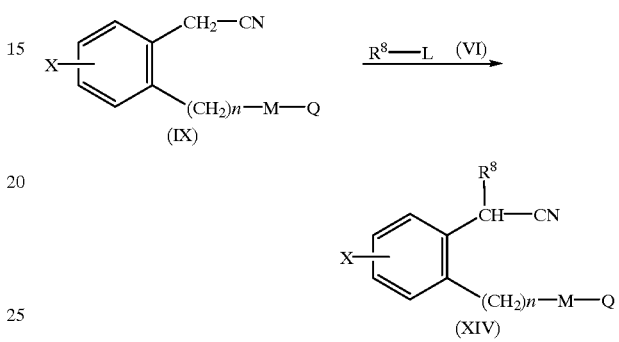

wherein $R^8$ is alkyl, haloalkyl or alkoxyalkyl, and the other symbols are as defined above.

The compound (XIV) can be obtained by reacting the compound (IX) with the compound (VI).

The groups represented by $R^8$ include, for example, the above corresponding groups represented by $R^1$.

Examples of the compound (VI) include methyl chloride, methyl bromide, methyl iodide, ethyl chloride, ethyl bromide, ethyl iodide, 1-iodopropane, 2-iodopropane, 1-iodobutane, chlorotrifluoromethane, 1,2-dibromoethane, chloromethyl ether, etc. The amount of the compound (VI) to be used is 1 to 5 mol. preferably 1 to 2 mol, per mol of the compound (IX).

Normally, this reaction is carried out in the presence of a base. Examples of the base include organic bases (e.g., butyllithium, sodium ethoxide, etc.) and inorganic bases (e.g., sodium hydroxide, potassium hydroxide, sodium amide, sodium hydride, etc.). The amount of the base to be used is 1 to 5 mol, preferably 1 to 2 mol, per mol of the compound (IX).

Examples of the solvent to be used include aromatic hydrocarbons such as toluene, xylene, etc.; halogenated hydrocarbons such as methylene chloride, chloroform, etc.; ethers such as ether, tetrahydrofuran, etc.; alcohols such as methanol, ethanol, etc.; N,N-dimethylformamide, dimethyl sulfoxide, etc.

The reaction temperature is appropriately selected from the range of −80° C. to a reflux temperature of the solvent, and is preferably 0° C. to 80° C. The reaction time is 0.5 hour to 48 hours, preferably 0.5 to 6 hours.

The compound (XIV) thus obtained can be separated and purified by known methods (e.g., chromatography, recrystallization, etc.).

The compound (XXXIX) included in the compound (XVIII) which can be used as the starting material in the reaction of Method M can preferably be prepared by Method S described below.

METHOD S

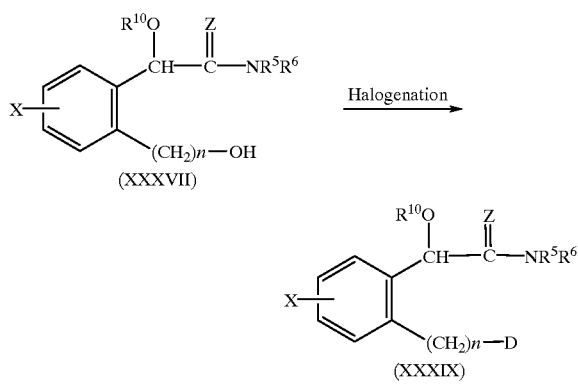

wherein $R^5$ is a hydrogen atom or alkyl, $R^6$ is a hydrogen atom, alkyl or hydroxylalkyl, $R^{10}$ is optionally substituted alkyl, optionally substituted alkenyl or optionally substituted alkynyl, and the other symbols are as defined above.

The compound (XXXIX) can be prepared by halogenating the compound (XXXVII) in an appropriate solvent.

The alkyl, alkenyl and alkynyl represented by $R^{10}$ include the above alkyl, alkenyl and alkynyl as the substituents of the optionally substituted hydroxyl represented by $R^1$, respectively.

The halogenating agent to be used in this reaction includes, for example, chlorinating agents such as thionyl chloride, phosphorus oxychloride, phosphorus pentachloride, carbon tetrachloride-triphenylphosphine, etc.; and brominating agents such as thionyl bromide, phosphorus oxybromide, carbon tetrabromide-triphenylphosphine, etc. The amount of the halogenating agent to be used is 1 to 5 mol, preferably 1 to 2 mol, per mol of the compound (XXXVII).

Examples of the solvent to be used include aromatic hydrocarbons such as toluene, xylene, etc.; halogenated hydrocarbons such as methylene chloride, chloroform, etc.; ethers such as ether, tetrahydrofuran, etc.

The reaction temperature is appropriately selected from the range of 0° C. to a reflux temperature of the solvent, and is preferably 20° C. to 80° C. The reaction time is 0.5 hour to 48 hours, preferably 0.5 to 12 hours.

The compound (XXXIX) thus obtained can be used in the next step as the reaction mixture or the crude product, or after separating and purifying it by known methods (e.g., chromatography, recrystallization, etc.).

The compound (XXXVII) which can be used as the starting material in this reaction can preferably be prepared by Method T described below.

METHOD T

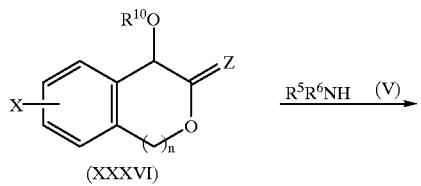

-continued

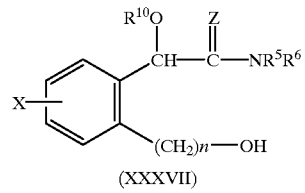

wherein each symbol is as defined above.

The compound (XXXVII) can be prepared by reacting the compound (XXXVI) with the compound (V) in an appropriate solvent.

Preferred examples of the compound (V) include liquid ammonia; primary amines such as methylamine, ethylamine, etc.; and secondary amines such as dimethylamine, diethylamine, etc. The amount of the compound (V) to be used is 1 to 5 mol, preferably 1 to 2 mol, per mol of the compound (XXXVI).

Examples of the solvent to be used include alcohols such as methanol, ethanol, etc.; aromatic hydrocarbons such as toluene, xylene, etc.; halogenated hydrocarbons such as methylene chloride, chloroform, etc.; ethers such as ether, tetrahydrofuran, etc.; and water. These solvents can be used alone or as a mixture thereof.

The reaction temperature is appropriately selected from the range of 0° C. to a reflux temperature of the solvent, and is preferably 20° C. to 80° C. The reaction time is 0.5 hour to 48 hours, preferably 0.5 to 12 hours.

The compound (XXXVII) thus obtained can be used in the next step as the reaction mixture or the crude product, or after separating and purifying it by known methods (e.g., chromatography, recrystallization, etc.).

The compound (XXXVI) which can be used as the starting material in this reaction can preferably be prepared by Method U described below.

METHOD U

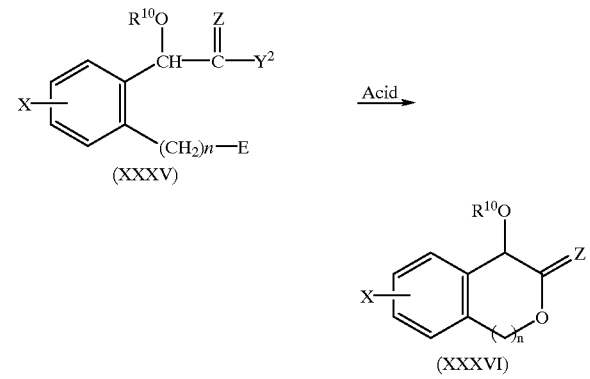

wherein $Y^2$ is alkoxy, E is a protected hydroxyl group, and the other symbols are as defined above.

The compound (XXXVI) can be prepared by treating the compound (XXXV) with an acid in an appropriate solvent.

The alkoxy represented by $Y^2$ in the above formula includes the above alkoxy represented by Y.

The protective group of the protected hydroxyl represented by E include conventional protective groups for hydroxyl such as ether-type protective groups, acetal-type protective groups, etc., described in, for example, T. W. Green, "Protective Groups in Organic Synthesis" p. 1–113, John Willy & Sons (1981); C. B. Reese, "Protective Groups in Organic Chemistry", J. F. McOmie (ed.), p. 95–143, Plenum Press (1973), etc.

Examples of the ether-type protective groups include alkyl (e.g., $C_{1-6}$ alkyl, preferably $C_{1-4}$ alkyl, such as methyl, ethyl, propyl, t-butyl, etc.), alkenyl (e.g., $C_{2-6}$ alkenyl, preferably $C_{2-4}$ alkenyl, such as allyl, etc.), aralkyl (e.g., substituted or unsubstituted $C_6$tho aryl-$C_{1-4}$ alkyl such as benzyl, p-methoxybenzyl, triphenyl(ethyl, etc.), trialkylsilyl (e.g., tri-$C_{1-6}$ alkylsilyl such as triisopropylsilyl, t-butyldimethylsilyl, etc.), alkyldiarylsilyl (e.g., $C_{1-6}$ alkyl di-$C_{6-10}$ arylsilyl such as t-butyldiphenylsilyl, etc.), triaralkylsilyl (e.g., tribenzylsilyl, etc.), etc.

Examples of the acetal-type protective groups include alkoxyalkyl (e.g., $C_{1-4}$ alkoxy-$C_{1-4}$ alkyl such as methoxymethyl, 1-ethoxyethyl, 1-methyl-1-methoxyethyl, etc.), alkoxyalkoxyalkyl (eg., $C_{1-4}$ alkoxy-$C_{1-4}$ alkoxy-C1-4 alkyl such as methoxyethoxymethyl, etc.), alkylthioalkyl (e.g., C1-4 alkylthio-$C_{1-4}$ alkyl such as methylthiomethyl, etc.), tetrahydropyranyl (e.g., tetrahydropyran-2-yl, 4-methoxytetrahydropyran-4-yl, etc.), tetrahydrothiopyranyl (e.g., tetrahydrothiopyran-2-yl, etc.), tetrahydrofuranyl (e.g., tetrahydrofuran-2-yl, etc.), tetrahydrothiofuranyl (e.g., tetrahydrothiofuran-2-yl, etc.), aralkyloxyalkyl (e.g., benzyloxymethyl, etc.), etc.

Of them, protective groups removable by acid treatment are preferred. In particular, tetrahydropyranyl (in this case, E is tetrahydropyranyloxy) and 1-ethoxyethyl (in this case, E is 1-ethoxyethoxy) are preferred, and tetrahydro-pyran-2-yl (in this case, E is 2-tetrahydropyranyloxy) is particularly preferred.

Examples of the acid to be used in this reaction include mineral acids such as hydrochloric acid, hydrobromic acid, nitric acid, sulfuric acid, etc.; sulfonic acids such as p-toluenesulfonic acid, etc.; acid-base pairs such as pyridinium p-toluenesulfonate, etc.; etc. The amount of the acid to be used is 0.01 to 0.5 mol, preferably 0.05 to 0.2 mol, per mol of the compound (XXXV).

Examples of the solvent to be used include alcohols such as methanol, ethanol, etc.; aromatic hydrocarbons such as toluene, xylene, etc.; halogenated hydrocarbons such as methylene chloride, chloroform, etc.; ethers such as ether, tetrahydrofuran, etc.; and water. These solvents can be used alone or as a mixture thereof.

The reaction temperature is appropriately selected from the range of 0° C. to a reflux temperature of the solvent, and is preferably 20° C. to 80° C. The reaction time is 0.5 hour to 48 hours, preferably 0.5 to 12 hours.

The compound (XXXVI) thus obtained can be used in the next step as the reaction mixture or the crude product, or separating and purifying it by known methods (e.g., chromatography, recrystallization, etc.).

The compound (XXXV) which can be used as the starting material in this reaction can preferably be prepared by Method V described below.

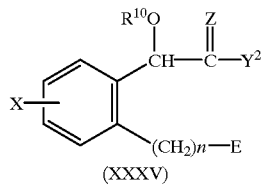

(XXXV)

wherein L is a leaving group, and the other symbols are as defined above.

The compound (XXXV) can be prepared by reacting the compound (XXXII) with the compound (XXXIV) in an appropriate solvent in the presence of a base.

The leaving group represented by L in the above formula includes, for example, halogen atoms (e.g., chlorine, bromine, iodine, etc.), alkylsulfonyloxy (e.g., methanesulfonyloxy, etc.), arylsulfonyloxy, (e.g., p-toluenesulfonyloxy, etc.), etc.

Preferred examples of the compound (XXXIV) used in this reaction include alkyl halides (e.g., methyl chloride, methyl bromide, methyl iodide, ethyl chloride, ethyl bromide, ethyl iodide, 1-iodopropane, 2-iodopropane, 1-iodobutane, chlorotrifluoromethane, 1,2-dibromoethane, chloromethyl ether, etc.), alkenyl halides (e.g., allyl bromide, etc.), alkynyl halides (e.g., propargyl bromide, etc.), etc. The amount of the compound (XXXIV) to be used is 1 to 5 mol, preferably 1 to 2 mol, per mol of the compound (XXXII).

Examples of the base include organic bases (e.g., alkoxides such as sodium methoxide, sodium ethoxide, potassium t-butoxide, etc.), inorganic bases (e.g., metal hydroxides such as sodium hydroxide, potassium hydroxide, etc.; hydrides such as sodium hydride, potassium hydride, etc.), etc. The amount of the base to be used is 1 to 5 mol, preferably 1 to 2 mol, per mol of the compound (XXXII).

Examples of the solvent to be used include ethers such as diethyl ether, tetrahydrofuran, etc.; N,N-dimethylformamide, dimethyl sulfoxide, toluene, etc.

The reaction temperature is appropriately selected from the range of –20° C. to a reflux temperature of the solvent, and is preferably 0 to 50° C. The reaction time is 0.5 hour to 48 hours, preferably 0.5 to 10 hours.

The compound (XXXV) thus obtained can be used in the next step as the reaction mixture or the crude product, or after separating and purifying it by known methods (e.g., chromatography, recrystallization, etc.).

The compound (XXXII) which can be used as the starting material in this reaction can preferably be prepared by Method W described below.

METHOD V

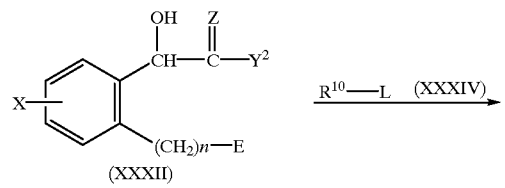

METHOD W

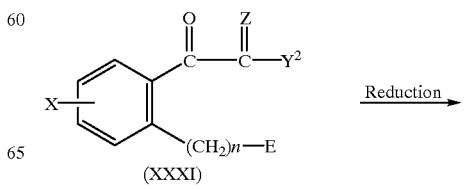

-continued $$\underset{(XXXII)}{\underset{(CH_2)_n-E}{X-\text{[benzene ring with CH(OH)-C(=Z)-Y}^2\text{ and }(CH_2)_n-E\text{]}}}$$

wherein each symbol is as defined above.

The compound (XXXII) can be prepared by reducing the compound (XXXI) in an appropriate solvent.

The reducing agent to be used is a conventional reducing agent for reduction of ketones, such as metal hydrides, metal hydride complex compounds, etc. Examples of the reducing agent include three-coordinate boranes (e.g., borane, etc.), four-coordinate borates (e.g., sodium borohydride, lithium borohydride, etc.), three-coordinate aluminiums (e.g., diisobutylaluminum hydride, etc.), four-coordinate aluminate complexes (e.g., lithium aluminum hydride, etc.), etc. The amount of the reducing agent to be used is 0.25 to 3 mol, preferably 1.0 to 1.2 mol, per mol of the compound (XXXI).

Examples of the solvent include alcohols such as methanol, ethanol, etc.; ethers such as diethyl ether, tetrahydofuran, etc.; water, etc. These solvents can be used alone or as a mixture thereof.

The reaction temperature is appropriately selected from the range of −20° C. to a reflux temperature of the solvent, and is preferably 0 to 50° C. The reaction time is 0.5 hour to 24 hours, preferably 0.5 to 2 hours.

The compound (XXXII) thus obtained can be used in the next step as the reaction mixture or the crude product, or after separating and purifying it by known methods (e.g., chromatography, recrystallization, etc.).

The compound (XXXI) used as the starting material in this reaction can be obtained by reacting a Grignard compound of 2-(substituted methyl)-1-bromobenzene with a dialkyl oxalate according to Journal of Organic Chemistry, USSR, Vol. 5, p. 1530 (1969).

The compound (XXXXI) included in the compound (XVIII) which can be used as the starting material in Method M can be prepared by Method X described below.

METHOD X $$\underset{(XXX)}{\text{[benzene with C(=O)-C(=Z)-Y and }(CH_2)_n-D, X\text{]}} \xrightarrow{\text{Reduction}}$$

$$\underset{(XXXXI)}{\text{[benzene with CH(OH)-C(=Z)-Y and }(CH_2)_n-D, X\text{]}}$$

wherein each symbol is as defined above.

The compound (XXXXI) can be prepared by reducing the compound (XXX) in an appropriate solvent.

The reducing agent to be used is a conventional reducing agent for reduction of ketones, such as metal hydrides, metal hydride complex compounds, etc. Examples of the reducing agent include three-coordinate boranes (e.g., borane, etc.), four-coordinate borates (e.g., sodium borohydride, lithium borohydride, etc.), three-coordinate aluminiums (e.g., diisobutylaluminum hydride, etc.), four-coordinate aluminate complexes (e.g., lithium aluminum hydride, etc.), etc. The amount of the reducing agent to be used is 0.25 to 3 mol, preferably 1.0 to 1.2 mol, per mol of the compound (XXX).

Examples of the solvent include alcohols such as methanol, ethanol, etc.; ethers such as diethyl ether, tetrahydofuran, etc.; water, etc. These solvents can be used alone or as a mixture thereof.

The reaction temperature is appropriately selected from the range of −20° C. to a reflux temperature of the solvent, and is preferably 0 to 50° C. The reaction time is 0.5 hour to 24 hours, preferably 0.5 to 2 hours.

The compound (XXXXI) thus obtained can be used in the next step as the reaction mixture or the crude product, or after separating and purifying it by known methods (e.g., chromatography, recrystallization, etc.).

The compound (XXXXIII) included in the compound (XVIII) which can be used as the starting material in Method M can preferably be prepared by Method Y described below.

METHOD Y $$\underset{(XXXXI)}{\text{[benzene with CH(OH)-C(=Z)-Y and }(CH_2)_n-D, X\text{]}} \xrightarrow{\text{Introduction of tetrahydropyranyl}}$$

$$\underset{(XXXXIII)}{\text{[benzene with CH(OR}^9\text{)-C(=Z)-Y and }(CH_2)_n-D, X\text{]}}$$

where in $R^9$ is tetrahydropyranyl, and the other symbols are as defined above.

The compound (XXXXIII) can be prepared by introducing tetrahydropyranyl into the compound (XXXXI).

The tetrahydropyranyl represented by $R^9$ includes, for example, 2-tetrahydropyranyl, etc.

The tetrahydropyranyl can be introduced by a conventional method for protecting hydroxyl with tetrahydropyranyl, for example, by reacting the compound (XXXXI) with dihydropyran in an appropriate solvent in the presence of an acid.

Examples of the acid include p-toluenesulfonic acid, hydrochloric acid, phosphorus oxychloride, acid-base pairs such as pyridinium p-toluenesulfonate, etc. The amount of the acid to be used is 0.01 to 0.5 mol, preferably 0.05 to 0.2 mol, per mol of the compound (XXXXI).

Examples of the solvent to be used include aromatic hydrocarbons such as toluene, xylene, etc.; halogenated hydrocarbons such as methylene chloride, chloroform, etc.; ethers such as ether, tetrahydrofuran, etc. These solvents can be used alone or as a mixture thereof.

The reaction temperature is appropriately selected from the range of 0° C. to a reflux temperature of the solvent, and is preferably 20° C. to 80° C. The reaction time is 0.5 hour to 48 hours, preferably 0.5 to 12 hours.

The compound (XXXXIII) thus obtained can be used in the next step as the reaction mixture or the crude product, or separating and purifying it by known methods (e.g., chromatography, recrystallization, etc.).

The compound (XXXXI) which can be used as the starting material in this reaction can preferably be prepared by Method X described above.

The compound (XXXXV) included in the compound (XXIII) which can be used as the starting material in Method N can be prepared by Method Z described below.

METHOD Z

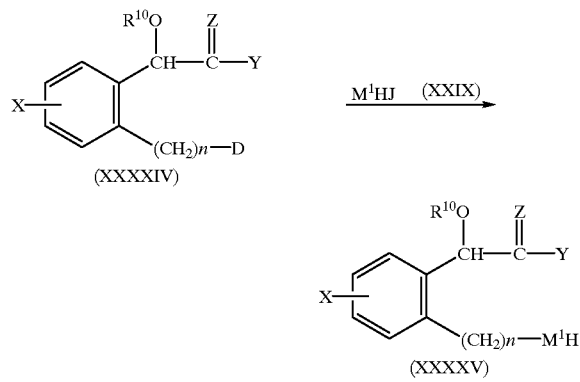

wherein $R_{10}$ is optionally substituted alkyl, optionally substituted alkenyl or optionally substituted alkynyl, D is a halogen atom, $M^1$ is a sulfur atom or $NR^2$ ($R^2$ is a hydrogen atom, alkyl or acyl), and the other symbols are as defined above.

The compound (XXXXV) can be prepared by reacting the compound (XXXXIV) with the compound (XXIX).

The compound (XXIX) may be in the form of a metal salt. Examples of the metal salt include alkaline metal salts (sodium salt, potassium salt, etc.), alkaline earth metal salts (magnesium salt, calcium salt, etc.), etc.

When a metal salt of a mercaptan such as hydrogen sulfide (e.g., sodium hydrosulfide, potassium hydrosulfide) is used as the compound (XXIX), the amount of it to be used is 1 to 5 mol, preferably 1 to 2 mol, per mol of the compound (XXXXIV). Examples of the solvent include alcohols such as methanol, ethanol, etc.; halogenated hydrocarbons such as methylene chloride, 1,2-dichloroethane, etc.; ethers such as diethyl ether, etc.; aromatic hydrocarbons such as toluene, etc., dimethyl sulfoxide, N,N-dimethylformamide, etc. The reaction temperature is appropriately selected from the range of 0° C. to a reflux temperature of the solvent, preferably room temperature to a reflux temperature of the solvent. The reaction time is 0.5 hour to 24 hours, preferably 1 to 5 hours.

When an amine or a metal salt of an amine (e.g., sodium amide, etc.) is used as the compound (XXIX), the amount of it to be used is 1 to 5 mol, preferably 1 to 2 mol, per mol of the compound (XXXXIV). Examples of the solvent include alcohols such as methanol, ethanol, etc.; halogenated hydrocarbons such as methylene chloride, 1,2-dichloroethane, etc.; ethers such as diethyl ether, etc.; aromatic hydrocarbons such as toluene, etc., dimethyl sulfoxide, N,N-dimethylformamide, etc.

The reaction temperature is appropriately selected from the range of 0° C. to a reflux temperature of the solvent, and is preferably 0° C. to room temperature. The reaction time is 0.5 hour to 24 hours, preferably 1 to 5 hours.

The compound (XXXXV) thus obtained can be used in the next step as the reaction mixture or the crude product, or after separating and purifying it by known methods (e.g., chromatography, recrystallization, etc.).

The compound of the formula (I) of the present invention is effective against a wide variety of phytopathogenic fungi on crop plants (e.g., rice, wheat, barley, rye, corn, common millet, millet, buckwheat, soybean, redbean, peanut, etc.), fruit trees (e.g., citrus fruits, grape, apple, pear, peach, etc.), vegetables (e.g., cucumber, eggplant, tomato, pumpkin, kidney bean, etc.), etc., or seeds thereof. It is also effective against phytopathogenic fungi in soil. The compound of the present invention shows potent fungicidal activity particularly against *Pyricularia oryzae, Rhizoctonia solani, Erysiphe araminis, Sphaerotheca fuliginea, Erysiphe cichoracearum, Phylophthora infestans, Pseudoperonospora cubensis, Peronospora manshurica, Plasaopara viticola, Botrytis cinerea* of vegetables, grape, etc., *Pythium aphanidermatum, Sclerotinia sclerotiorum* of buckwheat, soybean, colza, etc., *Corticium rolfsii* of soybean, redbean, potato, peanut, etc., *Pseudocercosporella herpotrichoides, Puccinia coronata*, etc. Therefore, the compound (I) of the present invention is useful as agricultural fungicides.

Application of the compound (I) of the present invention may be made to plants by any conventional procedure such as atomizing, scattering or spreading of the active compound. Application may also be made by treating with the active compound seeds of plants, soil where plants grow, soil for seeding, paddy field or water for perfusion. Application may be performed before or after the infection with phytopathogenic fungi on plants.

The compound can be used in a conventional formulation form suitable for agricultural fungicides such as solutions, wettable powders, emulsions, suspensions, concentrated liquid preparations, tablets, granules, aerosols, powders, pastes, dusts, etc.

Such formulation form can be prepared in a conventional manner by mixing at least one compound of the present invention with an appropriate solid or liquid carrier(s) and, if necessary, an appropriate adjuvant(s) (e.g., surfactants, spreaders, dispersants, stabilizers, etc.) for improving the dispersibility and other properties of the active compound.

Examples of the solid carriers or diluents include botanical materials (e.g., flour, tobacco stalk powder, soybean powder, walnut-shell powder, vegetable powder, saw dust, bran, bark powder, cellulose powder, vegetable extract residue, etc.), fibrous materials (e.g., paper, corrugated cardboard, old rags, etc.), artificial plastic powders, clays (e.g., kaolin, bentonite, fuller's earth, etc.), talc, other inorganic materials (e.g., pyrophyllite, sericite, pumice, sulfur powder, active carbon, etc.), chemical fertilizers (e.g., ammonium sulfate, ammonium phosphate, ammonium nitrate, urea, ammonium chloride, etc.), etc.

Examples of the liquid carriers or diluents include water, alcohols (e.g., methanol, ethanol, etc.), ketones (e.g., acetone, methyl ethyl ketone, etc.), ethers (e.g., diethyl ether, dioxane, cellosolve, tetrahydrofuran, etc.), aromatic hydrocarbons (e.g., benzene, toluene, xylene, methylnaphthalene, etc.), aliphatic hydrocarbons (e.g., gasoline, kerosene, lamp oil, etc.), esters, nitrites, acid amides (e.g., dimethylformamide, dimethylacetamide, etc.), halogenated hydrocarbons (e.g., dichloroethane, carbon tetrachloride, etc.), etc.

Examples of the surfactants include alkyl sulfates, alkyl sulfonates, alkylaryl sulfonates, polyethylene glycol ethers, polyhydric alcohol esters, etc.

Examples of the spreaders or dispersants include casein, gelatin, starch powder, carboxymethyl cellulose, gum arabic, alginic acid, lignin, bentonite, molasses, polyvinyl alcohol, pine oil, agar, etc.

Examples of the stabilizers include PAP (a mixture of isopropylphosphate), tricresyl phosphate (TCP), tolu oil, epoxidized oil, surfactants, fatty acids and their esters, etc.

The composition of the present invention may contain other fungicides, insecticides, herbicides or fertilizers in addition to the above ingredients.

In general, the above composition contains at least one compound of the formula (I) of the present invention in a concentration of 1 to 95% by weight, preferably 2.0 to 80% by weight. The composition can be used as such or in a diluted form. About 1.0 g to 5 kg/hectare, preferably about 2 g to 100 g/hectare, of the compound of the present invention is used in a concentration of normally about 1 to 50,000 ppm, preferably about 100 to 5,000 ppm.

EXAMPLES

The following examples and test examples further illustrate the present invention in detail, but are not to be construed to limit the scope thereof. The coupling constants (J) are indicated in hertz (Hz).

Example 1

Synthesis of 2-hydroxy-2-(2-phenoxyphenyl) acetamide (Compound No. 2)

2-Oxo-2-(2-phenoxyphenyl)acetamide (4.82 g, 20.0 mmol) was dissolved in ethanol (50 ml). Sodium borohydride (0.76 g, 20.0 mmol) was added slowly under ice-cooling. After stirring for 30 minutes, the mixture was neutralized with 1N hydrochloric acid, and extracted with ethyl acetate. The organic layer was washed with saturated brine and dried over sodium sulfate, and the solvent was evaporated to give an oil. The oil was purified by column chromatography on silica gel (eluting with n-hexane-ethyl acetate) to give the desired compound 2-hydroxy-2-(2-phenoxyphenyl)acetamide (4.3 g, 89%) as colorless crystals. The compound was recrystallized from a mixed solvent of n-hexane-methylene chloride to give colorless crystals.

mp.: 121–122° C.

NMR (δ ppm TMS/CDCl$_3$): 4.11(1H,brs), 5.46(1H,s), 5.57(1H,brs), 6.58(1H,brs), 6.88(1H,dd,J=7.9,1.2), 7.03 (2H,dd,J=7.9,1.2), 7.13–7.20(2H,m), 7.23–7.27(1H,m), 7.29–7.40(2H,m), 7.58(1H,dd,J=7.9,1.2).

Example 2

Synthesis of 2-[2-(2,5-dimethylphenoxymethyl) phenyl]-2-hydroxy-N-methylacetamide (Compound No. 75)

2-[2-(2,5-Dimethylphenoxymethyl)phenyl]-N-methyl-2-oxoacetamide (0.93 g, 3.1 mmol) was dissolved in methanol (10 ml). Sodium borohydride (0.06 g, 1.6 mmol) was added slowly under ice-cooling. After stirring for 30 minutes, the mixture was neutralized with 1N hydrochloric acid, and extracted with ethyl acetate. The organic layer was washed with saturated brine and dried over sodium sulfate, and the solvent was evaporated to give an oil. The oil was purified by column chromatography on silica gel (eluting with n-hexane-ethyl acetate) to give the desired compound 2-[2-(2,5-dimethylphenoxymethyl)phenyl]-2-hydroxy-N-methylacetamide (0.85 g, 91%) as white crystals.

mp.: 86–87° C.

NMR (δ ppm TMS/CDCl$_3$): 2.16(3H,s), 2.35(3H,s), 2.78 (3H,d,J=4.9), 4.35(1H,d,J=3.7), 4.94(1H,d,J=11.0), 5.34 (1H,d,J=11.0), 5.35(1H,d,J=3.7), 6.49(1H,brs), 6.78 (1H,d,J=7.3), 6.87(1H,s), 7.06(1H,d,J=7.3), 7.32–7.48(4H,m).

Example 3

According to the same manner as that described in Example 1 or 2, the compounds of the formula (I-7) were synthesized. The compounds thus obtained and the physical data of their representative compounds are as follows.

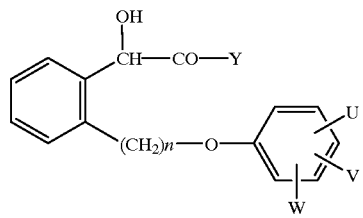

(1-7)

| Comp. No. | (CH$_2$)$_n$—O—[ring with U,V,W] | Y | Property | mp or $^1$H-NMR(CDCl$_3$) δ ppm |
|---|---|---|---|---|
| 1 | —O—[phenyl] | NHCH$_3$ | crystal | 99.0–99.5° C. |
| 2 | —O—[phenyl] | NH$_2$ | crystal | 121–122° C. |

-continued
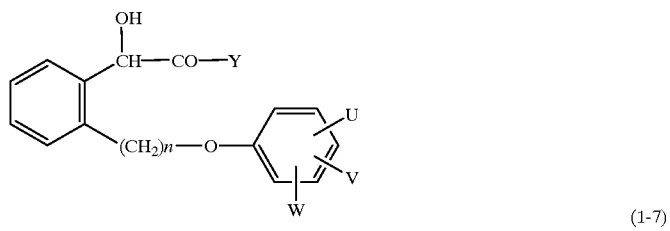
(1-7)
| Comp. No. | W | Y | Property | mp or $^1$H-NMR(CDCl$_3$) δ ppm |
|---|---|---|---|---|
| 3 | —O—C$_6$H$_5$ | N(CH$_3$)$_2$ | crystal | 127~128° C. |
| 4 | —O—C$_6$H$_5$ | NHCH$_2$OH | crystal | 94.5~95.5° C. |
| 5 | —O—(2-CH$_3$-C$_6$H$_4$) | NHCH$_3$ | | |
| 6 | —O—(3-CH$_3$-C$_6$H$_4$) | NH$_2$ | | |
| 7 | —O—(3-CH$_3$-C$_6$H$_4$) | NHCH$_3$ | oil | 2.34(3H, s), 2.81(3H, d, J=4.9), 4.20(1H, br), 5.40 (1H, s), 6.4 (1H, brs), 6.80–6.88(3H, m), 6.96(1H, d, J=7.3), 7.13–7.28(3H, m), 7.55(1H, dd, J=7.3, 1.8). |
| 8 | —O—(3-CH$_3$-C$_6$H$_4$) | NHCH$_2$OH | | |
| 9 | —O—(3-CH$_3$-C$_6$H$_4$) | N(CH$_3$)$_2$ | | |
| 10 | —O—(4-CH$_3$-C$_6$H$_4$) | NH$_2$ | | |
| 11 | —O—(4-CH$_3$-C$_6$H$_4$) | NHCH$_3$ | crystal | 79~82° C. |

-continued
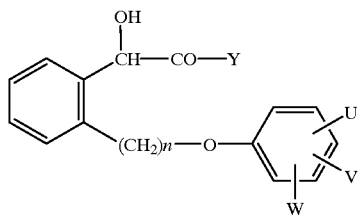
(1-7)
| Comp. No. | —(CH₂)n—O—[ring with U,V,W] | Y | Property | mp or ¹H-NMR(CDCl₃) δ ppm |
|---|---|---|---|---|
| 12 | —O—C₆H₄—CH₃ (para) | NHCH₂OH | | |
| 13 | —O—C₆H₄—CH₃ (para) | N(CH₃)₂ | | |
| 14 | —O—C₆H₄—CH₃ (para) | NHC₂H₅ | | |
| 15 | —O—C₆H₃(CH₃)₂ (3,4-dimethyl) | NHCH₃ | oil | 2.25(6H,s),2.84(3H,d,J=4.9),5.43(1H,s),6.58(1H,brs),6.74(1H, dd, J=7.3, 1.2),6.81(1H, s), 6.83(1H, d, J=7.3),7.11(1H,d,J=7.3), 7.13(1H, dt, J=1.2, 7.3), 7.22(1H, dt, J=1.8, 7.3), 7.54(1H, dd, J=7.3, 1.8). |
| 16 | —O—C₆H₃(CH₃)₂ (3,5-dimethyl) | NHCH₃ | crystal | 119~120° C. |
| 17 | —O—C₆H₂(CH₃)₃ (3,4,5-trimethyl) | NHCH₃ | | |
| 18 | —O—C₆H₄—C₂H₅ (para) | NHCH₃ | | |
| 19 | —O—C₆H₄—CF₃ (meta) | NHCH₃ | | |

-continued
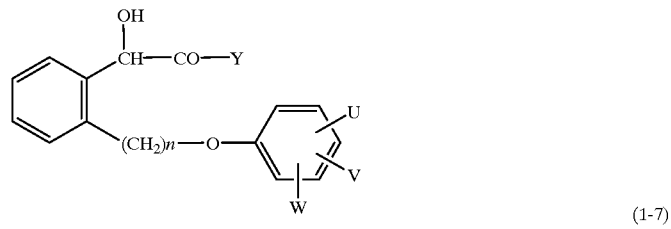
(1-7)
| Comp. No. | W | Y | Property | mp or $^1$H-NMR(CDCl$_3$) δ ppm |
|---|---|---|---|---|
| 20 | 3-Cl-phenoxy | NHCH$_3$ | | |
| 21 | 3-Br-phenoxy | NHCH$_3$ | | |
| 22 | 4-Cl-phenoxy | NH$_2$ | | |
| 23 | 4-Cl-phenoxy | NHCH$_3$ | oil | 2.83(3H, d, J=4.9), 4.20 (1H, brs), 5.36(1H, s), 6.41(1H, brs), 6.84(1H, d, J=6.7), 6.93–6.98(2H, m), 7.16–7.33(4H, m), 7.53(1H, dd, J=7.3, 1.8). |
| 24 | 4-Cl-phenoxy | NHCH$_2$OH | | |
| 25 | 4-Cl-phenoxy | N(CH$_3$)$_2$ | | |
| 26 | 4-Cl-phenoxy | NHC$_2$H$_5$ | | |
| 27 | 4-Br-phenoxy | NHCH$_3$ | | |
| 28 | 4-F-phenoxy | NHCH$_3$ | | |
| 29 | 4-I-phenoxy | NHCH$_3$ | | |

-continued
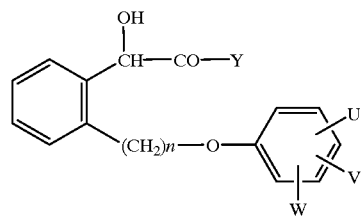
(1-7)
| Comp. No. | —(CH₂)ₙ—O—[ring with U,V,W] | Y | Property | mp or ¹H-NMR(CDCl₃) δ ppm |
|---|---|---|---|---|
| 30 | 3,4-dichlorophenoxy | NHCH₃ | | |
| 31 | 2-chlorophenoxy | NHCH₃ | | |
| 32 | 3-methoxyphenoxy | NHCH₃ | | |
| 33 | 3-propoxyphenoxy | NHCH₃ | | |
| 34 | 4-methoxyphenoxy | NHCH₃ | | |
| 35 | 4-ethoxyphenoxy | NHCH₃ | | |
| 36 | 3,4-dimethoxyphenoxy | NHCH₃ | | |
| 37 | 3-(difluoromethoxy)phenoxy | NHCH₃ | | |
| 38 | 4-(difluoromethoxy)phenoxy | NHCH₃ | | |

-continued
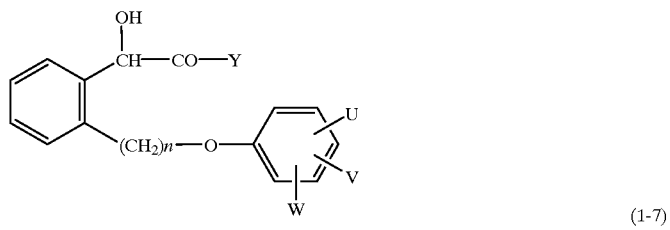
(1-7)
| Comp. No. | —(CH$_2$)$_n$—O—[ring with U,V,W] | Y | Property | mp or $^1$H-NMR(CDCl$_3$) δ ppm |
|---|---|---|---|---|
| 39 | 3-(OCH$_2$CH=CH$_2$)-C$_6$H$_4$-O— | NHCH$_3$ | | |
| 40 | 4-(OCH$_2$CH=CH$_2$)-C$_6$H$_4$-O— | NHCH$_3$ | | |
| 41 | 3-(OCH$_2$C≡CH)-C$_6$H$_4$-O— | NHCH$_3$ | | |
| 42 | 3-(OCH$_2$C≡CCH$_3$)-C$_6$H$_4$-O— | NHCH$_3$ | | |
| 43 | 4-(OCH$_2$C≡CH)-C$_6$H$_4$-O— | NHCH$_3$ | | |
| 44 | 3-(OPh)-C$_6$H$_4$-O— | NHCH$_3$ | | |
| 45 | 4-(OPh)-C$_6$H$_4$-O— | NHCH$_3$ | | |
| 46 | 3-CH$_3$-4-Cl-C$_6$H$_3$-O— | NHCH$_3$ | oil | 2.34(3H, s), 2.83(3H, d, J = 4.9), 4.20(1H, brs), 5.36 (1H, s), 6.41(1H, brs), 6.76–6.90(3H, m), 7.17–7.31 (3H, m), 7.56(1H, dd, J=7.3, 1.8). |

-continued
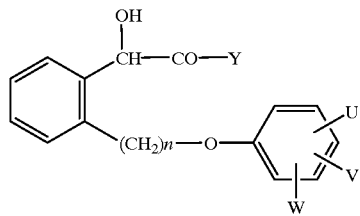
(1-7)
| Comp. No. | —(CH₂)ₙ—O—[ring with U,V,W] | Y | Property | mp or ¹H-NMR(CDCl₃) δ ppm |
|---|---|---|---|---|
| 47 | 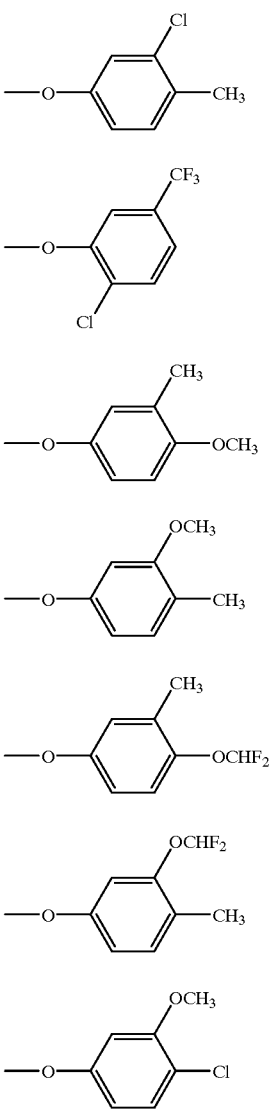 | NHCH₃ | | |
| 48 | 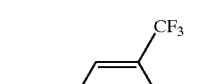 | NHCH₃ | | |
| 49 | 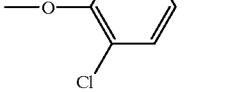 | NHCH₃ | | |
| 50 | 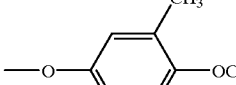 | NHCH₃ | | |
| 51 | 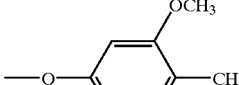 | NHCH₃ | | |
| 52 | 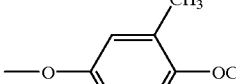 | NHCH₃ | | |
| 53 | 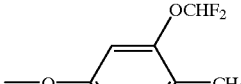 | NHCH₃ | | |
| 54 | 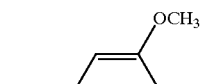 | NHCH₃ | | |

-continued
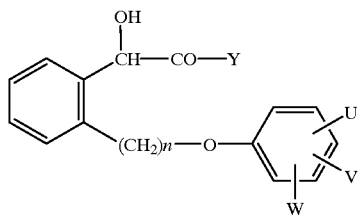
(1-7)
| Comp. No. | —(CH$_2$)$_n$—O—[ring with U,V,W] | Y | Property | mp or $^1$H-NMR(CDCl$_3$) δ ppm |
|---|---|---|---|---|
| 55 | —O—[phenyl with OCHF$_2$, Cl] | NHCH$_3$ | | |
| 56 | —O—[phenyl with Cl, OCHF$_2$] | NHCH$_3$ | | |
| 57 | —O—[phenyl with OCH$_3$, CH$_3$, Cl] | NHCH$_3$ | | |
| 58 | —O—[phenyl with OCH$_2$CH=CH$_2$, CH$_3$] | NHCH$_3$ | | |
| 59 | —O—[phenyl with CH$_3$, OCH$_2$C≡CH] | NHCH$_3$ | | |
| 60 | —O—[phenyl with OCH$_2$CH=CH$_2$, Cl] | NHCH$_3$ | | |
| 61 | —O—[phenyl with OCH$_2$C≡CH] | NHCH$_3$ | | |
| 62 | —CH$_2$O—[phenyl] | NH$_2$ | | |

-continued
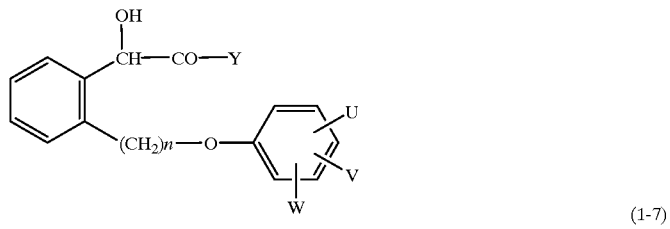
(1-7)
| Comp. No. | —(CH₂)n—O—[ring with U,V,W] | Y | Property | mp or ¹H-NMR(CDCl₃) δ ppm |
|---|---|---|---|---|
| 63 | —CH₂O—C₆H₅ | NHCH₃ | oil | 2.81(3H, d, J=4.9), 5.02(1H, d, J=11.0), 5.26(1H, s), 5.30 (1H, d, J=11.0), 6.73(1H, brs), 6.97(2H, d, J=7.9), 7.05 (1H, t, J=7.3), 7.31–7.50 (6H, m) |
| 64 | —CH₂O—(2-CH₃-C₆H₄) | NHCH₃ | crystal | 104.6~105.7° C. |
| 65 | —CH₂O—(2-CH₃-C₆H₄) | NH₂ | | |
| 66 | —CH₂O—(2-CH₃-C₆H₄) | NHCH₂OH | | |
| 67 | —CH₂O—(2-CH₃-C₆H₄) | N(CH₃)₂ | | |
| 68 | —CH₂O—(2-CH₃-C₆H₄) | NHC₂H₅ | | |
| 69 | —CH₂O—(3-CH₃-C₆H₄) | NHCH₃ | oil | 2.36(3H, s), 2.75(3H, d, J=4.8), 4.55(1H, brs), 4.97 (1H, d, J=11.0), 5.20(1H, s), 5.21(1H, d, J=11.0), 6.73–6.84(4H, m), 7.19(1H, t, J=7.6), 7.28–7.44(4H, m) |
| 70 | —CH₂O—(4-CH₃-C₆H₄) | NHCH₃ | oil | 2.30(3H, s), 2.77(3H, d, J=4.8), 4.55(1H, m), 4.97 (1H, d, J=11.0), 5.23(1H, s), 5.24(1H, d, J=11.0), 6.83(1H, brs), 6.85(2H, d, J=8.8), 7.13(2H, d, J=8.8), 7.29–7.48(4H, m) |

-continued

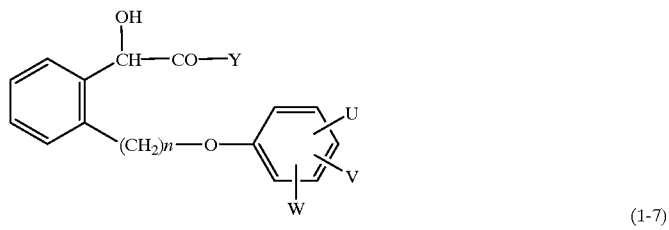

(1-7)

| Comp. No. | ―(CH$_2$)$n$―O― ring with U,V,W | Y | Property | mp or $^1$H-NMR(CDCl$_3$) δ ppm |
|---|---|---|---|---|
| 71 | —CH$_2$O—(3-CF$_3$-phenyl) | NHCH$_3$ | oil | 2.76(3H, d, J=4.8), 4.60(1H, brs), 5.11(1H, d, J=11.0), 5.12(1H, s), 5.16 (1H, d, J=11.0), 6.61(1H, brs), 7.09–7.18(2H, m), 7.27–7.44(6H, m) |
| 72 | —CH$_2$O—(2,3-diCH$_3$-phenyl) | NHCH$_3$ | | |
| 73 | —CH$_2$O—(2,4-diCH$_3$-phenyl) | NHCH$_3$ | | |
| 74 | —CH$_2$O—(2,4-diCH$_3$-phenyl) | NH$_2$ | oil | 2.12(3H,s),2.33(3H,s),4.40 (1H, d, J=4.3), 4.93(1H, d J=11.0), 5.27(1H, d, J=11.0), 5.34(1H, d, J=4.3), 6.06(1H, brs), 6.63(1H, brs),6.75(1H,d, J=7.3), 6.83(1H, s), 7.03(1H, d, J=7.9), 7.29–7.47(4H, m). |
| 75 | —CH$_2$O—(2,4-diCH$_3$-phenyl) | NHCH$_3$ | crystal | 86~87° C. |
| 76 | —CH$_2$O—(2,4-diCH$_3$-phenyl) | NHCH$_2$OH | | |
| 77 | —CH$_2$O—(2,4-diCH$_3$-phenyl) | N(CH$_3$)$_2$ | crystal | 144~145° C. |

-continued
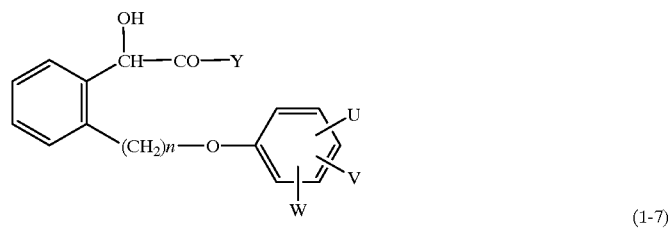
(1-7)
| Comp. No. | —(CH₂)n—O—[ring with U,V,W] | Y | Property | mp or ¹H-NMR(CDCl₃) δ ppm |
|---|---|---|---|---|
| 78 | —CH₂O—(2-CH₃, 5-CH₃ phenyl) | NHC₂H₅ | oil | 0.99(3H, d, J=7.3), 2.17(3H, s), 2.32(3H, s), 3.13–3.27(2H, m), 4.45(1H,d,J=4.3), 4.96 (1H, d, J=11.6), 5.24(1H, d, J=11.6), 5.28(1H, d, J=4.3), 6.62(1H, brs). |
| 79 | —CH₂O—(3,4-diCH₃ phenyl) | NHCH₃ | | |
| 80 | —CH₂O—(3,5-diCH₃ phenyl) | NHCH₃ | | |
| 81 | —CH₂O—(2,3,4-triCH₃ phenyl) | NHCH₃ | | |
| 82 | —CH₂O—(2,4,5-triCH₃ phenyl) | NHCH₃ | | |
| 83 | —CH₂O—(3,4,5-triCH₃ phenyl) | NHCH₃ | | |
| 84 | —CH₂O—(2-Cl phenyl) | NH₂ | | |

-continued
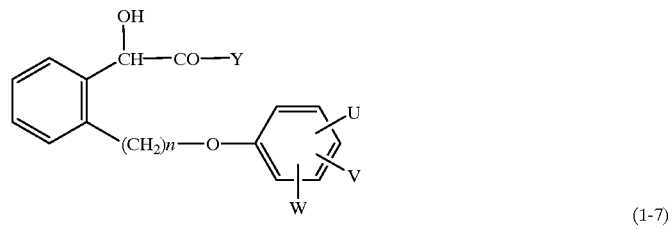
(1-7)
| Comp. No. | —(CH₂)n—O—[ring with U,V,W] | Y | Property | mp or ¹H-NMR(CDCl₃) δ ppm |
|---|---|---|---|---|
| 85 | —CH₂O—(2-Cl-C₆H₄) | NHCH₃ | oil | 2.80(3H, d, J=4.9), 4.99(1H, d, J=10.4), 5.28(1H, s), 5.42(1H, d, J=10.4), 6.62 (1H, brs), 7.00(1H, t, J=7.3), 7.16(1H, d, J=7.9), 7.28–7.50(6H, m) |
| 86 | —CH₂O—(2-Cl-C₆H₄) | NHCH₂OH | | |
| 87 | —CH₂O—(2-Cl-C₆H₄) | N(CH₃)₂ | | |
| 88 | —CH₂O—(2-Cl-C₆H₄) | NHC₂H₅ | | |
| 89 | —CH₂O—(3-Cl-C₆H₄) | NHCH₃ | | |
| 90 | —CH₂O—(4-Cl-C₆H₄) | NH₂ | | |
| 91 | —CH₂O—(4-Cl-C₆H₄) | NHCH₃ | crystal | 68~70° C. |
| 92 | —CH₂O—(4-Cl-C₆H₄) | NHCH₂OH | | |
| 93 | —CH₂O—(4-Cl-C₆H₄) | N(CH₃)₂ | | |

-continued
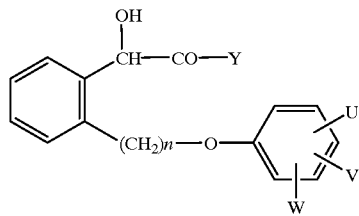
(1-7)
| Comp. No. | —(CH₂)n—O—[ring with U,V,W] | Y | Property | mp or ¹H-NMR(CDCl₃) δ ppm |
|---|---|---|---|---|
| 94 | —CH₂O—C₆H₄—Cl (4-Cl) | NHC₂H₅ | | |
| 95 | —CH₂O—C₆H₄—Br (2-Br) | NHCH₃ | | |
| 96 | —CH₂O—C₆H₄—Br (4-Br) | NHCH₃ | | |
| 97 | —CH₂O—C₆H₄—F (4-F) | NHCH₃ | | |
| 98 | —CH₂O—C₆H₄—I (4-I) | NHCH₃ | | |
| 99 | —CH₂O—C₆H₃—(2,4-Cl₂) | NHCH₃ | oil | 2.80(3H, d, J=4.9), 5.00(1H, d, J=11.0), 5.26(1H, s), 5.38(1H, d, J=11.0), 6.50(1H, brs), 7.07(1H, d, J=8.5), 7.25–7.29(1H, m), 7.31–7.50 (5H, m) |
| 100 | —CH₂O—C₆H₃—(3,4-Cl₂) | NHCH₃ | | |
| 101 | —CH₂O—C₆H₃—(2,5-Cl₂) | NHCH₃ | | |
| 102 | —CH₂O—C₆H₄—OCH₃ (2-OCH₃) | NHCH₃ | | |

-continued (1-7)

| Comp. No. | —(CH₂)n—O—[ring with U,V,W] | Y | Property | mp or ¹H-NMR(CDCl₃) δ ppm |
|---|---|---|---|---|
| 103 | —CH₂O—(3-OCH₃-C₆H₄) | NHCH₃ | | |
| 104 | —CH₂O—(4-OCH₃-C₆H₄) | NHCH₃ | oil | 2.76(3H, d, J=4.8), 3.76(3H, s), 4.50(1H, brs), 4.95(1H, d, J=11.0), 5.19(1H, d, J=11.0) 5.24(1H, s), 6.83–6.88(5H, m), 7.30–7.43(4H, m) |
| 105 | —CH₂O—(3-OC₂H₅-C₆H₄) | NHCH₃ | | |
| 106 | —CH₂O—(3-OCH₂CH=CH₂-C₆H₄) | NHCH₃ | | |
| 107 | —CH₂O—(4-OCH₂C≡CH-C₆H₄) | NHCH₃ | | |
| 108 | —CH₂O—(2-OCHF₂-C₆H₄) | NHCH₃ | | |
| 109 | —CH₂O—(4-OCHF₂-C₆H₄) | NHCH₃ | | |
| 110 | —CH₂O—(3-OC₆H₅-C₆H₄) | NHCH₃ | | |

-continued

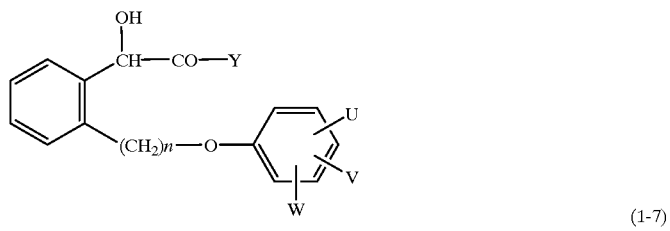

(1-7)

| Comp. No. | —(CH$_2$)$n$—O—[ring with U,V,W] | Y | Property | mp or $^1$H-NMR(CDCl$_3$) δ ppm |
|---|---|---|---|---|
| 111 | —CH$_2$O—[phenyl with OCH$_3$, OCH$_3$] | NHCH$_3$ | | |
| 112 | —CH$_2$O—[phenyl with CH$_3$, Cl] | NH$_2$ | crystal | 151~152° C. |
| 113 | —CH$_2$O—[phenyl with CH$_3$, Cl] | NHCH$_3$ | crystal | 142~143° C. |
| 114 | —CH$_2$O—[phenyl with CH$_3$, Cl] | NHCH$_2$OH | | |
| 115 | —CH$_2$O—[phenyl with CH$_3$, Cl] | N(CH$_3$)$_2$ | crystal | 125~127° C. |
| 116 | —CH$_2$O—[phenyl with CH$_3$, Cl] | NHC$_2$H$_5$ | oil | 0.99–1.17(3H in total), 2.19(3H, s), 3.15–3.31(2H in total), 4.48(1H, br), 5.02(1H, d, J = 11.8), 5.18 (1H, d, J=11.6), 5.21(1H, s), 6.61(1H, brs), 6.83(1H, d, J = 8.5), 7.08(1H, d, J = 8.5), 7.12(1H, s), 7.31–7.43(4H, m). |
| 117 | —CH$_2$O—[phenyl with CH$_3$, Br] | NHCH$_3$ | | |
| 118 | —CH$_2$O—[phenyl with CH$_3$, CH$_3$] | NHCH$_3$ | | |

-continued
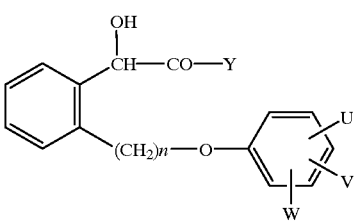
(1-7)
| Comp. No. | 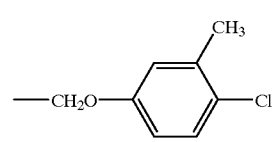 | Y | Property | mp or $^1$H-NMR(CDCl$_3$) δ ppm |
|---|---|---|---|---|
| 119 | 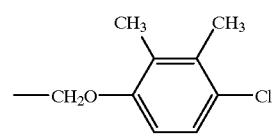 | NHCH$_3$ | | |
| 120 | 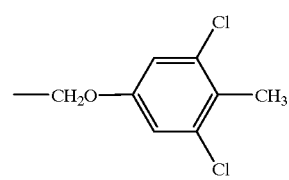 | NHCH$_3$ | | |
| 121 | 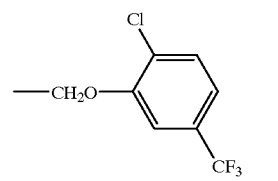 | NHCH$_3$ | | |
| 122 | 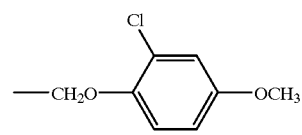 | NHCH$_3$ | | |
| 123 | 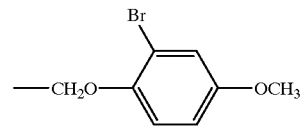 | NHCH$_3$ | | |
| 124 | 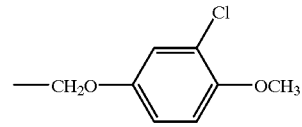 | NHCH$_3$ | | |
| 125 | | NHCH$_3$ | | |

-continued
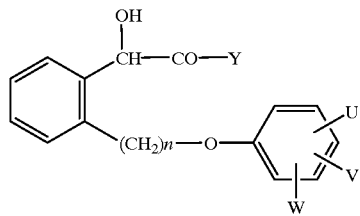
(1-7)
| Comp. No. | —(CH₂)ₙ—O—[ring with U,V,W] | Y | Property | mp or ¹H-NMR(CDCl₃) δ ppm |
|---|---|---|---|---|
| 126 | —CH₂O—C₆H₃(OCH₃)(Cl) (2-OCH₃, 1-Cl on phenyl) | NHCH₃ | | |
| 127 | —CH₂O—C₆H₂(Cl)(OCH₃)(Cl) | NHCH₃ | | |
| 128 | —CH₂O—C₆H₃(Cl)(OCHF₂) | NHCH₃ | | |
| 129 | —CH₂O—C₆H₃(Cl)(OCHF₂) | NHCH₃ | | |
| 130 | —CH₂O—C₆H₃(CH₃)(OCH₃) | NHCH₃ | | |
| 131 | —CH₂O—C₆H₃(OCH₃)(CH₃) | NHCH₃ | | |
| 132 | —CH₂O—C₆H₃(CH₃)(OCHF₂) | NHCH₃ | | |
| 133 | —CH₂O—C₆H₃(CH₃)(OCHF₂) | NHCH₃ | | |

-continued

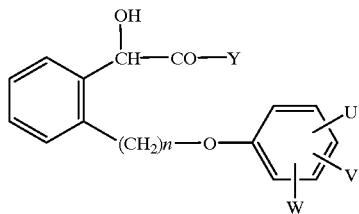

(1-7)

| Comp. No. | —(CH₂)n—O—[ring with U,V,W] | Y | Property mp or ¹H-NMR(CDCl₃) δ ppm |
|---|---|---|---|
| 134 | —O—[phenyl with 2-CH₃, 3-CH₃] | NH$_2$ | |
| 135 | —O—[phenyl with 2-CH₃, 3-CH₃] | NHCH$_2$OH | |
| 136 | —O—[phenyl with 2-CH₃, 5-CH₃] | NH$_2$ | |
| 137 | —O—[phenyl with 2-CH₃, 5-CH₃] | NHCH$_2$OH | |

Example 4

Synthesis of methyl 2-[2-(2,5-dimethylphenoxymethyl)phenyl]-2-methoxyacetate (Compound No. 139)

60% oily sodium hydride (0.13 g, 3.3 mmol) was added to a solution of methyl 2-[2-(2,5-dimethylphenoxymethyl)-phenyl]-2-hydroxyacetate (0.72 g, 2.4 mmol) and methyl iodide (0.68 g, 4.8 mmol) in N,N-dimethylformamide (6 ml) at 0° C. with stirring. After 30 minutes, ice and water were added in this order, and the mixture was extracted with ethyl acetate, washed successively with water and saturated brine, and dried over anhydrous sodium sulfate. The solvent was evaporated, and the residue was purified by column chromatography on silica gel (n-hexane/ethyl acetate=9/1) to give the desired compound methyl 2-[2-(2,5-dimethylphenoxymethyl)phenyl]-2-hydroxyacetate (0.69 g, 92%) as an oil.

NMR (δ ppm, TMS/CDCl₃): 2.21(3H,s), 2.33(3H,s), 3.40(3H,s), 3.70(3H,s), 5.10(1H,d,J=12.2), 5.14(1H,s), 5.28 (1H, d,J=12.2), 6.71(1H,d,J=7.3), 6.76(1H,s), 7.04(1H,d,J=7.3), 7.33–7.40(2H,m), 7.50–7.56(2H,m).

Example 5

Synthesis of 2-[2-(2,5-dimethylphenoxymethyl) phenyl]-2-methoxy-N-methylacetamide (Compound No. 140)

A solution of methyl 2-[2-(2,5-dimethylphenoxymethyl) phenyl)-2-methoxyacetate (0.44 g, 1.40 mmol) in methanol (5 ml) was stirred at room temperature. 40% methylamine/methanol solution (0.33 g, 4.2 mmol) was added thereto. After 22 hours, the mixture was concentrated under reduced pressure, and the residue was purified by column chromatography on silica gel (n-hexane/ethyl acetate=2/1) to give the desired compound 2-[2-(2,5-dimethylphenoxymethyl) phenyl]-2-methoxy-N-methylacetamide (0.36 g, 82%) as white crystals.

mp. 86–88° C.

NMR (δ ppm, TMS/CDCl₃): 2.19(3H,s), 2.32(3H,s), 2.83 (3H,d,J=4.9), 3.36(3H,s), 5.04(1H,s), 5.07(1H,d,J=11.6), 5.47 (1H,d,J=1.6), 6.70(1H,d,J=7.3), 6.79(1H,brs), 6.79(1H, s), 7.03(1H,d,J=7.9), 7.33–7.43(3H,m), 7.49–7.54(1H,m).

Example 6

Synthesis of 2-[2-(2,5-dimethylphenoxymethyl) phenyl]-2-methoxy-N-methylthioacetamide (Compound No. 170)

A solution of 2-[2-(2,5-dimethylphenoxymethyl)phenyl]-2-methoxy-N-methylacetamide (0.12 g, 0.38 mmol) and Lawesson's reagent (0.14 g, 0.35 mmol) in toluene (5 ml) was heated with stirring at 80° C. for 2 hours. The mixture was cooled to room temperature, and purified by column chromatography on silica gel (n-hexane/ethyl acetate=4/1) to give the desired compound 2-[2-( 2,5-dimethylphenoxymethyl)-phenyl]-2-methoxy-N-methylthioacetamide (0.13 g, 100%) as an oil.

NMR ($\delta$ ppm TMS/CDCl$_3$): 2.20(3H,s), 2.32(3H,s), 3.23 (3H,d,J=4.8), 3.35(3H,s), 5.12(1H,d,J=11.6), 5.40(1H,s), 5.58 (1H,d,J=11.6), 6.70(1H,d,J=7.3), 6.81(1H,s), 7.03(1H, d,J=7.3), 7.28–7.38(3H,m), 7.48–7.52(1H,m), 8.78(1H,brs).

Example 7

Synthesis of 2-acetoxy-2-[2-(2,5-dimethylphenoxymethyl)phenyl]-2-N-methylacetamide (Compound No. 144)

A solution of 2-[2-(2,5-dimethylphenoxymethyl)phenyl]-2-hydroxy-N-methylacetamide (0.57 g, 1.9 mmol) and acetic anhydride (0.43 g, 4.2 mmol) in pyridine (3 ml) was stirred at room temperature for 8 hours, and then concentrated under reduced pressure. The residue was purified by column chromatography on silica gel (n-hexane/ethyl acetate=1/1) to give the desired compound 2-acetoxy-2-[2-(2,5-dimethylphenoxymethyl)phenyl]-N-methylacetamide (0.53 g, 82%) as colorless crystals.

mp.: 114–115° C.

NMR ($\delta$ ppm TMS/CDCl$_3$): 2.18(3H,s), 2.19(3H,s), 2.34 (3H,s), 2.76(3H,d,J=4.9), 5.02(1H,d,J=11.6), 5.45 (1H,d,J=11.6), 6.19(1H,brs), 6.35(1H,s), 6.75(1H,d,J=7.3), 6.85(1H, s), 7.05(1H,d,J=7.3), 7.36–7.58(4H,m).

Example 8

Synthesis of methyl 2-chloro-2-[2-(2,5-dimethylphenoxymethyl)phenyl]acetate (Compound No. 149)

A solution of methyl 2-[2-(2,5-dimethylphenoxymethyl) phenyl]-2-hydroxyacetate (0.50 g, 1.6 mmol) in 1,2-dichloroethane (20 ml) was stirred at room temperature. Thionyl chloride (0.61 g, 5.1 mmol) was added thereto, and the mixture was heated under reflux overnight and concentrated under reduced pressure. The residue was purified by column chromatography on silica gel (n-hexane/ethyl acetate=97/3) to give the desired compound methyl 2-chloro-2-[2-(2,5-dimethylphenoxymethyl)phenyl]acetate (0.35 g, 66%) as an oil.

NMR ($\delta$ ppm TMS/CDCl$_3$): 2.20(3H,s), 2.35(3H,s), 3.76 (3H,s), 5.14(2H,s), 5.84(1H,s), 6.73(1H,d,J=7.3), 6.77(1H, s), 7.05(1H,d,J=7.3), 7.38–7.48(3H,m), 7.66(1H,d,J=7.3).

Example 9

Synthesis of methyl 2-[2-(2,5-dimethylphenoxymethyl)phenyl]-2-nitroacetate (Compound No. 439)

A solution of methyl 2-chloro-2-[2-(2,5-dimethylphenoxymethyl)phenyl]acetate (0.35 g, 1.1 mmol), sodium nitrite (0.13 g, 1.9 mmol) and phloroglucinol (0.145 g, 1.1 mol) in N,N-dimethylformamide (10 ml) was stirred at room temperature for 6 hours. Water was added to the mixture. The resulting mixture was extracted with ether, washed successively with water and saturated brine, and dried over anhydrous sodium sulfate. The solvent was evaporated, and the residue was purified by column chromatography on silica gel (n-hexane/methylene chloride=1/1) to give the desired compound methyl 2-[2-(2,5-dimethylphenoxymethyl)phenyl]-2-nitroacetate (0.08 g, 22%) as an oil.

NMR ($\delta$ ppm, TMS/CDCl$_3$): 2.09(3H,s), 2.34(3H,s), 3.85 (3H,s), 5.05(1H,d,J=11.0), 5.10(1H,d,J=11.0), 6.68(1H,s), 6.74 (1H,d,J=7.3), 6.75(1H,s), 7.03(1H,d,J=7.3), 7.48–7.53 (2H,m), 7.61–7.66(1H,m).

Example 10

Synthesis of methyl 2-[2-(2,5-dimethylphenoxymethyl)phenyl]-2-methylthioacetate (Compound No. 162)

A solution of methyl 2-chloro-2-[2-(2,5-dimethylphenoxymethyl)phenyl]acetate (0.21 g, 0.66 mmol) and sodium thiomethoxide (0.06 g, 0.86 mmol) in N,N-dimethylformamide (3 ml) was stirred at room temperature for 24 hours. Water was added, and the mixture was extracted with ether, washed successively with water and saturated brine and dried over anhydrous sodium sulfate. The solvent was evaporated, and the residue was purified by column chromatography on silica gel (n-hexane/ethyl acetate=9/1) to give the desired compound methyl 2-[2-(2, 5-dimethylphenoxymethyl)phenyl]-2-thiomethyl-acetate (0.13 g, 60%) as an oil.

NMR ($\delta$ ppm, TMS /CDCl$_3$): 2.10 (3H, s), 2.20(3H,s), 2.34 (3H,s), 3.71(3H,s), 4.95(1H,s), 5.13(2H,s), 6.72(1H,d, J=7.3), 6.77(1H,S), 7.04(1H,d,J=7.3), 7.30–7.40 (2H,m), 7.46 (1H,dd,J=7.3,1.8), 7.68(1H,dd,J=7.3,1.8).

Example 11

Synthesis of methyl 2-[2-(2,5-dimethylphenoxymethyl)phenyl]-2-methylsulfinylacetate (Compound No. 358) and methyl 2-[2-(2,5-dimethylphenoxymnethyl)phenyl]-2-methylsulfonylacetate (Compound No. 359)

A solution of methyl 2-[2-(2,5-dimnethyiphenoxymethyl) phenyl]-2-methylthioacetate (0.13 g, 0.39 mmol) in methylene chloride (5 ml) was stirred at 0° C. 80% m-chloroperbenzoic acid (0.12 g, 0.56 mmol) was added thereto. The mixture was stirred at 0° C. for 2 hours, washed with aqueous sodium thiosulfate solution, 1N sodium hydroxide solution and dried over anhydrous sodium sulfate. The solvent was evaporated, and the residue was purified by column chromatography on silica gel (n-hexane/ethyl acetate=3/1 followed by 1/1) to give the desired compound methyl 2-[2-(2,5-dimethylphenoxyinethyl)phenyl]-2-methylsulfonylacetate (0.08 g, 56%) as crystals and methyl 2-[2-(2,5-dimethylphenoxymethyl)phenyl]-2-methylsulfinylacetate (0.03 g, 22%) as an oil.

Compound No. 359; mp. 122–124° C.

NMR ($\delta$ ppm TMS/CDCl$_3$): 2.17(3H,s), 2.34(3H,s), 3.03 (3H,s), 3.81(3H,s), 5.02(1H,d,J=11.6), 5.39(1H,d,J=11.6), 5.67 (1H,s), 6.72(1H,d,J=7.3), 6.79(1H,s), 7.03(1H,d,J= 7.3), 7.40–7.55(3H,m), 7.81–7.85(1H,m).

Compound No. 358; NMR ($\delta$ ppm, TMS/CDCl$_3$): 2.17 (3H,s), 2.34 and 2.36 (3H in total), 2.44 and 2.63 (3H in total), 3.78 and 3.81 (3H in total), 4.98–5.22 (3H in total), 6.71–7.81(7H in total).

Example 12

Synthesis of 2-[2-(2,5-dimethylphenoxymethyl) phenyl]butyronitrile

A solution of 2-[2-(2,5-dimethylphenoxymethyl)phenyl] acetonitrile (2.00 g, 8.0 mmol) in N,N-dimethylformamide (20 ml) was stirred at 0° C. 60% oily sodium hydride (0.38 g, 9.5 mmol) was added thereto, and then ethyl iodide (1.37 g, 8.8 mmol) was added dropwise over 5 minutes. After 1 hour, water was added, and the mixture was extracted with ethyl acetate, washed successively with water and saturated brine and dried over anhydrous sodium sulfate. The solvent was evaporated, and the residue was purified by column chromatography on silica gel (n-hexane/ethyl acetate=19/1) to give the desired compound 2-[2-(2,5-dimethylphenoxymethyl)phenyl]butyronitrile (1.91 g, 86%) as an oil.

NMR (δ ppm TMS/CDCl$_3$): 1.10(3H,t,J=7.3), 1.97 (2H, quintet,J=7.3), 2.16(3H,s), 2.34(3H,s), 4.05(1H,t,J=7.3), 4.96(1H,d,J=11.0), 5.05(1H,d,J=11.0), 6.73(1H,d,J=7.3), 6.76 (1H,s), 7.04(1H,d,J=7.3), 7.31–7.44(3H,m), 7.55(1H, d,J=7.9).

Example 13

Synthesis of 2-[2-(2,5-dimethylphenoxymethyl) phenyl]butylamide (Compound No. 159)

A solution of 2-[2-(2,5-dimethylphenoxymethyl)phenyl] butyronitrile (1.00 g, 3.6 mmol) and 96% sodium hydroxide (0.44 g, 10.6 mmol) in methanol (10 ml) was heated under reflux for 44 hours. The solvent was evaporated, and then water was added. The mixture was extracted with ethyl acetate, washed with saturated brine and dried over anhydrous sodium sulfate. The solvent was evaporated, and the residue was purified by column chromatography on silica gel (n-hexane/ethyl acetate=3/1) to give the desired compound 2-[2-(2,5-dimethylphenoxymethyl)phenyl] butylamide (0.28 g, 26%) as white crystals.

mp.: 100–101° C.

NMR (δ ppm TMS/CDCl$_3$): 0.89(3H,t,J=7.3), 1.78–1.89 (1H,m), 2.15(3H,s), 2.15–2.28(1H,m), 2.36(3H,s), 3.73 (1H, t,J=7.3), 4.84(1H,d,J=11.0), 5.20(1H,brs), 5.26 (1H,d,J=11.0), 5.86(1H,brs), 6.77(1H,d,J=7.3), 7.30 (1H,d,J=7.3), 7.38–7.43(2H,m), 7.49(1H,d,J=7.3).

Example 14

Synthesis of 2-[2-(2,5-dimethylphenoxymethyl) phenyl]-N-methylbutylamide (Compound No. 146) and N,N-dimethyl-2-[2-(2,5-dimethylphenoxymethyl)phenyl]butylamide (Compound No. 163)

2-[2-(2,5-Dimethylphenoxymethyl)phenyl]butylamide (0.19 g, 0.6 mmol) was dissolved in N,N-dimethylformamide (5 ml), and the solution was stirred at 0° C. 60% oily sodium hydride (0.05 g, 1.3 mmol) was added thereto. After 5 minutes, methyl iodide (0.18 g, 1.3 mmol) was added, and then the mixture was stirred at room temperature for 2 hours. Ice and water were added in this order at 0° C., and the mixture was extracted with ethyl acetate. The extract was washed successively with water and saturated brine and dried over anhydrous sodium sulfate. The solvent was evaporated, and the residue was purified by column chromatography on silica gel (n-hexane/ethyl acetate=4/1 followed by 3/1) to give the desired compound N,N-dimethyl-2-[2-(2,5-dimethylphenoxymethyl)phenyl] butylamide (0.06 g, 29%) as white crystals and 2-[2-(2,5-dimethylphenoxymethyl)phenyl]-N-methylbutylamide (0.11 g, 55%) as white crystals.

Compound No. 163; mp.: 62–62.5° C.

NMR (δ ppm, TMS/CDCl$_3$): 0.94(3H,t,J=7.3), 1.62–1.77 (1H,m), 2.09–2.26(1H,m), 2.14(3H,s), 2.36(3H,s), 2.85 (3H, s), 2.95(3H,s), 3.93(1H,dd,J=9.1,4.9), 4.96(1H,d,J=11.0), 5.15(1H,d,J=11.0), 6.73(1H,d,J=7.3), 6.80(1H,s), 7.05 (1H, d,J=7.9), 7.23–7.46(4H,m).

Compound No. 146; mp.: 108–110° C.

NMR (δ ppm TMS/CDCl$_3$): 0.86(3H,t,J=7.3), 1.77–1.88 (1H,m), 2.16(3H,s), 2.16–2.29(1H,m), 2.35(3H,s), 2.67 (3H, d,J=4.9), 3.63(1H,t,J=7.3), 4.84(1H,d,J=11.0), 5.24 (1H,d, J=11.0), 5.80(1H,brs), 6.76(1H,d,J=7.3), 6.84(1H,s), 7.06 (1H,d,J=7.3), 7.27(1H,t,J=7.3), 7.38(2H;t,J=7.3), 7.49 (1H, d,J=7.3).

Example 15

Synthesis of methyl 2-[2-(2,5-dimethylphenoxymethyl)phenyl]butyrate (Compound No. 145)

A solution of 2-[2-(2,5-dimethylphenoxymethyl)phenyl] butyronitrile (0.67 g, 2.4 mmol) and 96% sodium hydroxide (0.73 g, 17.5 mmol) in ethanol (8 ml) was heated under reflux for 43 hours. The solvent was evaporated, and then water was added. The mixture was adjusted to pH 3 with 1N hydrochloric acid and extracted with ethyl acetate. The extract was dried over anhydrous sodium sulfate, and then the solvent was evaporated. The crude product was dissolved in N,N-dimethylformamide (5 ml) and stirred at room temperature. Methyl iodide (0.50 g, 3.5 mmol) and potassium carbonate (0.50 g, 3.6 mmol) were added thereto in this order. After 1 hour, water was added, and the mixture was extracted with ethyl acetate. The extract was washed successively with water and saturated brine and dried over anhydrous sodium sulfate. The solvent was evaporated, and the residue was purified by column chromatography on silica gel (n-hexane/ethyl acetate=9/1) to give the desired compound methyl 2-[2-(2,5-dimethylphenoxymethyl) phenyl]butyrate (0.62 g, 83%) as white crystals.

mp.: 62–65° C.

NMR (δ ppm, TMS/CDCl$_3$): 0.91(3H,t,J=7.3), 1.78–1.89 (1H,m), 2.07–2.21(1H,m), 2.18(3H,s), 2.34(3H,s), 3.64(3H, s), 3.84(1H,t,J=7.3), 5.02(1H,d,J=11.0), 5.19 (1H,d,J=11.0), 6.71 (1H,d,J=7.3), 6.78(1H,s), 7.04(1H,d,J=7.3), 7.27–7.44 (2H,m), 7.44–7.47(2H,m).

Example 16

Synthesis of α-methoxy-N-methyl-(2,3,5-trimethylphenoxymethyl)phenylacetamide (Compound No. 465)

A solution of 2-chloromethyl-α-methoxy-N-methyl-phenylacetamide (0.25 g, 1.1 mmol) and 2,3,5-trimethylphenol (0.18 g, 1.3 mmol) in N,N-dimethylformamide (3 ml) was stirred at 0° C., and 60% oily sodium hydride (0.08 g, 2.0 mmol) was added thereto. The mixture was stirred at 0° C. for 70 minutes and then at room temperature for 1 hour, and ice and water were added in this order. The mixture was extracted with ethyl acetate, washed with saturated brine and dried over anhydrous sodium sulfate. The solvent was evaporated, and the residue was purified by column chromatography on silica gel (n-hexane/ethyl acetate=7/3) to give the desired compound α-methoxy-N-methyl-(2,3,5-trimethylphenoxymethyl)phenylacetamide (0.17 g, 50%) as an oil.

NMR (δ ppm, TMS/CDCl$_3$): 2.11(3H,s), 2.23(3H,s), 2.29 (3H,s), 2.81(3H,d,J=4.9), 3.35(3H,s), 5.03(1H,s), 5.03(1H, d,J=11.6), 5.44(1H,d,J=11.6), 6.64(1H,s), 6.68(1H,s), 6.80 (1H,brs), 7.32–7.43(3H,m), 7.50–7.53(1H,m).

Example 17

Synthesis of (3-chloro-5-trifluoromethyl-2-pyridyloxymethyl)-α-methoxy-N-methyl-phenylacetamide (Compound No. 427)

A solution of 2-hydroxymethyl-α-methoxy-N-methyl-phenylacetamide (1.00 g, 4.8 mmol) in N,N-dimethylformamide (5 ml) was stirred at 0° C., and 60% oily sodium hydride (0.19 g, 4.8 mmol) was added thereto. The mixture was stirred at 0° C. for 30 minutes, and then 2,3-dichloro-5-trifluoromethylpyridine (1.24 g, 5.7 mmol) was added. The mixture was stirred at 0° C. for 2 hours, and then ice and water were added in this order. The mixture was extracted with ether, washed with saturated brine and dried over anhydrous sodium sulfate. The solvent was evaporated, and the residue was purified by column chromatography on silica gel (n-hexane/ethyl acetate=1/1) to give the desired compound (3-chloro-5-trifluoromethyl-2-pyridyloxymethyl)-α-methoxy-N-methyl-phenylacetamide (1.40 g, 75%) as mp.: 133–135° C.

NMR (δ ppm, TMS/CDCl$_3$): 2.83(3H,d,J=4.9), 3.38 (3H, s), 5.19(1H,s), 5.60(1H,d,J=12.2), 5.92(1H,d,J=12.2), 6.80 (1H,brs), 7.28–7.40(3H,m), 7.55–7.58(1H,m), 7.84(1H,s), 8.32 (1H,s).

Example 18

According to the same manner as that described in Examples 4 to 17, various compounds of the formula (I) were synthesized. The compounds thus obtained and the physical data of their representative compounds are shown below. In the tables, U, V and W mean the substituents in the group of the formula (XX) represented by Q. In the tables, the compounds obtained in Examples 4 to 17 and their physical data are also listed.

| Comp. No. | X | R$^1$ | Z | Y | M | n | U | V | W |
|---|---|---|---|---|---|---|---|---|---|
| 139 | H | OCH$_3$ | O | OCH$_3$ | O | 1 | 2-CH$_3$ | 5-CH$_3$ | H |
| 140 | H | OCH$_3$ | O | NHCH$_3$ | O | 1 | 2-CH$_3$ | 5-CH$_3$ | H |
| 141 | H | OCH$_2$OCH$_3$ | O | OCH$_3$ | O | 1 | 2-CH$_3$ | 5-CH$_3$ | H |
| 142 | H | OCH$_2$OCH$_3$ | O | NHCH$_3$ | O | 1 | 2-CH$_3$ | 5-CH$_3$ | H |
| 143 | H | OCOCH$_3$ | O | OCH$_3$ | O | 1 | 2-CH$_3$ | 5-CH$_3$ | H |
| 144 | H | OCOCH$_3$ | O | NHCH$_3$ | O | 1 | 2-CH$_3$ | 5-CH$_3$ | H |
| 145 | H | C$_2$H$_5$ | O | OCH$_3$ | O | 1 | 2-CH$_3$ | 5-CH$_3$ | H |
| 146 | H | C$_2$H$_5$ | O | NHCH$_3$ | O | 1 | 2-CH$_3$ | 5-CH$_3$ | H |
| 147 | H | NH$_2$ | O | OCH$_3$ | O | 1 | 2-CH$_3$ | 5-CH$_3$ | H |
| 148 | H | NH$_2$ | O | NHCH$_3$ | O | 1 | 2-CH$_3$ | 5-CH$_3$ | H |
| 149 | H | Cl | O | OCH$_3$ | O | 1 | 2-CH$_3$ | 5-CH$_3$ | H |
| 150 | H | Cl | O | NHCH$_3$ | O | 1 | 2-CH$_3$ | 5-CH$_3$ | H |
| 151 | H | OC$_2$H$_5$ | O | OCH$_3$ | O | 1 | 2-CH$_3$ | 5-CH$_3$ | H |
| 152 | H | OC$_4$H$_9$ | O | OCH$_3$ | O | 1 | 2-CH$_3$ | 5-CH$_3$ | H |
| 153 | H | OCH$_2$CH=CH$_2$ | O | OCH$_3$ | O | 1 | 2-CH$_3$ | 5-CH$_3$ | H |
| 154 | H | CF$_3$ | O | OCH$_3$ | O | 1 | 2-CH$_3$ | 5-CH$_3$ | H |
| 155 | H | OC$_2$H$_5$ | O | NHCH$_3$ | O | 1 | 2-CH$_3$ | 5-CH$_3$ | H |
| 156 | H | OC$_4$H$_9$ | O | NHCH$_3$ | O | 1 | 2-CH$_3$ | 5-CH$_3$ | H |
| 159 | H | C$_2$H$_5$ | O | NH$_2$ | O | 1 | 2-CH$_3$ | 5-CH$_3$ | H |
| 160 | H | SCH$_3$ | O | NHCH$_3$ | O | 1 | 2-CH$_3$ | 5-CH$_3$ | H |
| 161 | H | OCH$_3$ | O | NH$_2$ | O | 1 | 2-CH$_3$ | 5-CH$_3$ | H |
| 162 | H | SCH$_3$ | O | OCH$_3$ | O | 1 | 2-CH$_3$ | 5-CH$_3$ | H |
| 163 | H | C$_2$H$_5$ | O | N(CH$_3$)$_2$ | O | 1 | 2-CH$_3$ | 5-CH$_3$ | H |
| 165 | H | 9CH$_3$ | O | N(CH$_3$)$_2$ | O | 1 | 2-CH$_3$ | 5-CH$_3$ | H |
| 166 | H | OC$_2$H$_5$ | | N(CH$_3$)$_2$ | O | 1 | 2-CH$_3$ | 5-CH$_3$ | H |
| 167 | H | C$_2$H$_5$ | O | OH | O | 1 | 2-CH$_3$ | 5-CH$_3$ | H |
| 169 | H | OCH$_3$ | S | OCH$_3$ | O | 1 | 2-CH$_3$ | 5-CH$_3$ | H |
| 170 | H | OCH$_3$ | S | NHCH$_3$ | O | 1 | 2-CH$_3$ | 5-CH$_3$ | H |
| 171 | H | OCOCH$_3$ | O | NHCH$_3$ | O | 0 | H | H | H |
| 173 | H | OCOCH$_3$ | O | NHCH$_3$ | O | 0 | 2-CH$_3$ | H | H |
| 174 | H | OCH$_3$ | O | OCH$_3$ | O | 1 | 4-Cl | H | H |
| 175 | H | C$_2$H$_5$ | O | OH | O | 0 | 4-OCH$_3$ | H | H |
| 176 | H | OCH$_3$ | O | SCH$_3$ | O | 1 | 2-CH$_3$ | 5-CH$_3$ | H |
| 177 | H | C$_2$H$_5$ | O | NH$_2$ | O | 0 | 4-OCH$_3$ | H | H |
| 178 | H | OCOCH$_3$ | O | NHCH$_3$ | O | 0 | 3-CH$_3$ | 4-CH$_3$ | H |
| 179 | H | OCH$_3$ | O | N(CH$_3$)$_2$ | O | 1 | 2-CH$_3$ | H | H |
| 180 | H | C$_2$H$_5$ | O | OCH$_3$ | O | 0 | 4-OCH$_3$ | H | |
| 181 | H | OCOCH$_3$ | O | OCH$_3$ | O | 0 | H | H | H |
| 182 | H | OCH$_3$ | O | OCH$_3$ | O | 0 | H | H | H |
| 183 | H | OC$_2$H$_5$ | O | OCH$_3$ | O | 0 | H | H | H |
| 184 | H | OCH$_3$ | O | NHCH$_3$ | O | 0 | H | H | H |
| 185 | H | OCH$_3$ | O | OC$_2$H$_5$ | O | 1 | 2-CH$_3$ | 4-Cl | H |
| 186 | H | OCH$_3$ | O | NHCH$_3$ | O | 1 | 2-CH$_3$ | 4-Cl | H |
| 188 | H | OC$_2$H$_5$ | O | NHCH$_3$ | O | 0 | H | H | H |
| 189 | H | OCH$_3$ | O | NHCH$_3$ | O | 1 | 4-Cl | H | H |

-continued

| | | | | | | | | | |
|---|---|---|---|---|---|---|---|---|---|
| 193 | H | OCH₃ | O | OCH₃ | O | 1 | 2-Cl | H | H |
| 194 | H | OCH₃ | O | OCH₃ | O | 1 | 2-CH₃ | H | H |
| 195 | H | OCH₃ | O | OCH₃ | O | 1 | H | H | H |
| 196 | H | OCH₃ | O | NHCH₃ | O | 1 | 2-Cl | H | H |
| 197 | H | OCH₃ | O | NHCH₃ | O | 1 | 2-CH₃ | H | H |
| 198 | H | OCH₃ | O | NHCH₃ | O | 1 | H | H | H |
| 205 | H | OCH₃ | O | OCH₃ | O | 1 | 3-Cl | 5-Cl | H |
| 206 | H | OCH₃ | O | OCH₃ | O | 1 | 2-Cl | 4-Cl | H |
| 207 | H | OCH₃ | O | OCH₃ | O | 1 | 3-CF₃ | H | H |
| 208 | H | OCH₃ | O | OCH₃ | O | 1 | 4-OCH₃ | H | H |
| 209 | H | OCH₃ | O | OCH₃ | O | 1 | 4-CH₃ | H | H |
| 210 | H | OCH₃ | O | OCH₃ | O | 1 | 3-CH₃ | H | H |
| 211 | H | 9CH₃ | O | NHCH₃ | O | 1 | 4-CH₃ | H | H |
| 212 | H | OCH₃ | O | NHCH₃ | O | 1 | 3-CH₃ | H | H |
| 213 | H | OCH₃ | O | NHCH₃ | O | 1 | 3-Cl | 5-Cl | H |
| 214 | H | OCH₃ | O | NHCH₃ | O | 1 | 3-CF₃ | H | H |
| 215 | H | OCH₃ | O | NHCH₃ | O | 1 | 4-OCH₃ | H | H |
| 216 | H | OCH₃ | O | OCH₃ | O | 1 | 2-CH₃ | 3-CH₃ | H |
| 217 | H | OCH₃ | O | NHCH₃ | O | 1 | 2-CH₃ | 3-CH₃ | H |
| 218 | H | OCH₃ | O | OCH₃ | O | 1 | 2-CH₃ | 4-CH₃ | H |
| 219 | H | OCH₃ | O | NHCH₃ | O | 1 | 2-CH₃ | 4-CH₃ | H |
| 220 | H | OCH₃ | O | OCH₃ | O | 1 | 3-CH₃ | 4-CH₃ | H |
| 221 | H | OCH₃ | O | NHCH₃ | O | 1 | 3-CH₃ | 4-CH₃ | H |
| 222 | H | OCH₃ | O | OCH₃ | O | 1 | 3-CH₃ | 5-CH₃ | H |
| 223 | H | OCH₃ | O | NHCH₃ | O | 1 | 3-CH₃ | 5-CH₃ | H |
| 224 | H | OCH₃ | O | OCH₃ | O | 1 | 2-CH₃ | 3-CH₃ | 4-CH₃ |
| 225 | H | OCH₃ | O | NHCH₃ | O | 1 | 2-CH₃ | 3-CH₃ | 4-CH₃ |
| 226 | H | OCH₃ | O | OCH₃ | O | 1 | 2-CH₃ | 4-CH₃ | 5-CH₃ |
| 227 | H | OCH₃ | O | NHCH₃ | O | 1 | 2-CH₃ | 4-CH₃ | 5-CH₃ |
| 228 | H | OCH₃ | O | OCH₃ | O | 1 | 3-CH₃ | 4-CH₃ | 5-CH₃ |
| 229 | H | OCH₃ | O | NHCH₃ | O | 1 | 3-CH₃ | 4-CH₃ | 5-CH₃ |
| 230 | H | OCH₃ | O | OCH₃ | O | 1 | 3-Cl | H | H |
| 231 | H | OCH₃ | O | NHCH₃ | O | 1 | 3-Cl | H | H |
| 232 | H | OCH₃ | O | OCH₃ | O | 1 | 2-Br | H | H |
| 233 | H | OCH₃ | O | NHCH₃ | O | 1 | 2-Br | H | H |
| 234 | H | OCH₃ | O | OCH₃ | O | 1 | 4-Br | H | H |
| 235 | H | OCH₃ | O | NHCH₃ | O | 1 | 4-Br | H | H |
| 236 | H | OCH₃ | O | OCH₃ | O | 1 | 4-F | H | H |
| 237 | H | OCH₃ | O | NHCH₃ | O | 1 | 4-F | H | H |
| 238 | H | OCH₃ | O | OCH₃ | O | 1 | 4-I | H | H |
| 239 | H | OCH₃ | O | NHCH₃ | O | 1 | 4-I | H | H |
| 240 | H | OCH₃ | O | OCH₃ | O | 1 | 3-Cl | 4-Cl | H |
| 241 | H | OCH₃ | O | NHCH₃ | O | 1 | 3-Cl | 4-Cl | H |
| 242 | H | OCH₃ | O | OCH₃ | O | 1 | 2-Cl | 5-Cl | H |
| 243 | H | OCH₃ | O | NHCH₃ | O | 1 | 2-Cl | 5-Cl | H |
| 244 | H | OCH₃ | O | OCH₃ | O | 1 | 2-OCH₃ | H | H |
| 245 | H | OCH₃ | O | NHCH₃ | O | 1 | 2-OCH₃ | H | H |
| 246 | H | OCH₃ | O | OCH₃ | O | 1 | 3-OCH₃ | H | H |
| 247 | H | OCH₃ | O | NHCH₃ | O | 1 | 3-OCR3 | H | H |
| 248 | H | OCH₃ | O | OCH₃ | O | 1 | 3-OC₂H₅ | H | H |
| 249 | H | OCH₃ | O | NHCH₃ | O | 1 | 3-OC₂H₅ | H | H |
| 250 | H | OCH₃ | O | OCH₃ | O | 1 | 3-OCH₂CH=CH₂ | H | H |
| 251 | H | OCH₃ | O | NHCH₃ | O | 1 | 3-OCH₂CH=CH₂ | H | H |
| 252 | H | OCH₃ | O | OCH₃ | O | 1 | 4-OCH₂≡CH | H | H |
| 253 | H | OCH₃ | O | NHCH₃ | O | 1 | 4-OCH2≡CH | H | H |
| 254 | H | OCH₃ | O | OCH₃ | O | 1 | 2-OCHF₂ | H | H |
| 255 | H | OCH₃ | O | NHCH₃ | O | 1 | 2-OCHF₂ | H | H |
| 256 | H | OCH₃ | O | OCH₃ | O | 1 | 4-OCHF₂ | H | H |
| 257 | H | OCH₃ | O | NHCH₃ | O | 1 | 4-OCHF₂ | H | H |
| 258 | H | OCH₃ | O | OCH₃ | O | 1 | 3-OPh | H | H |
| 259 | H | OCH₃ | O | NHCH₃ | O | 1 | 3-OPh | H | H |
| 260 | H | OCH₃ | O | OCH₃ | O | 1 | 3-OCH₃ | 4-OCH₃ | H |
| 261 | H | OCH₃ | O | NHCH₃ | O | 1 | 3-OCH₃ | 4-OCH₃ | H |
| 262 | H | OCH₃ | O | NHCH₃ | O | 1 | 2-Cl | 4-Cl | H |
| 263 | H | OCH₃ | O | OCH₃ | O | 1 | 2-CH₃ | 4-Cl | H |
| 264 | H | OCH₃ | O | OCH₃ | O | 1 | 2-CH₃ | 4-Br | H |
| 265 | H | OCH₃ | O | NHCH₃ | O | 1 | 2-CH₃ | 4-Br | H |
| 266 | H | OCH₃ | O | OCH₃ | O | 1 | 2-Cl | 4-CH₃ | H |
| 267 | H | OCH₃ | O | NHCH₃ | O | 1 | 2-Cl | 4-CH₃ | H |
| 268 | H | OCH₃ | O | OCH₃ | O | 1 | 3-CH₃ | 4-Cl | H |
| 269 | H | OCH₃ | O | NHCH₃ | O | 1 | 3-CH₃ | 4Cl | H |
| 270 | H | OCH₃ | O | OCH₃ | O | 1 | 2-CH₃ | 3-CH₃ | 4-Cl |
| 271 | H | OCH₃ | O | NHCH₃ | O | 1 | 2-CH₃ | 3-CH₃ | 4-Cl |
| 272 | H | OCH₃ | O | NHCH₃ | O | 1 | 3-Cl | 4-CH₃ | 5-Cl |
| 273 | H | OCH₃ | O | NHCH₃ | O | 1 | 2-Cl | 5-CF₃ | H |
| 274 | H | OCH₃ | O | NHCH₃ | O | 1 | 2-Cl | 4-OCH₃ | H |
| 275 | H | OCH₃ | O | NHCH₃ | O | 1 | 2-Br | 4-OCH₃ | H |
| 276 | H | OCH₃ | O | NHCH₃ | O | 1 | 3-Cl | 4-OCH₃ | H |
| 277 | H | OCH₃ | O | NHCH₃ | O | 1 | 3-OCH₃ | 4-Cl | H |

-continued

| | | | | | | | | |
|---|---|---|---|---|---|---|---|---|
| 278 | H | OCH₃ | O | NHCH₃ | O | 1 | 3-Cl | 4-OCH₃ | 5-Cl |
| 279 | H | OCH₃ | O | NHCH₃ | O | 1 | 2-Cl | 4-OCHF₂ | H |
| 280 | H | OCH₃ | O | NHCH₃ | O | 1 | 3-Cl | 4-OCHF₂ | H |
| 281 | H | OCH₃ | O | NHCH₃ | O | 1 | 2-CH₃ | 4-OCH₃ | H |
| 282 | H | OCH₃ | O | NHCH₃ | O | 1 | 2-OCH₃ | 4-CH₃ | H |
| 283 | H | OCH₃ | O | NHCH₃ | O | 1 | 2-CH₃ | 4-OCHF₂ | H |
| 285 | H | OCH₃ | O | OCH₃ | O | 0 | 4-Cl | H | H |
| 286 | H | OCH₃ | O | NHCH₃ | O | 0 | 4-Cl | H | H |
| 288 | H | OCH₃ | O | OCH₃ | O | 0 | 4-CH₃ | H | H |
| 289 | H | OCH₃ | O | NHCH₃ | O | 0 | 4-CH₃ | H | H |
| 291 | H | OCH₃ | O | OCH₃ | O | 0 | 3-CH₃ | 4-CH₃ | H |
| 292 | H | OCH₃ | O | NHCH₃ | O | 0 | 3-CH₃ | 4-CH₃ | H |
| 293 | H | OCH₃ | O | NHCH₃ | O | 0 | 2-CH₃ | H | H |
| 294 | H | OCH₃ | O | OCH₃ | O | 0 | 3-CH₃ | H | H |
| 295 | H | OCH₃ | O | NHCH₃ | O | 0 | 3-CH₃ | H | H |
| 296 | H | OCH₃ | O | OCH₃ | O | 0 | 3-CH₃ | 5-CH₃ | H |
| 297 | H | OCH₃ | O | NHCH₃ | O | 0 | 3-CH₃ | 5-CH₃ | H |
| 298 | H | OCH₃ | O | NHCH₃ | O | 0 | 3-CH₃ | 4-CH₃ | 5-CH₃ |
| 299 | H | OCH₃ | O | NHCH₃ | O | 0 | 4-C₂H₅ | H | H |
| 300 | H | OCH₃ | O | OCH₃ | O | 0 | 3-CF₃ | H | W |
| 301 | H | OCH₃ | O | NHCH₃ | O | 0 | 3-CF₃ | H | H |
| 302 | H | OCH₃ | O | OCH₃ | O | 0 | 3-Cl | H | H |
| 303 | H | OCH₃ | O | NHCH₃ | O | 0 | 3-Cl | H | H |
| 304 | H | OCH₃ | O | OCH₃ | O | 0 | 3-Br | H | H |
| 305 | H | OCH₃ | O | NHCH₃ | O | 0 | 3-Br | H | W |
| 306 | H | OCH₃ | O | OCH₃ | O | 0 | 4-Br | H | H |
| 307 | H | OCH₃ | O | NHCH₃ | O | 0 | 4-Br | H | H |
| 308 | H | OCH₃ | O | OCH₃ | O | 0 | 4-F | H | H |
| 309 | H | OCH₃ | O | NHCH₃ | O | 0 | 4-F | H | H |
| 310 | H | OCH₃ | O | NHCH₃ | O | 0 | 4-I | H | H |
| 311 | H | OCH₃ | O | NHCH₃ | O | 0 | 3-Cl | 4-Cl | H |
| 312 | H | OCH₃ | O | NHCH₃ | O | 0 | 2-Cl | H | H |
| 313 | H | OCH₃ | O | NHCH₃ | O | 0 | 3-OCH₃ | H | H |
| 314 | H | OCH₃ | O | NHCH₃ | O | 0 | 3-OC₃H₇ | H | H |
| 315 | H | OCH₃ | O | OCH₃ | O | 0 | 4-OCH₃ | H | H |
| 316 | H | OCH₃ | O | NHCH₃ | O | 0 | 4-OCH₃ | H | H |
| 317 | H | OCH₃ | O | NHCH₃ | O | 0 | 4-OC₂H₅ | H | H |
| 318 | H | OCH₃ | O | NHCH₃ | O | 0 | 3-OCH₃ | 4-OCH₃ | H |
| 319 | H | OCH₃ | O | NHCH₃ | O | 0 | 6 3-OCHF₂ | H | H |
| 320 | H | OCH₃ | O | NHCH₃ | O | 0 | 4-OCHF₂ | H | H |
| 321 | H | OCH₃ | O | NHCH₃ | O | 0 | 3-OCH₂CH=CH₂ | H | H |
| 322 | H | OCH₃ | O | NHCH₃ | O | 0 | 4-OCH₂CH=CH₂ | H | H |
| 323 | H | OCH₃ | O | NHCH₃ | O | 0 | 3-OCH₂C≡CH | H | H |
| 324 | H | OCH₃ | O | NHCH₃ | O | 0 | 3-OCH₂C≡CCH₃ | H | H |
| 325 | H | OCH₃ | O | NHCH₃ | O | 0 | 4-OCH₂C≡CH | H | H |
| 326 | H | OCH₃ | O | NHCH₃ | O | 0 | 3-OPh | H | H |
| 327 | H | OCH₃ | O | NHCH₃ | O | 0 | 4-OPh | H | H |
| 328 | H | OCH₃ | O | OCH₃ | O | 0 | 3-CH₃ | 4-Cl | H |
| 329 | H | OCH₃ | O | NHCH₃ | O | 0 | 3-CH₃ | 4-Cl | H |
| 330 | H | OCH₃ | O | NHCH₃ | O | 0 | 3-Cl | 4-CH₃ | H |
| 331 | H | OCH₃ | O | NHCH₃ | O | 0 | 2-Cl | 5-CF₃ | H |
| 332 | H | OCH₃ | O | NHCH₃ | O | 0 | 3-CH₃ | 4-OCH₃ | H |
| 333 | H | OCH₃ | O | NHCH₃ | O | 0 | 3-OCH₃ | 4-CH₃ | H |
| 334 | H | OCH₃ | O | NHCH₃ | O | 0 | 3-CH₃ | 4-OCHF₂ | H |
| 335 | H | OCH₃ | O | NHCH₃ | O | 0 | 3-OCHF₂ | 4-CH₃ | H |
| 336 | H | OCH₃ | O | NHCH₃ | O | 0 | 3-OCH₃ | 4-Cl | H |
| 337 | H | OCH₃ | O | NHCH₃ | O | 0 | 3-Cl | 4-OCH₃ | H |
| 338 | H | OCH₃ | O | NHCH₃ | O | 0 | 3-OCHF₂ | 4-Cl | H |
| 339 | H | OCH₃ | O | NHCH₃ | O | 0 | 3-Cl | 4-OCHF₂ | H |
| 340 | H | OCH₃ | O | NHCH₃ | O | 0 | 2-Cl | 4-CH₃ | 5-OCH₃ |
| 341 | H | OCH₃ | O | NHCH₃ | O | 0 | 3-CH₂CH=CH₂ | 4-CH₃ | H |
| 342 | H | OCH₃ | O | NHCH₃ | O | 0 | 3-CH₃ | 4-OCH₂C≡CH | H |
| 343 | H | OCH₃ | O | NHCH₃ | O | 0 | 3-CH₂CH=CH₂ | 4-Cl | H |
| 344 | H | OCH₃ | O | NHCH₃ | O | 0 | 3-Cl | 4-OCH₂C≡CH | H |
| 345 | 4-Cl | OCH₃ | O | NHCH₃ | O | 1 | 2-CH₃ | 5-CH₃ | H |
| 346 | 5-Cl | OCH₃ | O | NHCH₃ | O | 1 | 2-CH₃ | 5-CH₃ | H |
| 347 | CH₃ | OCH₃ | O | NHCH₃ | O | 1 | 2-CH₃ | 5-CH₃ | H |
| 348 | CH₃ | OCH₃ | O | NHCH₃ | O | 1 | 2-CH₃ | 5-CH₃ | H |
| 349 | OCH₃ | OCH₃ | O | NHCH₃ | O | 1 | 2-CH₃ | 5-CH₃ | H |
| 350 | OCH₃ | OCH₃ | O | NHCH₃ | O | 1 | 2-CH₃ | 5-CH₃ | H |
| 351 | H | OCH₂C≡CH | O | NHCH₃ | O | 1 | 2-CH₃ | 5-CH₃ | H |
| 352 | H | OCHF₂ | O | NHCH₃ | O | 1 | 2-CH₃ | 5-CH₃ | H |
| 353 | H | OCOSCH₃ | O | NHCH₃ | O | 1 | 2-CH₃ | 5-CH₃ | H |
| 354 | H | OSO₂CH₃ | O | NHCH₃ | O | 1 | 2-CH₃ | 5-CH₃ | H |
| 355 | H | OSO₂Ph-4-CH₃ | O | NHCH₃ | O | 1 | 2-CH₃ | 5-CH₃ | H |
| 356 | H | OCONHCH₃ | O | NHCH₃ | O | 1 | 2-CH₃ | 5-CH₃ | H |
| 357 | H | OCON(CH₃)₂ | O | NHCH₃ | O | 1 | 2-CH₃ | 5-CH₃ | H |
| 358 | H | SOCH₃ | O | OCH₃ | O | 1 | 2-CH₃ | 5-CH₃ | H |
| 359 | H | SO₂CH₃ | O | OCH₃ | O | 1 | 2-CH₃ | 5-CH₃ | H |

-continued

| | | | | | | | | | |
|---|---|---|---|---|---|---|---|---|---|
| 360 | H | SOCH$_3$ | O | NHCH$_3$ | O | 1 | 2-CH$_3$ | 5-CH$_3$ | H |
| 361 | H | SO$_2$CH$_3$ | O | NHCH$_3$ | O | 1 | 2-CH$_3$ | 5-CH$_3$ | H |
| 362 | H | NHCH$_3$ | O | NHCH$_3$ | O | 1 | 2-CH$_3$ | 5-CH$_3$ | H |
| 363 | H | N(CH$_3$)$_2$ | O | NHCH$_3$ | O | 1 | 2-CH$_3$ | 5-CH$_3$ | H |
| 364 | H | NO$_2$ | O | NHCH$_3$ | O | 1 | 2-CH$_3$ | 5-CH$_3$ | H |
| 365 | H | NO$_2$ | O | NHCH$_3$ | O | 0 | H | H | H |
| 366 | H | OCH$_3$ | O | NHCH$_3$ | S | 1 | 2-CH$_3$ | 5-CH$_3$ | H |
| 367 | H | OCH$_3$ | O | NHCH$_3$ | NH | 1 | 2-CH$_3$ | 5-CH$_3$ | H |
| 368 | H | OCH$_3$ | O | NHCH$_3$ | NCH$_3$ | 1 | 2-CH$_3$ | 5-CH$_3$ | H |
| 369 | H | OCH$_3$ | O | NHCH$_3$ | NCHO | 1 | 2-CH$_3$ | 5-CH$_3$ | H |
| 370 | H | OCH$_3$ | O | NHCH$_3$ | NCOCH$_3$ | 1 | 2-CH$_3$ | 5-CH$_3$ | H |
| 371 | H | OCH$_3$ | S | NHCH$_3$ | O | 1 | 2-CH$_3$ | H | H |
| 372 | H | OCH$_3$ | S | NHCH$_3$ | O | 1 | 2-CH$_3$ | 4-Cl | H |
| 373 | H | SCH$_3$ | O | NHCH$_3$ | O | 1 | 2-CH$_3$ | H | H |
| 374 | H | SCH$_3$ | O | NHCH$_3$ | O | 1 | 2-CH$_3$ | 4-Cl | H |
| 375 | H | OC$_2$H$_5$ | O | NHCH$_3$ | O | 1 | 2-CH$_3$ | H | H |
| 376 | H | OC$_2$H$_5$ | O | NHCH$_3$ | O | 1 | 2-CH$_3$ | 4-Cl | H |
| 377 | H | SCH$_3$ | O | NHCH$_3$ | O | 0 | H | H | H |
| 379 | H | SCH$_3$ | O | NHCH$_3$ | O | 0 | 4-CH$_3$ | H | H |
| 380 | H | OCH$_3$ | O | NHCH$_3$ | O | 1 | 4-SCH$_3$ | H | H |
| 381 | H | OCH$_3$ | O | NHCH$_3$ | S | 1 | 2-CH$_3$ | H | H |
| 382 | H | OCH$_3$ | O | NHCH$_3$ | S | 1 | 2-CH$_3$ | 4-Cl | H |
| 383 | H | OCH$_3$ | O | NHCH$_3$ | O | 1 | 4-SCH$_3$ | H | H |
| 384 | H | CH$_3$ | O | NHCH$_3$ | O | 1 | 2-CH$_3$ | 5-CH$_3$ | H |
| 385 | H | OCOC$_2$H$_5$ | O | NHCH$_3$ | O | 1 | 2-CH$_3$ | 5-CH$_3$ | H |
| 386 | H | OCH$_3$ | O | NHC$_2$H$_5$ | O | 1 | 2-CH$_3$ | 5-CH$_3$ | H |
| 387 | H | OCH$_3$ | O | NH$_2$ | O | 1 | 2-CH$_3$ | H | H |
| 388 | H | OCH$_3$ | O | NH$_2$ | O | 1 | 2-CH$_3$ | 4-Cl | H |

| Comp. No. | X | R$^1$ | Z | Y | M | n | Q |
|---|---|---|---|---|---|---|---|
| 389 | H | OCH$_3$ | O | NHCH$_3$ | O | 0 | 6-Cl-pyrimidin-4-yl |
| 390 | H | OCH$_3$ | O | NHCH$_3$ | O | 0 | 4,6-(CH$_3$)$_2$-pyrimidin-2-yl |
| 391 | H | OCH$_3$ | O | NHCH$_3$ | O | 0 | 3,5-Cl$_2$-pyridin-2-yl |
| 392 | H | OCH$_3$ | O | NHCH$_3$ | O | 0 | 5-Cl-pyridin-2-yl |
| 393 | H | OCH$_3$ | O | NHCH$_3$ | O | 0 | 5-CF$_3$-pyridin-2-yl |
| 394 | H | OCH$_3$ | O | NHCH$_3$ | O | 0 | 5-CF$_3$-6-Cl-pyridin-2-yl |
| 395 | H | OCH$_3$ | O | NHCH$_3$ | O | 0 | Quinolin-4-yl |
| 396 | H | OCH$_3$ | O | NHCH$_3$ | O | 0 | Quinazolin-4-yl |
| 397 | H | OCH$_3$ | O | NHCH$_3$ | O | 0 | Benzothiazol-2-yl |
| 398 | H | OCH$_3$ | O | OCH$_3$ | O | 1 | Benzothiazol-2-yl |
| 399 | H | OCH$_3$ | O | NHCH$_3$ | O | 1 | Benzothiazol-2-yl |
| 400 | H | OCH$_3$ | O | OCH$_3$ | O | 1 | Quinolin-4-yl |
| 401 | H | OCH$_3$ | O | NHCH$_3$ | O | 1 | Quinolin-4-yl |
| 402 | H | OCH$_3$ | O | OCH$_3$ | O | 1 | Quinazolin-4-yl |
| 403 | H | OCH$_3$ | O | NHCH$_3$ | O | 1 | Quinazolin-4-yl |
| 404 | H | OCH$_3$ | O | OCH$_3$ | O | 1 | 1,3-(CH$_3$)$_2$-4-CO$_2$CH$_3$-pyrazo-1-5-yl |
| 405 | H | OCH$_3$ | O | NHCH$_3$ | O | 1 | 1,3-(CH$_3$)$_2$-4-CO$_2$CH$_3$-pyrazol-5-yl |
| 406 | H | OCH$_3$ | O | OCH$_3$ | O | 1 | 1-CH$_3$-4-CHO-pyrazol-5-yl |
| 407 | H | OCH$_3$ | O | NHCH$_3$ | O | 1 | 1-CH$_3$-4-CHO-pyrazol-5-yl |
| 408 | H | OCH$_3$ | O | OCH$_3$ | O | 1 | 5-CO$_2$C$_2$H$_5$-6-C$_2$H$_5$-pyrimidin-4-yl |
| 409 | H | OCH$_3$ | O | NHCH$_3$ | O | 1 | 5-CO$_2$C$_2$H$_5$-6-C$_2$H$_5$-pyrimidin-4-yl |
| 410 | H | OCH$_3$ | O | OCH$_3$ | O | 1 | 4,6-(CH$_3$)$_2$-pyrimidin-2-yl |
| 411 | H | OCH$_3$ | O | NHCH$_3$ | O | 1 | 4,6-(CH$_3$)$_2$-pyrimidin-2-yl |
| 412 | H | OCH$_3$ | O | OCH$_3$ | O | 1 | 6-Cl-pyrimidin-4-yl |
| 413 | H | OCH$_3$ | O | NHCH$_3$ | O | 1 | 6-Cl-pyrimidin-4-yl |
| 414 | H | OCH$_3$ | O | OCH$_3$ | O | 1 | 5-Cl-6-CH$_3$-pyrimidin-4-yl |
| 415 | H | OCH$_3$ | O | NHCH$_3$ | O | 1 | 5-Cl-6-CH$_3$-pyrimidin-4-yl |
| 416 | H | OCH$_3$ | O | OCH$_3$ | O | 1 | 5-CF$_3$-6-Cl-pyridin-2-yl |
| 417 | H | OCH$_3$ | O | NHCH$_3$ | O | 1 | 5-CF$_3$-6-Cl-pyridin-2-yl |
| 418 | H | OH | O | NHCH$_3$ | O | 1 | 3-CF$_3$-6-Cl-pyridin-2-yl |
| 419 | H | OCH$_3$ | O | OCH$_3$ | O | 1 | 3-CF$_3$-6-Cl-pyridin-2-yl |
| 420 | H | OCH$_3$ | O | NHCH$_3$ | O | 1 | 3-CF$_3$-6-Cl-pyridin-2-yl |
| 421 | H | OH | O | NHCH$_3$ | O | 1 | 3-CF$_3$-pyridin-2-yl |
| 422 | H | OCH$_3$ | O | OCH$_3$ | O | 1 | 3-CF$_3$-pyridin-2-yl |
| 423 | H | OCH$_3$ | O | NHCH$_3$ | O | 1 | 3-CF$_3$-pyridin-2-yl |
| 425 | H | OH | O | NHCH$_3$ | O | 1 | 3-Cl-5-CF$_3$-pyridin-2-yl |
| 426 | H | OCH$_3$ | O | OCH$_3$ | O | 1 | 3-Cl-5-CF$_3$-pyridin-2-yl |
| 427 | H | OCH$_3$ | O | NHCH$_3$ | O | 1 | 3-Cl-5-CF$_3$-pyridin-2-yl |
| 428 | H | OH | O | NHCH$_3$ | O | 1 | 5-CF$_3$-pyridin-2-yl |
| 429 | H | OCH$_3$ | O | NHCH$_3$ | O | 1 | 5-CF$_3$-pyridin-2-yl |
| 430 | H | OCH$_3$ | O | OCH$_3$ | O | 1 | 5-CF$_3$-pyridin-2-yl |

-continued

| | | | | | | | |
|---|---|---|---|---|---|---|---|
| 431 | H | OH | O | NHCH₃ | O | 1 | 3,5-Cl₂-pyridin-2-yl |
| 432 | H | OCH₃ | O | OCH₃ | O | 1 | 3,5-Cl₂-pyridin-2-yl |
| 433 | H | OCH₃ | O | NHCH₃ | O | 1 | 3,5-Cl₂-pyridin-2-yl |
| 434 | H | OH | O | NHCH₃ | O | 1 | 2-Cl-pyridin-3-yl |
| 436 | H | OCH₃ | O | OCH₃ | O | 1 | 2-Cl-pyridin-3-yl |
| 437 | H | OCH₃ | O | NHCH₃ | O | 1 | 2-Cl-pyridin-3-yl |

| Comp. No. | X | R¹ | Z | Y | M | n | U | V | W |
|---|---|---|---|---|---|---|---|---|---|
| 438 | H | OCH₃ | O | NHCH₃ | O | 1 | 4-CH₂OCH₃ | H | H |
| 439 | H | NO₂ | O | OCH₃ | O | 1 | 2-CH₃ | 5-CH₃ | H |

| Comp. No. | X | R¹ | Z | Y | M | n | Q |
|---|---|---|---|---|---|---|---|
| 441 | H | OH | O | NHCH₃ | O | 1 | 5-CF₃-6-Cl-pyridin-2-yl |
| 443 | H | OCH₃ | O | NHCH₃ | O | 1 | 5-Cl-pyridin-2-yl |
| 446 | H | OH | O | NHCH₃ | O | 1 | 3-CF₃-5-Cl-pyridin-2-yl |
| 447 | H | OCH₃ | O | OCH₃ | O | 1 | 3-CF₃-5-Cl-pyridin-2-yl |
| 448 | H | OCH₃ | O | NHCH₃ | O | 1 | 3-CF₃-5-Cl-pyridin-2-yl |
| 451 | H | OH | O | NHCH₃ | O | 1 | 6-CF₃-pyridin-2-yl |
| 452 | H | OCH₃ | O | OCH₃ | O | 1 | 6-CF₃-pyridin-2-yl |
| 453 | H | OCH₃ | O | NHCH₃ | O | 1 | 6-CF₃-pyridin-2-yl |
| 454 | H | OCH₃ | O | OCH₃ | O | 1 | 5-Cl-pyridin-2-yl |
| 455 | H | OH | O | NHCH₃ | O | 1 | 5-Cl-pyridin-2-yl |
| 457 | H | OH | O | NHCH₃ | O | 1 | 5-CF₃-3,6-Cl₂-pyridin-2-yl |
| 458 | H | OCH₃ | O | OCH₃ | O | 1 | 5-CF₃-3,6-Cl₂-pyridin-2-yl |
| 459 | H | OCH₃ | O | NHCH₃ | O | 1 | 5-CF₃-3,6-Cl₂-pyridin-2-yl |

| Comp. No. | X | R¹ | Z | Y | M | n | U | V | W |
|---|---|---|---|---|---|---|---|---|---|
| 460 | H | OCH₃ | S | NH₂ | O | 1 | 2-CH₃ | 5-CH₃ | H |
| 461 | H | OC₄H₉ | S | NHCH₃ | O | 1 | 2-CH₃ | 5-CH₃ | H |
| 462 | H | NH₂·HCl | O | NHCH₃ | O | 1 | 2-CH₃ | 5-CH₃ | H |
| 463 | H | NH₂·HCl | O | OCH₃ | O | 1 | 2-CH₃ | 5-CH₃ | H |
| 465 | H | OCH₃ | O | NHCH₃ | O | 1 | 2-CH₃ | 3-CH₃ | 5-CH₃ |

| Comp. No. | X | R¹ | Z | Y | M | n | Q |
|---|---|---|---|---|---|---|---|
| 466 | H | OCH₃ | O | NHCH₃ | O | 1 | 3-Cl-pyridin-2-yl |
| 467 | H | OCH₃ | O | NHCH₃ | O | 1 | 3-CH₃-pyridin-2-yl |
| 468 | H | OCH₃ | O | NHCH₃ | S | 1 | 3,5-Cl₂-pyridin-2-yl |

| Comp. No. | X | R¹ | Z | Y | M | n | U | V | W |
|---|---|---|---|---|---|---|---|---|---|
| 469 | H | OCH₃ | O | N(CH₃)C₂H₅ | O | 1 | 2-CH₃ | 4-Cl | H |
| 470 | H | OCH₃ | O | OH | O | 1 | 2-CH₃ | 5-CH₃ | H |
| 471 | H | OCH₃ | S | N(CH₃)₂ | O | 1 | 2-CH₃ | H | H |
| 472 | H | OCH₃ | O | NCH₃ | O | 1 | 2-Cl | 5-CH₃ | H |
| 473 | H | OCH₃ | O | NCH₃ | O | 1 | 2-CH₃ | 6-CH₃ | H |

| Comp. No. | mp or ¹H-NMR(CDCl₃) δ ppm |
|---|---|
| 139 | 2.21(3H, s), 2.33(3H, s), 3.40(3H, s), 3.70(3H, s), 5.10(1H, d, J=12.2), 5.14(1H, s), 5.28(1H, d, J=12.2), 6.71(1H, d, J=7.3), 6.76(1H, s), 7.04(1H, d, J=7.3), 7.33–7.40(2H, m), 7.50–7.56 (2H, m) |
| 140 | 86–88° C. |
| 141 | 2.23(3H, s), 2.32(3H, s), 3.36(3H, s), 3.71(3H, s), 4.67(1H, d, J=6.7), 4.75(1H, d, J=6.7), 5.17(1H, d, J=12.2), 5.23(1H, d, J=12.2), 5.49(1H, s), 6.71(1H, d, J=7.9), 6.75(1H, s), 7.04(1H, d, J=7.3), 7.34–7.40(2H, m), 7.53–7.57(2H, m) |
| 142 | 81–82° C. |
| 143 | 77–80° C. |
| 144 | 114–115° C. |
| 145 | 62–65° C. |
| 146 | 108–110° C. |
| 149 | 2.20(3H, s), 2.35(3H, s), 3.76(3H, s), 5.14(2H, s), 5.84(1H, s), 6.73(1H, d, J=7.3), 6.77(1H, s), 7.05(1H, d, J=7.3), 7.38–7.48(3H, m), 7.66(1H, d, J=7.3) |
| 150 | 111–113° C. |
| 151 | 1.26(3H, t, J=7.3), 2.21(3H, s), 2.32(3H, s), 3.42–3.67(2H, m), 3.70(3H, s), 5.12(1H, d, J=12.2), 5.23(1H, s), 5.28(1H, d, J=12.2), 6.70(1H, d, J=7.3), 6.75(1H, s), 7.04(1H, d, J=7.3), 7.32–7.38(2H, m), 7.49–7.58(2H, m) |
| 152 | 0.89(3H, t, J=7.3), 1.32–1.45(2H, m), 1.57–1.68(2H, m), 2.22(3H, s), 2.33(3H, s), 3.39–3.47(1H, m), 3.52–3.60(1H, m), 3.70(3H, s), 5.12(1H, d, J=12.2), 5.20(1H, s), 5.27(1H, d, J=12.2), 6.71(1H, d, |

-continued

| Comp. No. | mp or ¹H-NMR(CDCl₃) δ ppm |
|---|---|
| | J=7.9), 6.75(1H, s), 7.04(1H, d, J=7.3), 7.34–7.39(2H, m), 7.52–7.55(2H, m) |
| 155 | 98–100° C. |
| 156 | 58–60° C. |
| 159 | 100–101° C. |
| 161 | 2.19(3H, s), 2.32(3H, s), 3.36(3H, s), 5.02(1H, s), 5.07(1H, d, J=11.6), 5.40(1H, d, J=11.6), 5.88(1H, brs), 6.70(1H, d, J=7.3), 6.71(1H, brs), 6.78(1H, s), 7.03(1H, d, J=7.3), 7.32–7.40(2H, m), 7.42–7.48(1H, m), 7.50–7.53(1H, m) |
| 162 | 2.10(3H, s), 2.20(3H, s), 2.34(3H, s), 3.71(3H, s), 4.95(1H, s), 5.13(1H, s), 6.72(1H, d, J=7.3), 6.77(1H, s), 7.04(1H, d, J=7.3), 7.30–7.40(2H, m), 7.46(1H, dd, J=7.3, 1.8), 7.68(1H, dd, J=7.3, 1.8) |
| 163 | 62–62.5° C. |
| 165 | 2.17(3H, s), 2.33(3H, s), 2.87(3H, s), 3.00(3H, s), 3.44(3H, s), 5.02(1H, d, J=11.6), 5.26(1H, d, J=11.6), 5.32(1H, s), 6.71(1H, d, J=7.3), 6.79(1H, s), 7.03(1H, d, J=7.3), 7.30–7.40(3H, m), 7.50–7.54(1H, m) |
| 166 | 80–81° C. |
| 170 | 2.20(3H, s), 2.32(3H, s), 3.23(3H, d, J=4.8), 3.35(3H, s), 5.12(1H, d, J=11.6), 5.40(1H, s), 5.58(1H, d, J=11.6), 6.70(1H, d, J=7.3), 6.81(1H, s), 7.03(1H, d, J=7.3), 7.28–7.38(3H, m), 7.48–7.52(1H, m), 8.78(1H, brs) |
| 171 | 2.10(3H, s), 2.78(3H, d, J=4.8), 6.18(1H, brs), 6.34(1H, s), 6.87(1H, dd, J=8.2, 1.0), 6.97–7.00(2H, m), 7.11–7.16(2H, m), 7.26–7.36(3H, m), 7.58(1H, dd, J=7.8, 1.7) |
| 173 | 2.15(3H, s), 2.25(3H, s), 2.74(3H, d, J=4.9), 5.10(1H, d, J=11.9), 5.44(1H, d, J=11.9), 6.29(1H, brs), 6.36(1H, s), 6.91(1H, t, J=7.3), 6.98(1H, d, J=7.3), 7.14–7.19(2H, m), 7.34–7.40(2H, m), 7.46–7.56(2H, m) |
| 174 | 3.39(3H, s), 3.70(3H, s), 5.05(1H, s), 5.09(1H, d, J=12.0), 5.25(1H, d, J=12.0), 6.86–6.92(2H, m), 7.22–7.26(2H, m), 7.35–7.38(2H, m), 7.45–7.49(2H, m) |
| 175 | 1.11(3H, t, J=7.3), 1.99(2H, quintet, J=7.3), 3.81(3H, s), 4.24(1H, t, J=7.3), 6.74(1H, dd, J=7.9, 1.2), 6.87–6.97(4H, m), 7.11(1H, ddd, J=7.9, 7.6, 1.2), 7.21(1H, ddd, J=7.9, 7.6, 1.8), 7.49(1H, dd, J=7.6, 1.8) |
| 176 | 2.20(3H, s), 2.23(3H, s), 2.32(3H, s), 3.46(3H, s), 5.05(1H, d, J=12.2), 5.15(1H, s), 5.34(1H, d, J=12.2), 6.70(1H, d, J=7.3), 6.76(1H, s), 7.03(1H, d, J=7.3), 7.32–7.40(2H, m), 7.47–7.57(2H, m) |
| 177 | 65–67° C. |
| 178 | 2.12(3H, s), 2.23(6H, s), 2.78(3H, d, J=4.9), 6.26(1H, brs), 6.36(1H, s), 6.72(1H, dd, J=7.9, 1.8), 6.80(1H, s), 6.82(1H, d, J=7.9), 7.09(2H, t, J=7.3), 7.25(1H, dt, J=1.8, 7.9), 7.56(1H, dd, J=7.3, 1.8) |
| 179 | 98–99.5° C. |
| 180 | 0.91(3H, t, J=7.3), 1.65–1.92(1H, m), 2.04–2.17(1H, m), 3.61(3H, s), 3.78(3H, s), 3.98(1H, t, J=7.3), 6.78(1H, dd, J=7.9, 1.8), 6.82–6.93(4H, m), 7.05(1H, t, J=7.3), 7.15(1H, dt, J=7.9, 1.8), 7.35(1H, dd, J=7.3, 1.8) |
| 181 | 39–41° C. |
| 182 | 3.41(3H, s), 3.66(3H, s), 5.24(1H, s), 6.90(1H, d, J=7.9), 6.99(2H, d, J=7.9), 7.10(1H, t, J=7.3), 7.25–7.36(3H, m), 7.52(1H, dd, J=7.9, 1.8) |
| 183 | 1.21(3H, t, J=7.3), 3.44–3.65(2H, m), 3.64(3H, s), 5.35(1H, s), 6.88(1H, d, J=7.9), 6.98(2H, d, J=7.9), 7.08(1H, t, J=7.3), 7.14(1H, t, J=7.3), 7.23–7.34(3H, m), 7.55(1H dd, J=7.9, 1.8) |
| 184 | 2.82(3H, d, J=4.9), 3.35(3H, s), 5.03(1H, s), 6.82(1H, brs), 6.88(1H, d, J=7.9), 7.04(2H, d, J=7.9), 7.12(2H, t, J=7.9), 7.23–7.42(4H, m) |
| 185 | 1.20(3H, d, J=7.3), 2.24(3H, s), 3.40(3H, s), 4.08–4.27(2H, m), 5.06(1H, s), 5.14(1H, d, J=12.2), 5.29(1H, d, J=12.2), 6.83(1H, d, J=7.9), 7.08–7.13(2H, m), 7.33–7.39(2H, m), 7.47–7.55(2H, m) |
| 186 | 111–113° C. |
| 188 | 1.16(3H, t, J=7.3), 2.82(3H, d, J=4.9), 3.50(2H, q, J=7.3), 5.15(1H, s), 6.86(1H, d, J=7.9), 6.90(1H, brs), 7.03(2H, d, J=7.9), 7.09(2H, t, J=7.9), 7.20–7.37(4H, m) |
| 189 | 87–88° C. |
| 193 | 3.42(3H, s), 3.70(3H, s), 5.15(1H, s), 5.20(1H, d, J=12.0), 5.39(1H, d, J=12.0), 6.93(1H, dt, J=1.8, 8.0), 7.03(1H, d, J=8.0), 7.21(1H, dt, J=1.8, 8.0), 7.36–7.40(3H, m), 7.51–7.59(2H, m) |
| 194 | 2.26(3H, s), 3.40(3H, s), 3.70(3H, s), 5.13(1H, s), 5.13(1H, d, J=12.0), 5.30(1H, d, J=12.0), 6.89–6.94(2H, m), 7.10–7.20(2H, m), 7.35–7.40(2H, m), 7.50–7.52(2H, m) |
| 195 | 3.40(3H, s), 3.70(3H, s), 5.11(1H, s), 5.11(1H, d, J=12.0), 5.30(1H, d, J=12.0), 6.90–7.00(3H, m), 7.25–7.38(4H, m), 7.47–7.51(2H, m) |
| 196 | 86–87° C. |
| 197 | 91–92° C. |
| 198 | 2.81(3H, s), 3.35(3H, s), 5.00(1H, s), 5.08(1H, d, J=12.0), 5.48(1H, d, J=12.0), 6.80(1H, brs), 6.93–6.97(3H, m), 7.25–7.49(6H, m) |
| 205 | 69–72° C. |
| 206 | 3.41(3H, s), 3.72(3H, s), 5, 10(1H, s), 5, 18(1H, d, J=12.0), 5.34(1H, d, J=12.0), 6.92(1H, d, J=8.6), 6.17(1H, dd, J=9.0, 24), 7.36–7.40(2H, m), 7.50–7.56(2H, m) |
| 207 | 3.41(3H, s), 3.71(3H, s), 5.06(1H, s), 5.16(1H, d, J=12.0), 5.34(1H, d, J=12.0), 7.17(1H, m), 7.22–7.30(2H, m), 7.38–7.42(3H, m), 7.47–7.52(2H, m) |
| 208 | 3.39(3H, s), 3.70(3H, s), 3.77(3H, s), 5.04(1H, d, J=12.0), 5.11(1H, s), 5.24(1H, d, J=12.0), 6.80–6.88(2H, m), 6.90–6.95(2H, m), 7.30–7.40(2H, m), 7.45–7.55(2H, m) |
| 209 | 2.29(3H, s), 3.39(3H, s), 3.70(3H, s), 5.07(1H, d, J=12.0), 5.11(1H, s), 5.27(1H, d, J=12.0), 6.89(2H, d, J=18.6), 7.09(1H, t, J=8.6), 7.30–7.40(2H, m), 7.45–7.51(2H, m) |
| 210 | 2.34(3H, s), 3.40(3H, s), 3.70(3H, s), 5.08(1H, d, J=12.0), 5.11(1H, s), 5.28(1H, d, J=12.0), 6.89(2H, d, J=8.6), 6.91(1H, s), 7.18(1H, t, J=8.0), 7.32–7.40(2H, m), 7.45–7.55(2H, m) |
| 211 | 98–100° C. |
| 212 | 2.33(3H, s), 2.82(3H, d, J=4.8), 3.35(3H, s), 5.00(1H, s), 5.04(1H, d, J=12.0), 5.48(1H, d, J=12.0), 6.75–6.81(3H, m), 7.17(1H, t, J=7.3), 7.30–7.46(4H, m) |
| 213 | 2.82(3H, d, J=4.8), 3.36(3H, s), 4.94(1H, s), 5.05(1H, d, J=12.0), 5.47(1H, d, J=12.0), 6.80(1H, brs), 6.89(2H, d, J=1.2), 6.96(1H, t, J=1.2), 7.33–7.47(4H, m) |
| 214 | 2.82(3H, d, J=4.8), 3.36(3H, s), 4.98(1H, s), 5.13(1H, d, J=12.0), 5.53(1H, d, J=12.0), 6.81(1H, brs), 7.15–7.26(3H, m), 7.33–7.50(5H, m) |
| 215 | 2.81(3H, d, J=4.8), 3.35(3H, s), 3.76(3H, s), 5.01(1H, s), 5.03(1H, d, J=12.0), 5.42(1H, d, J=12.0), 6.81(1H, brs), 6.81–6.84(2H, m), 6.86–6.89(2H, m), 7.30–7.48(4H, m) |
| 216 | 2.18(3H, s), 2.28(3H, s), 3.40(3H, s), 3.70(3H, s), 5.11(1H, d, J=12.2), 5.13(1H, s), 5.28(1H, d, J=12.2), 6.81(2H, d, J=7.8), 7.08(1H, t, J=7.8), 7.35–7.38(2H, m), 7.51–7.54(2H, m) |
| 217 | 2.16(3H, s), 2.27(3H, s), 2.82(3H, d, J=4.9), 3.35(3H, s), 5.02(1H, s), 5.04(1H, d, J=11.6), 5.44(1H, d, J=11.6), 6.80(1H, d, J=7.9), 6.82(1H, brs), 6.84(1H, d, J=7.9), 7.05(1H, t, J=7.9), 7.30–7.40(3H, m), 7.49–7.52(1H, m) |

| Comp. No. | mp or ¹H-NMR(CDCl₃) δ ppm |
|---|---|
| 218 | 2.23(3H, s), 2.27(3H, s), 3.39(3H, s), 3.70(3H s), 5.10(1H, d, J=12.2), 5.11(1H, s), 5.27(1H, d, J=12.2), 6.81(1H, d, J=7.8), 6.95(1H, d, J=7.8), 6.98(1H, s), 7.34–7.38(2H, m), 7.50–7.54(2H, m) |
| 219 | 104–106° C. |
| 221 | 2.17(3H, s), 2.19(3H, s), 2.81(3H, d, J=4.9), 3.35(3H, s), 5.00(1H s), 5.02(1H, d, J=12.2), 5.42(1H, d, J=12.2), 6.75(1H, dd, J=7.9, 2.4), 6.80(1H, d, J=2.4), 6.83(1H, brs), 7.02(1H, d, J=7.9) 7.30–7.50(4H, m) |
| 223 | 2.29(6H, s), 2.82(3H, d, J=4.9), 3.36(3H, s), 5.00(1H, s), 5.02(1H, d, J=11.0), 5.44(1H, d, J=11.0), 6.63(3H, s), 6.82(1H, brs), 7.29–7.48(4H, m) |
| 231 | 2.82(3H, d, J=4.9), 3.35(3H, s), 4.97(1H, s), 5.04(1H, d, J=12.0), 5.47(1H, d, J=12.0), 6.84(1H, brs), 6.85(1H, dd, J=7.4, 1.8), 6.95(1H, dd, J=7.4, 1.8), 6.99(1H, t, J=1.8), 7.20(1H, t, J=7.4), 7.33–7.45(4H, m) |
| 233 | 87–88° C. |
| 245 | 2.81(3H, d, J=4.9), 3.37(3H, s), 3.85(3H, s), 5.06(1H, s), 5.20(1H, d, J=12.2), 5.37(1H, d, J=12.2), 6.85(1H, brs), 6.96–7.03(4H, m), 7.30–7.35(2H, m), 7.44–7.49(2H, m) |
| 262 | 121–123° C. |
| 263 | 2.23(3H, s), 3.40(3H, s), 3.70(3H, s), 5.08(1H, s), 5.12(1H, d, J=12.2), 5.27(1H, d, J=12.2), 6.83(1H, d, J=7.9), 7.10(1H, dd, J=7.3, 2.4), 7.33–7.39(2H, m), 7.42–7.55(2H, m) |
| 267 | 97–99° C. |
| 282 | 2.30(3H, s), 2.80(3H, d, J=4.9), 3.36(3H, s), 3.83(3H, s), 5.06(1H, s), 5.17(1H, d, J=12.2), 5.32(1H, d, J=12.2), 6.73–6.80(2H, m), 6.87(1H, brs), 6.89(1H, d, J=7.9), 7.30–7.35(2H, m), 7.42–7.48(2H, m) |
| 285 | 3.40(3H, s), 3.64(3H, s), 5.18(1H, s), 6.87–6.93(3H, m), 7.11(1H, d, J=7.3), 7.26–7.33(3H, m), 7.51(1H, dd, J=7.3, 1.8) |
| 286 | 2.81(3H, d, J=4.9), 3.33(3H, s), 4.99(1H, s), 6.85(1H, brs), 6.86(1H, d, J=8.6), 6.94–6.98(2H, m), 7.14(1H, t, J=7.3), 7.26–7.36(4H, m) |
| 288 | 2.33(3H, s), 3.41(3H, s), 3.68(3H, s), 5.26(1H, s), 6.83–6.91(3H, m), 7.11–7.15(3H, m), 7.23–7.28(1H, m), 7.48(1H, dd, J=8.0, 1.8) |
| 289 | 2.32(3H, s), 2.82(3H, d, J=4.9), 3.35(3H, s), 5.04(1H, s), 6.82(1H, brs), 6.84(1H, d, J=8.6), 6.91–6.94(2H, m), 7.08–7.15(3H, m), 7.20–7.26(1H, m), 7.34(1H, dd, J=7.3, 1.8) |
| 291 | 2.23(6H, s), 3.4(3H, s), 3.68(3H, s), 5.26(1H, s), 6.71–6.74(1H, m), 6.80–6.86(2H, m), 7.05–7.13(2H, m), 7.22–7.28(1H, m), 7.48(1H, dd, J=7.3, 1.8) |
| 292 | 2.22(6H, s), 2.83(3H, d, J=4.9), 3.36(3H, s), 5.04(1H, s), 6.73–6.86(4H, m), 7.05–7.10(2H, m), 7.20–7.25(1H, m), 7.34 (1H, dd, J=7.3, 1.8) |
| 293 | 3.40(3H, s), 3.71(3H, s), 5.19(1H, s), 5.49(1H, d, J=12.2), 5.67(1H, d, J=12.2), 6.85(1H, d, J=8.6), 7.35–7.39(2H, m), 7.49–7.53(2H, m), 7.79(1H, dd, J=7.3, 1.8), 8.46(1H, s) |
| 294 | 2.32(3H, s), 3.40(3H, s), 3.67(3H, s), 5.23(1H, s), 6.76–6.90(4H, m), 7.11–7.30(2H, m), 7.49(1H, dd, J=7.3, 1.8) |
| 295 | 2.32(3H, s), 2.82(3H, d, J=4.9), 3.35(3H, s), 5.03(1H, s), 6.80–6.91(5H, m), 7.10–7.28(3H, m), 7.34(1H, dd, J=7.3, 1.8) |
| 296 | 2.27(6H, s), 3.40(3H, s), 3.67(3H, s), 5.23(1H, s), 6.61(2H, s), 6.74(1H, s), 6.88(1H, d, J=8.6), 7.13(1H, t, J=8.0), 7.24–7.28(1H, m), 7.49(1H, dd, J=7.3, 1.8) |
| 297 | 2.27(6H, s), 2.83(3H, d, J=4.9), 3.35(3H, s), 5.02(1H, s), 6.65(2H, s), 6.73(1H, s), 6.75(1H, brs), 6.86(1H, d, J=8.0), 7.06–7.09(1H, m), 7.21–7.28(1H, m), 7.34(1H, dd, J=7.3, 1.8) |
| 328 | 2.28(3H, s), 3.40(3H, s), 3.67(3H, s), 5.18(1H, s), 6.73–6.77(1H, m), 6.86–6.89(2H, m), 7.19(1H, d, J=7.3), 7.25–7.30(2H, m), 7.51(1H, dd, J=7.3, 1.8) |
| 329 | 2.33(3H, s), 2.82(3H, d, J=4.9), 3.34(3H, s), 4.99(1H, s), 6.77–6.93(4H, m), 7.12(1H, t, J=7.3), 7.24–7.36(3H, m) |
| 358 | 2.17(3H, s), 2.34–2.36(3H in total), 2.44–2.63(3H in total), 3.78–3.81(3H in total), 4.98–5.22(3H in total), 6.71–7.81(7H in total) |
| 359 | 122–124° C. |
| 362 | 2.16(3H, s), 2.35(3H, s), 2.39(3H, s), 2.82(3H, d, J=4.9), 4.36(1H, s), 5.13(1H, d, J=11.0), 5.25(1H, d, J=11.0), 6.73(1H, d, J=7.3), 6.84(1H, s), 7.04(1H, d, J=7.3), 7.07(1H, brs), 7.29–7.49(4H, m) |
| 366 | 2.26(3H, s), 2.28(3H, s), 2.79(3H, d, J=4.9), 3.36(3H, s), 4.06(1H, d, J=12.2), 4.69(1H, d, J=12.2), 5.18(1H, s), 6.84(1H, brs), 6.91(1H, d, J=7.3), 7.04(1H, d, J=7.3), 7.14(1H, s), 7.18–7.28(3H, m), 7.36(1H, d, J=7.3) |
| 372 | 1.56(3H, s), 2.22(3H, s), 3.23(3H, d, J=4.9), 3.35(3H, s), 5.15(1H, d, J=12.2), 5.36(1H, s), 5.58(1H, d, J=12.2), 6.88(1H, d, J=7.9), 7.11(1H, d, J=7.9), 7.13(1H, s), 7.29–7.37(3H, m), 7.45–7.48(1H, m), 8.75(1H, brs) |
| 413 | 2.83(3H, d, J=4.9), 3.36(3H, s), 5.09(1H, s), 5.50(1H, d, J=13.0), 5.86(1H, d, J=13.0), 6.80(1H, s), 6.85(1H, brs), 7.32–7.38 (3H, m), 7.45–7.49(1H, m), 8.57(1H, s) |
| 417 | 115–117° C. |
| 420 | 131–133° C. |
| 421 | 2.84(3H, d, J=4.9), 4.99(1H, brs), 5.39(1H, s), 5.57(1H, d, J=12.2), 5.67(1H, d, J=12.2), 6.50(1H, brs), 7.00(1H, dd, J=6.7, 6.1), 7.31–7.37(3H, m), 7.49–7.51(1H, m), 7.90(1H, dd, J=6.1, 1.8), 8.27(1H, dd, J=6.7, 1.8) |
| 422 | 63–64° C. |
| 423 | 105–107° C. |
| 427 | 133–135° C. |
| 429 | 79–81° C. |
| 430 | 3.40(3H, s), 3.71(3H, s), 5.19(1H, s), 5.49(1H, d, J=12.2), 5.67(1H, d, J=12.2), 6.85(1H, d, J=8.6), 7.35–7.39(2H, m), 7.46–7.52(2H, m), 7.80(1H, dd, J=8.6, 1.8), 8.46(1H, s) |
| 432 | 3.42(3H, s), 3.70(3H, s), 5.25(1H, s), 5.49(1H, d, J=12.2), 5.66(1H, d, J=12.2), 7.34–7.38(2H, m), 7.52–7.56(2H, m), 7.65(1H, d, J=2.4), 8.01(1H, d, J=2.4) |
| 433 | 114–115° C. |
| 434 | 58–60° C. |
| 436 | 102–104° C. |
| 437 | 2.82(3H, d, J=5.5), 3.39(3H, s), 5.03(1H, s), 5.22(1H, d, J=12.0), 5.64(1H, d, J=12.0), 6.82(1H, brs), 7.19(1H, dd, J=8.0, 4.8), 7.33–7.49(5H, m), 8.01(1H, dd, J=4.8, 1.8) |
| 439 | 2.09(3H, s), 2.34(3H, s), 3.85(3H, s), 5.05(1H, d, J=11.0), 5.10(1H, d, J=11.0), 6.68(1H, s), 6.74(1H, d, J=7.3), 6.75(1H, s), 7.03(1H, d, J=7.3), 7.48–7.53(2H, m), 7.61–7.66(1H, m) |
| 443 | 89–90° C. |
| 448 | 80–82° C. |
| 453 | 83–85° C. |
| 454 | 3.39(3H, s), 3.70(3H, s), 5.19(1H, s), 5.38(1H, d, J=12.2), 5.58(1H, d, J=12.2), 6.73(1H, d, J=9.1), 7.30–7.37(2H, m), 7.47–7.55(3H, m), 8.11(1H, d, J=2.4) |
| 459 | 103–105° C. |
| 461 | 0.87(3H, t, J=7.3), 1.26–1.40(2H, m), 1.51–1.62(2H, m), 2.20(3H, |

-continued

| Comp. No. | mp or $^1$H-NMR(CDCl$_3$) δ ppm |
|---|---|
| | s), 2.31(3H, s), 3.22(3H, d, J=4.9), 3.44(2H, t, J=7.3), 5.14(1H, d, J=11.6), 5.46(1H, s), 5.59(1H, d, J=11.6), 6.69(1H, d, J=7.3), 6.80(1H, s), 7.02(1H, d, J=7.3), 7.31–7.34(3H, m), 7.47–7.51(1H, m), 8.82(1H, brs). |
| 462 | 205–210° C. |
| 463 | 105–110° C. |
| 465 | 2.11(3H, s), 2.23(3H, s), 2.29(3H, s), 2.81(3H, d, J=4.9), 3.35(3H, s), 5.03(1H, s), 5.03(1H, d, J=11.6), 5.44(1H, d, J=11.6), 6.64(1H, s), 6.68(1H, s), 7.32–7.43(3H, m), 7.50–7.53(1H, m) |
| 466 | 81–82° C. |
| 467 | 91–92° C. |
| 468 | 2.83(1H, d, J=4.9), 3.38(3H, s), 4.47(1H, d, J=12.2), 4.88(1H, d, J=12.2), 5.14(1H, s), 6.82(1H, brs), 7.20–7.30(2H, m), 7.32–7.38(1H, m), 7.42–7.49(1H, m), 7.56(1H, d, J=1.8), 8.35(1H, d, J=1.8) |
| 469 | 0.91 & 1.13(3H in total, each s), 2.21(3H, s), 2.85 & 2.95(3H in total, each s), 3.26 & 3.48(2H in total, each m), 3.43(3H, s), 5.05(1H, d, J=12.2), 5.22(1H, s), 5.25(1H, d, J=12.2), 6.86(1H, d, J=9.1), 7.12(1H, d, J=7.3), 7.13(1H, s), 7.33–7.41(3H, m), 7.49–7.55(1H, m) |
| 470 | 2.18(3H, s), 2.32(3H, s), 3.41(3H, s), 5.05(1H, d, J=11.6), 5.17(1H, s), 5.31(1H, d, J=11.6), 6.71(1H, d, J=7.3), 6.76(1H, s), 7.02(1H, d, J=7.9), 7.35–7.41(2H, m), 7.48–7.54(2H, m) |
| 471 | 2.27(3H, s), 3.22(3H, s), 3.49(3H, s), 3.54(3H, s), 5.09(1H, d, J=12.2), 5.26(1H, d, J=12.2), 5.72(1H, s), 6.86–6.94(2H, m), 7.15–7.20(2H, m), 7.25–7.39(3H, m), 7.56(1H, d, J=7.3) |
| 472 | 110–112° C. |
| 473 | 2.28(6H, s), 2.80(3H, d, J=4.9), 3.33(3H, s), 4.87(1H, d, J=12.2), 5.06(1H, s), 5.27(1H, d, J=12.2), 6.77(1H, brs), 6.98(1H, dd, J=8.5, 6.1), 7.02(2H, d, J=7.3), 7.30–7.43(3H, m), 7.60–7.63(1H, m) |

Example 19

Synthesis of (E)-2-benzylideneaminooxymethyl-α-methoxy-N-methylphenylacetamide (Compound 480)

A solution of 2-hydroxymethyl-α-methoxy-N-methylphenylacetamide (0.42 g, 2.0 mmol) in tetrahydrofuran (4 ml) was stirred at 0° C., and thionyl chloride (0.17 ml, 2.4 mmol) and one drop of N,N-dimethylformamide were added. The mixture was stirred at room temperature for 2 hours, and water was added. The resulting mixture was extracted with ether, washed with saturated brine and dried over anhydrous magnesium sulfate. Evaporation of the solvent gave a crude product (0.38 g) as an oil. Benzaldehyde oxime (0.37 g, 3.1 mmol) and potassium carbonate (0.55 g, 4.0 mmol) were added to a solution of the crude product in N,N-dimethylformamide (6 ml), and the mixture was stirred at room temperature for 3 days. Water was added, and the mixture was extracted with ether and dried over anhydrous magnesium sulfate. The solvent was evaporated, and the residue was purified by column chromatography on silica gel (n-hexane/ethyl acetate=13/7) to give the desired compound (E)-2-benzylideneaminooxymethyl-(-methoxy-N-methylphenylacetamide (0.32 g, 51%) as white crystals.

mp.: 75.0–75.5° C.

NMR (δ ppm, TMS/CDCl$_3$): 2.84(3H,d,J=4.9), 3.34 (3H, s), 5.13(1H,s), 5.23(1H,d,J=12.2), 5.65(1H,d,J=12.2), 6.80 (1H,brs), 7.27–7.40(6H,m), 7.41–7.48(1H,m), 7.53–7.58 (2H,m), 8.10(1H,s).

Example 20

Synthesis of methyl (E)-2-benzylideneaminooxymethyl-α-hydroxyphenylacetate (Compound No. 483)

Sodium borohydride (0.04 g, 1.0 mmol) was added to a solution of methyl 2-(2-bromomethyl)phenyl-2-oxoacetate (0.51 g, 2.0 mmol) in methanol (10 ml). After 8 minutes, acetic acid was added to decompose the excess reagent. Water was added, and the mixture was extracted with ethyl acetate and dried over anhydrous sodium sulfate. The solvent was evaporated, and the residue was purified by column chromatography on silica gel (n-hexane/ethyl acetate=4/1) to give the desired compound methyl 2-bromomethyl-α-hydroxyphenylacetate (0.41 g, 80%) as an oil.

Then, benzaldehyde oxime (0.28 g, 2.3 mmol) and potassium carbonate (0.43 g, 3.1 mmol) were added to a solution of methyl 2-bromomethyl-α-hydroxyphenylacetate (0.40 g, 1.5 mmol) in acetone (6 ml), and the mixture was stirred at room temperature for 18 hours. Water was added, and the mixture was extracted with ether, dried over anhydrous magnesium sulfate and concentrated under reduced pressure. The residue was purified by column chromatography on silica gel (n-hexane/ethyl acetate=3/1) to give the desired compound methyl (E)-2-benzylideneaminooxymethyl-α-hydroxyphenylacetate (0.08 g, 17%) as an oil.

NMR (δ ppm, TMS/CDCl$_3$): 3.74(1H,d,J=5.5), 3.75 (3H, s), 5.31(1H,d,J=12.2), 5.42(1H,d,J=12.2), 5.59 (1H,d,J=5.5), 7.34–7.39(6H,m), 7.41–7.50(1H,m), 7.52–7.66 (2H, m), 8.11(1H,s).

Example 21

Synthesis of methyl (E)-2-(2-benzylideneaminooxymethyl)phenyl-2-oxoacetate

Benzaldehyde oxime (2.13 g, 17.6 mmol) and potassium carbonate (2.90 g, 21.0 mmol) were added a solution of methyl 2-(2-bromomethyl)phenyl-2-oxoacetate (3.00 g, 11.7 mmol) in acetone (10 ml), and the mixture was stirred at room temperature for 7 hours. Water was added, and the mixture was extracted with ether and dried over anhydrous magnesium sulfate. The solvent was evaporated, and the residue was purified by column chromatography on silica gel (n-hexane/ethyl acetate=17/3) to give the desired compound methyl (E)-2-(benzylideneaminooxymethyl)-2-oxophenylacetate (2.39 g, 69%).

NMR (δ ppm, TMS/CDCl$_3$): 3.89(3H,s), 5.32 (1H,d,J= 12.2), 5.40(1H,d,J=12.2), 7.32–7.59(8H,m), 7.70 (1H,d,J= 6.7), 8.16(1H,s).

Example 22

Synthesis of methyl (E)-α-hydroxy-2-(α-methyl-4-chlorobenzylideneaminooxymethyl)phenylacetate (Compound No. 479)

A solution of methyl 2-bromomethyl-α-hydroxyphenylacetate (30.53 g, 0.118 mmol) and 3,4-dihydro-2H-pyran (17.84 g, 0.212 mol) in methylene chloride (230 ml) was stirred at 0° C. Pyridinium p-toluenesulfonate (2.96 g, 0.012 mol) was added, and the mixture was stirred at room temperature for 2 hours. Water was added, and the mixture was extracted with methylene chloride and dried over anhydrous magnesium sulfate. The solvent was evaporated, and the residue was purified by column chromatography on silica gel (n-hexane/ethyl acetate=17/3) to give the desired compound methyl 2-bromomethyl-α-(tetrahydropyran-2-yl)phenylacetate (33.58 g, 83.0%) as an oil.

Then, a solution of methyl 2-bromomethyl-α-(tetrahydropyran-2-yl)phenylacetate (4.00 g, 11.7 mmol) and 4-chloroacetophenone oxime (2.97 g, 17.5 mmol) in N,N-dimethylformamide (30 ml) was stirred at 0° C., and 60% oily sodium hydride (0.70 g, 17.5 mmol) was added thereto. After 2 hours, water was added, and the mixture was adjusted to pH 7 with 1N hydrochloric acid, extracted with ether and dried over anhydrous magnesium sulfate. Evaporation of the solvent gave a crude product (6.28 g).

The crude product was dissolved in methanol (35 ml), and pyridinium p-toluenesulfonate (0.29 g, 1.2 mmol) was added. After heating under reflux for 30 minutes, the reaction mixture was concentrated under reduced pressure, and water was added. The mixture was extracted with ether and dried over anhydrous magnesium sulfate, and the solvent was evaporated. The residue was purified by column chromatography on silica gel (n-hexane/ethyl acetate=3/1) to give the desired compound methyl (E)-α-hydroxy-2-(α-methyl-4-chlorobenzylideneaminooxy)phenylacetate (2.75 g, 68%) as an oil.

NMR (δ ppm, TMS/CDCl$_3$): 2.23(3H,s), 3.75(3H,s), 3.77 (1H,d,J=5.5), 5.34(1H,d,J=12.2), 5.42(1H,d,J=12.2), 7.29–7.38(5H,m), 7.43–7.48(1H,m), 7.56(2H,d,J=8.6).

Example 23

Synthesis of methyl (E)-α-methoxy-2-((-methyl-4-chlorobenzylideneaminooxy)phenylacetate
(Compound No. 477)

60% oily sodium hydride (0.20 g, 5.0 mmol) was added to a solution of methyl (E)-α-hydroxy-2-(α-methyl-4-chlorobenzylideneaminooxy)phenylacetate (1.59 g, 4.6 mmol) and methyl iodide (1.95 g, 13.7 mmol) in N,N-dimethylformamide (15 ml) with stirring at 0° C. After 45 minutes, water was added, and the mixture was adjusted to pH 1 with 1N hydrochloric acid, extracted with ether, washed with saturated brine and dried over anhydrous magnesium sulfate. The solvent was evaporated, and the residue was purified by column chromatography on silica gel (n-hexane/methylene chloride=9/1) to give the desired compound methyl (E)-α-methoxy-2-((α-methyl-4-chlorobenzylideneaminooxy)phenylacetate (1.19 g, 72%) as an oil.

NMR (δ ppm, TMS/CDCl$_3$): 2.23(3H,s), 3.39(3H,s), 3.71 (3H,s), 5.24(1H,s), 5.27(1H,d,J=12.2), 5.51(1H,d,J=12.2), 7.30–7.54(6H,m), 7.58(2H,d,J=8.5).

Example 24

Synthesis of (E)-α-methoxy-N-methyl-2-(α-methyl-4-chlorobenzylideneaminooxy)phenylacetamide
(Compound No. 474)

A solution of methyl (E)-α-methoxy-2-(α-methyl-4-chlorobenzylideneaminooxy)phenylacetate (0.48 g, 1.3 mmol) and 40% monomethylamine-methanol solution (10 ml) was stirred in a sealed tube at 80° C. for 15 hours. The mixture was cooled to room temperature, and then the solvent was evaporated under reduced pressure. Water was added, the mixture was adjusted to pH 1 with 1N hydrochloric acid, extracted with methylene chloride and dried over anhydrous magnesium sulfate. The solvent was evaporated, and the residue was purified by column chromatography on silica gel (n-hexane/ethyl acetate=3/2) to give the desired compound (E)-α-methoxy-N-methyl-2-(α-methyl-4-chlorobenzylideneaminooxy)phenylacetamide (0.41 g, 86%) as an oil.

NMR (δ ppm, TMS/CDCl$_3$): 2.22(3H,s), 2.83 (3H,d,J=4.9), 3.32(3H,s), 5.13(1H,s), 5.26(1H,d,J=12.2), 5.66(1H,d, J=12.2), 6.77(1H,brs), 7.29–7.47(6H,m), 7.57 (2H,d,J=8.5).

Example 25

Synthesis of (E)-α-methoxy-N-methyl-2-(α-methyl-4-chlorobenzylideneaminooxy)phenylthioacetamide
(Compound 603)

Lawesson's reagent (40 mg, 0.1 mmol) was added to a solution of (E)-α-methoxy-N-methyl-2-(α-methyl-4-chlorobenzylideneaminooxy)phenylacetamide (73 mg, 0.2 mmol) in toluene (3 ml), and the mixture was heated at 80° C. for 1.5 hours with stirring. The mixture was cooled to room temperature. Water was added, and the mixture was extracted with ether and dried over anhydrous magnesium sulfate. The solvent was evaporated, and the residue was purified by column chromatography on silica gel (n-hexane/ethyl acetate=4/1) to give the desired compound (E)-α-methoxy-N-methyl-2-(α-methyl-4-chlorobenzylideneaminooxy)phenylthioacetamide (50 mg, 66%) as an oil.

NMR (δ ppm, TMS/CDCl$_3$): 2.23(3H,s), 3.25 (3H,d,J=4.9), 3.33(3H,s), 5.29(1H,d,J=12.2), 5.51(1H,s), 5.80 (1H, d,J=12.2), 7.25–7.36(5H,m), 7.42–7.47(1H,m), 7.58 (2H,d, J=9.2), 8.77(1H,s).

Example 26

Synthesis of ethyl α-hydroxy-2-(tetrahydropyran-2-yloxymethyl)phenylacetate

A solution of ethyl 2-oxo-2-[2-(tetrahydropyran-2-yloxymethyl)phenyl]acetate (22.60 g, 77.3 mmol) in methanol (20 ml) was stirred at 0° C., and sodium borohydride (1.46 g, 38.6 mmol) was added to thereto. After 10 minutes, water (100 ml) was added, and the mixture was extracted with ethyl acetate and dried over anhydrous magnesium sulfate. The solvent was evaporated, and the residue was purified by column chromatography on silica gel (n-hexane/ethyl acetate=4/1) to give the desired compound ethyl α-hydroxy-2-(tetrahydropyran-2-yloxymethyl) phenylacetate (20.47 g, 90.0%) as an oil.

NMR (δ ppm, TMS/CDCl$_3$): 1.19–1.22(3H,m), 1.50–1.73 (6H,m), 3.52–3.57(1H,m), 3.80 and 3.87(1H in total, each d,J=5.5), 3.81–3.88(1H,m), 4.09–4.30(2H,m), 4.65 and 4.69 (1H in total, each d,J=12.2), 4.69(1H,m), 4.89 and 4.92(1H in total, each d,J=12.2), 5.48(1H,m), 7.30–7.41(4H,m).

Example 27

Synthesis of ethyl α-methoxy-2-(tetrahydropyran-2-yloxymethyl)phenylacetate

Methyl iodide (20.25 g, 143 mmol) was added to a solution of ethyl α-hydroxy-2-(tetrahydropyran-2-yloxymethyl)phenylacetate (14.00 g, 47.6 mmol) in N,N-dimethylformamide (40 ml), and the mixture was stirred at 0° C. 60% oily sodium hydride (1.90 g, 47.5 mmol) was added thereto. After 30 minutes, water (100 ml) was added, and the mixture was extracted with ether and dried over anhydrous magnesium sulfate. The solvent was evaporated, and the residue was purified by column chromatography on silica gel (n-hexane/ ethyl acetate=4/1) to give the desired compound ethyl α-methoxy-2-(tetrahydropyran-2-yloxymethyl)phenylacetate (14.00 g, 95.5%) as an oil.

NMR (δ ppm, TMS/CDCl$_3$): 1.20(3H,t,J=6.8), 1.50–1.90 (6H,m), 3.38 and 3.39(3H in total, each s), 3.50–3.60 (1H,m), 3.89–3.95(1H,m), 4.10–4.30(2H,m), 4.56 and 5.01 (1H in total, each d,J=12.2), 4.62(1H,m), 4.74 and 4.84(1H in total, each d, J=12.2), 5.17 and 5.23(1H in total,each s), 7.30–7.51(4H,m).

Example 28

Synthesis of 4-methoxy-3-isochromanone

Pyridinium p-toluenesulfonate (0.30 g) was added to a solution of ethyl α-methoxy-2-(tetrahydropyran-2-yloxymethyl)phenylacetate (14.00 g, 45.4 mmol) in methanol (50 ml), and the mixture was heated under reflux for 1 hour. The mixture was cooled to room temperature, and water (50 ml) was added. The mixture was extracted with methylene chloride and dried over anhydrous magnesium sulfate. The solvent was evaporated, and the residue was purified by recrystallization from n-hexane/ethyl acetate (=1/1) to give the desired compound 4-methoxy-3-isochromanone (6.00 g, 74.2%) as white crystals.

mp.: 82–86° C.

NMR (δ ppm, TMS/CDCl$_3$): 3.73(3H,s), 4.75(1H,s), 5.28 (1H,d,J=14.0), 5.38(1H,d,J=14.0), 7.24–7.27(1H,m), 7.37 (2H,m), 7.56(1H,d,J=7.3).

Example 29

Synthesis of 2-hydroxymethyl-α-methoxy-N-methylphenylacetamide

40% methylamine-methanol solution (9.80 g, 126 mmol) was added to 4-methoxy-3-isochromanone (7.50 g, 42.1 mmol) in methanol (40 ml), and the mixture was stirred at room temperature for 1 hour. Evaporation of the solvent gave the desired compound 2-hydroxymethyl-(α-methoxy-N-methylphenylacetamide (8.50 g, 96.5%) as white crystals.

mp.: 80–82° C.

NMR (δ ppm, TMS/CDCl$_3$): 2.86(3H,s), 3.35(3H,s), 4.47 (1H,d,J=11.6), 4.88(1H,d,J=11.6), 5.08(1H,s), 6.98(1H,brs), 7.32–7.41(4H,m).

Example 30

Synthesis of (E)-α-methoxy-2-((α-methyl-4-chlorobenzylideneaminooxymethyl)phenylacetic acid (Compound No. 637)

1N sodium hydroxide solution (10 ml) was added to a solution of ethyl (E)-α-methoxy-2-((α-methyl-4-chlorobenzylideneaminooxymethyl)phenylacetate (0.70 g, 1.9 mmol) in methanol (10 ml), and the mixture was stirred at room temperature for 2 hours. The mixture was adjusted to pH 4 with 1N hydrochloric acid, extracted with methylene chloride and dried over anhydrous magnesium sulfate. Evaporation of the solvent gave the desired compound (E)-α-methoxy-2-α-methyl-4-chlorobenzylideneaminooxymethyl)phenylacetic acid (0.50 g, 77%) as an oil.

NMR (δ ppm, TMS/CDCl$_3$): 2.20(3H,s), 3.39(3H,s), 5.25 (1H,s), 5.25(1H,d,J=12.2), 5.52(1H,d,J=12.2), 7.30–7.57 (8H,m).

Example 31

According to the same manner as that described in Examples 19 to 30, various compounds of the formula (I) were synthesized. The compounds thus obtained and the physical data of their representative compounds are shown below. In the tables, the compounds obtained in Examples 19 to 30 and their physical data are also listed.

In the tables, Compound Nos. 474–935 are compounds of the formula (I) wherein M is O, and Q is a group of the formula (a); Compounds Nos. 936–980 are compounds of the formula (I) wherein M is NR$^2$, and Q is a group of the formula (a); and Compound Nos. 981–1010 are compounds of the formula (I) wherein Q is a group of the formula (b).

| Comp. No. | X | R$^1$ | Y | Z | n | R$^{12}$ | R$^{13}$ |
|---|---|---|---|---|---|---|---|
| 474 | H | OCH$_3$ | NHCH$_3$ | O | 1 | CH$_3$ | 4-Cl-phenyl |
| 475 | H | OH | NHCH$_3$ | O | 1 | CH$_3$ | 4-Cl-phenyl |
| 476 | H | OCH$_3$ | NH$_2$ | O | 1 | CH$_3$ | 4-Cl-phenyl |
| 477 | H | OCH$_3$ | OCH$_3$ | O | 1 | CH$_3$ | 4-Cl-phenyl |
| 478 | H | OH | NH$_2$ | O | 1 | CH$_3$ | 4-Cl-phenyl |
| 479 | H | OH | OCH$_3$ | O | 1 | CH$_3$ | 4-Cl-phenyl |
| 480 | H | OCH$_3$ | NHCH$_3$ | O | 1 | H | Phenyl |
| 481 | H | OH | NHCH$_3$ | O | 1 | H | Phenyl |
| 482 | H | OCH$_3$ | OCH$_3$ | O | 1 | H | Phenyl |
| 483 | H | OH | OCH$_3$ | O | 1 | H | Phenyl |
| 484 | H | OCH$_3$ | NH$_2$ | O | 1 | H | Phenyl |
| 485 | H | OH | NH$_2$ | O | 1 | H | Phenyl |
| 486 | H | OCH$_3$ | NHCH$_3$ | O | 1 | CH$_3$ | Phenyl |
| 487 | H | OCH$_3$ | NH$_2$ | O | 1 | CH$_3$ | Phenyl |
| 488 | H | OCH$_3$ | OCH$_3$ | O | 1 | CH$_3$ | Phenyl |
| 489 | H | OH | NHCH$_3$ | O | 1 | CH$_3$ | Phenyl |
| 490 | H | OH | NH$_2$ | O | 1 | CH$_3$ | Phenyl |
| 491 | H | OH | OCH$_3$ | O | 1 | CH$_3$ | Phenyl |
| 492 | H | OCH$_3$ | NHCH$_3$ | O | 1 | CH$_3$ | 4-OCH$_3$-phenyl |
| 493 | H | OCH$_3$ | NH$_2$ | O | 1 | CH$_3$ | 4-OCH$_3$-phenyl |
| 494 | H | OCH$_3$ | OCH$_3$ | O | 1 | CH$_3$ | 4-OCH$_3$-phenyl |
| 495 | H | OH | NHCH$_3$ | O | 1 | CH$_3$ | 4-OCH$_3$-phenyl |

-continued

| | | | | | | | |
|---|---|---|---|---|---|---|---|
| 496 | H | OH | $NH_2$ | O | 1 | $CH_3$ | 4-$OCH_3$-phenyl |
| 497 | H | OH | $OCH_3$ | O | 1 | $CH_3$ | 4-$OCH_3$-phenyl |
| 498 | H | $OCH_3$ | $NHCH_3$ | O | 1 | $CH_3$ | 4-$CH_3$-phenyl |
| 499 | H | $OCH_3$ | $NH_2$ | O | 1 | $CH_3$ | 4-$CH_3$-phenyl |
| 500 | H | $OCH_3$ | $OCH_3$ | O | 1 | $CH_3$ | 4-$CH_3$-phenyl |
| 501 | H | OH | $NHCH_3$ | O | 1 | $CH_3$ | 4-$CH_3$-phenyl |
| 502 | H | OH | $NH_2$ | O | 1 | $CH_3$ | 4-$CH_3$-phenyl |
| 503 | H | OH | $OCH_3$ | O | 1 | $CH_3$ | 4-$CH_3$-phenyl |
| 504 | H | $OCH_3$ | $NHCH_3$ | O | 1 | $CH_3$ | 2,4-$Cl_2$-phenyl |
| 505 | H | $OCH_3$ | $NH_2$ | O | 1 | $CH_3$ | 2,4-$Cl_2$-phenyl |
| 506 | H | $OCH_3$ | $OCH_3$ | O | 1 | $CH_3$ | 2,4-$Cl_2$-phenyl |
| 507 | H | OH | $NHCH_3$ | O | 1 | $CH_3$ | 2,4-$Cl_2$-phenyl |
| 508 | H | OH | $NH_2$ | O | 1 | $CH_3$ | 2,4-$Cl_2$-phenyl |
| 509 | H | OH | $OCH_3$ | O | 1 | $CH_3$ | 2,4-$Cl_2$-phenyl |
| 510 | H | OH | $NHCH_3$ | O | 1 | $CH_3$ | 2-Cl-phenyl |
| 511 | H | OH | $NH_2$ | O | 1 | $CH_3$ | 2-Cl-phenyl |
| 512 | H | OH | $OCH_3$ | O | 1 | $CH_3$ | 2-Cl-phenyl |
| 513 | H | $OCH_3$ | $NHCH_3$ | O | 1 | $CH_3$ | 2-Cl-phenyl |
| 514 | H | $OCH_3$ | $NH_2$ | O | 1 | $CH_3$ | 2-Cl-phenyl |
| 515 | H | $OCH_3$ | $OCH_3$ | O | 1 | $CH_3$ | 2-Cl-phenyl |
| 516 | H | OH | $NHCH_3$ | O | 1 | $CH_3$ | 3-Cl-phenyl |
| 517 | H | $OCH_3$ | $NHCH_3$ | O | 1 | $CH_3$ | 3-Cl-phenyl |
| 518 | H | $OCH_3$ | $OCH_3$ | O | 1 | $CH_3$ | 3-Cl-phenyl |
| 519 | H | OH | $NHCH_3$ | O | 1 | $CH_3$ | 2-$CF_3$-phenyl |
| 520 | H | $OCH_3$ | $NHCH_3$ | O | 1 | $CH_3$ | 2-$CF_3$-phenyl |
| 521 | H | $OCH_3$ | $OCH_3$ | O | 1 | $CH_3$ | 2-$CF_3$-phenyl |
| 522 | H | OH | $NHCH_3$ | O | 1 | $CH_3$ | 3-$CF_3$-phenyl |
| 523 | H | $OCH_3$ | $NHCH_3$ | O | 1 | $CH_3$ | 3-$CF_3$-phenyl |
| 524 | H | $OCH_3$ | $OCH_3$ | O | 1 | $CH_3$ | 3-$CF_3$-phenyl |
| 525 | H | OH | $NHCH_3$ | O | 1 | $CH_3$ | 4-$CF_3$-phenyl |
| 526 | H | $OCH_3$ | $NHCH_3$ | O | 1 | $CH_3$ | 4-$CF_3$-phenyl |
| 527 | H | $OCH_3$ | $OCH_3$ | O | 1 | $CH_3$ | 4-$CF_3$-phenyl |
| 528 | H | OH | $NHCH_3$ | O | 1 | $CH_3$ | 4-$NO_2$-phenyl |
| 529 | H | $OCH_3$ | $NHCH_3$ | O | 1 | $CH_3$ | 4-$NO_2$-phenyl |
| 530 | H | $OCH_3$ | $OCH_3$ | O | 1 | $CH_3$ | 4-$NO_2$-phenyl |
| 531 | H | OH | $NHCH_3$ | O | 1 | $CH_3$ | 2-$CH_3$-phenyl |
| 532 | H | $OCH_3$ | $NHCH_3$ | O | 1 | $CH_3$ | 2-$CH_3$-phenyl |
| 533 | H | $OCH_3$ | $OCH_3$ | O | 1 | $CH_3$ | 2-$CH_3$-phenyl |
| 534 | H | OH | $NHCH_3$ | O | 1 | $CH_3$ | 3-$CH_3$-phenyl |
| 535 | H | $OCH_3$ | $NHCH_3$ | O | 1 | $CH_3$ | 3-$CH_3$-phenyl |
| 536 | H | $OCH_3$ | $OCH_3$ | O | 1 | $CH_3$ | 3-$CH_3$-phenyl |
| 537 | H | OH | $NHCH_3$ | O | 1 | $CH_3$ | 4-CN-phenyl |
| 538 | H | $OCH_3$ | $NHCH_3$ | O | 1 | $CH_3$ | 4-CN-phenyl |
| 539 | H | $OCH_3$ | $OCH_3$ | O | 1 | $CH_3$ | 4-CN-phenyl |
| 540 | H | OH | $NHCH_3$ | O | 1 | $C_2H_5$ | 4-Cl-phenyl |
| 541 | H | $OCH_3$ | $NHCH_3$ | O | 1 | $C_2H_5$ | 4-Cl-phenyl |
| 542 | H | $OCH_3$ | $OCH_3$ | O | 1 | $C_2H_5$ | 4-Cl-phenyl |
| 543 | H | OH | $NHCH_3$ | O | 1 | $C_2H_5$ | 4-$OCH_3$-phenyl |
| 544 | H | $OCH_3$ | $NHCH_3$ | O | 1 | $C_2H_5$ | 4-$OCH_3$-phenyl |
| 545 | H | $OCH_3$ | $OCH_3$ | O | 1 | $C_2H_5$ | 4-$OCH_3$-phenyl |
| 546 | H | OH | $NHCH_3$ | O | 1 | $CH_3$ | $CH_3$ |
| 547 | H | $OCH_3$ | $NHCH_3$ | O | 1 | $CH_3$ | $CH_3$ |
| 548 | H | $OCH_3$ | $OCH_3$ | O | 1 | $CH_3$ | $CH_3$ |
| 549 | H | OH | $NHCH_3$ | O | 1 | | $CH_3$, $C_4H_9$ EZ mixture |
| 550 | H | $OCH_3$ | $NHCH_3$ | O | 1 | | $CH_3$, $C_4H_9$ EZ mixture |
| 551 | H | $OCH_3$ | $OCH_3$ | O | 1 | | $CH_3$, $C_4H_9$ EZ mixture |
| 552 | H | OH | $NHCH_3$ | O | 1 | $CH_3$ | 2-$OCH_3$-phenyl |
| 553 | H | $OCH_3$ | $NHCH_3$ | O | 1 | $CH_3$ | 2-$OCH_3$-phenyl |
| 554 | H | $OCH_3$ | $OCH_3$ | O | 1 | $CH_3$ | 2-$OCH_3$-phenyl |
| 555 | H | OH | $NHCH_3$ | O | 1 | $CH_3$ | 3-$OCH_3$-phenyl |
| 556 | H | $OCH_3$ | $NHCH_3$ | O | 1 | $CH_3$ | 3-$OCH_3$-phenyl |
| 557 | H | $OCH_3$ | $OCH_3$ | O | 1 | $CH_3$ | 3-$OCH_3$-phenyl |
| 558 | H | OH | $NHCH_3$ | O | 1 | $CH_3$ | 3,4-$(CH_3)_2$-phenyl |
| 559 | H | $OCH_3$ | $NHCH_3$ | O | 1 | $CH_3$ | 3,4-$(CH_3)_2$-phenyl |
| 560 | H | $OCH_3$ | $OCH_3$ | O | 1 | $CH_3$ | 3,4-$(CH_3)_2$-phenyl |
| 561 | H | OH | $NHCH_3$ | O | 1 | $CH_3$ | 3,4-$Cl_2$-phenyl |
| 562 | H | $OCH_3$ | $NHCH_3$ | O | 1 | $CH_3$ | 3,4-$Cl_2$-phenyl |
| 563 | H | $OCH_3$ | $OCH_3$ | O | 1 | $CH_3$ | 3,4-$Cl_2$-phenyl |
| 564 | H | OH | $NHCH_3$ | O | 1 | $CH_3$ | 3-$CH_3$-4-$OCH_3$-phenyl |
| 565 | H | $OCH_3$ | $NHCH_3$ | O | 1 | $CH_3$ | 3-$CH_3$-4-$OCH_3$-phenyl |
| 566 | H | $OCH_3$ | $OCH_3$ | O | 1 | $CH_3$ | 3-$CH_3$-4-$OCH_3$-phenyl |
| 567 | H | OH | $NHCH_3$ | O | 1 | $CH_3$ | 3-Cl-4-$CH_3$-phenyl |
| 568 | H | $OCH_3$ | $NHCH_3$ | O | 1 | $CH_3$ | 3-Cl-4-$CH_3$-phenyl |
| 569 | H | $OCH_3$ | $OCH_3$ | O | 1 | $CH_3$ | 3-Cl-4-$CH_3$-phenyl |
| 570 | H | OH | $NHCH_3$ | O | 1 | $CH_3$ | $COCH_3$ |
| 571 | H | $OCH_3$ | $NHCH_3$ | O | 1 | $CH_3$ | $COCH_3$ |
| 572 | H | $OCH_3$ | $OCH_3$ | O | 1 | $CH_3$ | $COCH_3$ |
| 573 | H | OH | $NHCH_3$ | O | 1 | $CH_3$ | CO-phenyl |
| 574 | H | $OCH_3$ | $NHCH_3$ | O | 1 | $CH_3$ | CO-phenyl |

-continued

| | | | | | | | |
|---|---|---|---|---|---|---|---|
| 575 | H | OCH₃ | OCH₃ | O | 1 | CH₃ | CO-phenyl |
| 576 | H | OH | NHCH₃ | O | 1 | CH₃ | 4-Biphenylyl |
| 577 | H | OCH₃ | NHCH₃ | O | 1 | CH₃ | 4-Biphenylyl |
| 578 | H | OCH₃ | OCH₃ | O | 1 | CH₃ | 4-Biphenylyl |
| 579 | H | OH | NHCH₃ | O | 1 | CH₃ | 1-Naphthyl |
| 580 | H | OCH₃ | NHCH₃ | O | 1 | CH₃ | 1-Naphthyl |
| 581 | H | OCH₃ | CCH₃ | O | 1 | CH₃ | 1-Naphthyl |
| 582 | H | OH | NHCH₃ | O | 1 | CH₃ | 2-Furyl |
| 583 | H | OCH₃ | NHCH₃ | O | 1 | CH₃ | 2-Furyl |
| 584 | H | OCH₃ | OCH₃ | O | 1 | CH₃ | 2-Furyl |
| 585 | H | OH | NHCH₃ | O | 1 | CH₃ | 2-Thienyl |
| 586 | H | OCH₃ | NHCH₃ | O | 1 | CH₃ | 2-Thienyl |
| 587 | H | OCH₃ | OCH₃ | O | 1 | CH₃ | 2-Thienyl |
| 588 | H | OH | NHCH₃ | O | 1 | CH₃ | 2-Pyridyl |
| 589 | H | OCH₃ | NHCH₃ | O | 1 | CH₃ | 2-Pyridyl |
| 590 | H | OCH₃ | OCH₃ | O | 1 | CH₃ | 2-Pyridyl |
| 591 | H | OH | NHCH₃ | O | 1 | CH₃ | 2-Pyrazinyl |
| 592 | H | OCH₃ | NHCH₃ | O | 1 | CH₃ | 2-Pyrazinyl |
| 593 | H | OCH₃ | OCH₃ | O | 1 | CH₃ | 2-Pyrazinyl |
| 594 | H | OH | NHCH₃ | O | 1 | CH₃ | 2-Pyrimidinyl |
| 595 | H | OCH₃ | NHCH₃ | O | 1 | CH₃ | 2-Pyrimidinyl |
| 596 | H | OCH₃ | OCH₃ | O | 1 | CH₃ | 2-Pyrimidinyl |
| 597 | H | OH | NHCH₃ | O | 1 | CH₃ | 5-CF₃-pyridin-2-yl |
| 598 | H | OCH₃ | NHCH₃ | O | 1 | CH₃ | 5-CF₃-pyridin-2-yl |
| 599 | H | OCH₃ | OCH₃ | O | 1 | CH₃ | 5-CF₃-pyridin-2-yl |
| 600 | H | OH | NHCH₃ | O | 1 | CH₃ | 4-OC₂H₅-pyrimidin-2-yl |
| 601 | H | OCH₃ | NHCH₃ | O | 1 | CH₃ | 4-OC₂H₅-pyrimidin-2-yl |
| 602 | H | OCH₃ | OCH₃ | O | 1 | CH₃ | 4-OC₂H₅-pyrimidin-2-yl |
| 603 | H | OCH₃ | NHCH₃ | S | 1 | CH₃ | 4-Cl-phenyl |
| 604 | H | OCH₃ | NHCH₃ | O | 1 | CF₃ | 4-Cl-phenyl |
| 605 | H | OCHF₂ | NHCH₃ | O | 1 | CF₃ | 4-Cl-phenyl |
| 606 | H | OCH₃ | NHCH₃ | S | 1 | CH₃ | 4-OCH₃-phenyl |
| 607 | H | OCH₃ | SCH₃ | O | 1 | CH₃ | 4-OCH₃-phenyl |
| 608 | H | OCH₃ | SCH₃ | O | 1 | CH₃ | 4-Cl-phenyl |
| 609 | H | OCH₃ | NHCH₃ | S | 1 | CH₃ | 4-CH₃-phenyl |
| 610 | H | OCH₃ | NHCH₃ | S | 1 | CH₃ | 4-CF₃-phenyl |
| 611 | H | OCH₃ | SCH₃ | O | 1 | CH₃ | 4-CH₃-phenyl |
| 612 | H | OH | NHCH₃ | O | 1 | CH₂OCH₃ | 4-Cl-phenyl |
| 613 | H | OCH₃ | NHCH₃ | O | 1 | CH₂OCH₃ | 4-Cl-phenyl |
| 614 | H | OCH₃ | OCH₃ | O | 1 | CH₂OCH₃ | 4-Cl-phenyl |
| 615 | H | OH | NHCH₃ | O | 1 | C₂H₅ | 4-CH₃-phenyl |
| 616 | H | OCH₃ | NHCH₃ | O | 1 | C₂H₅ | 4-CH₃-phenyl |
| 617 | H | OCH₃ | OCH₃ | O | 1 | C₂H₅ | 4-CH₃-phenyl |
| 618 | H | OH | NHCH₃ | O | 1 | C₄H₉ | 4-CH₃-phenyl |
| 619 | H | OCH₃ | NHCH₃ | O | 1 | C₄H₉ | 4-CH₃-phenyl |
| 620 | H | OCH₃ | OCH₃ | O | 1 | C₄H₉ | 4-CH₃-phenyl |
| 621 | H | OH | NHCH₃ | O | 1 | C₄H₉ | 4-Cl-phenyl |
| 622 | H | OCH₃ | NHCH₃ | O | 1 | C₄H₉ | 4-Cl-phenyl |
| 623 | H | OCH₃ | OCH₃ | O | 1 | C₄H₉ | 4-Cl-phenyI |
| 624 | H | OH | NHCH₃ | O | 1 | C₄H₉ | 4-OCH₃-phenyl |
| 625 | H | OCH₃ | NHCH₃ | O | 1 | C₄H₉ | 4-OCH₃-phenyl |
| 626 | H | OCH₃ | OCH₃ | O | 1 | C₄H₉ | 4-OCH₃-phenyl |

| Comp. No. | X | $R^1$ | Y | Z | n | $=C\begin{smallmatrix}R^{12}\\R^{13}\end{smallmatrix}$ |
|---|---|---|---|---|---|---|
| 627 | H | OCH₃ | NHCH₃ | O | 1 | =cyclohexyl |
| 628 | H | OCH₃ | OCH₃ | O | 1 | =cyclohexyl |

-continued

| | | | | | |
|---|---|---|---|---|---|
| 629 | H | OCH₃ | NHCH₃ | O | 1 |

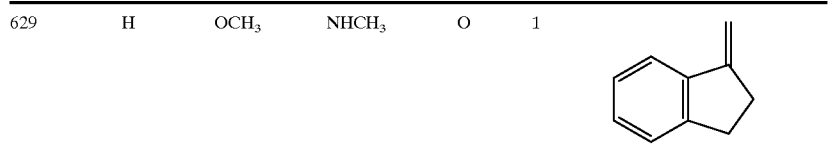

| | | | | | |
|---|---|---|---|---|---|
| 630 | H | OCH₃ | OCH₃ | O | 1 |

| Comp. No. | X | R¹ | Y | Z | n | R¹² | R¹³ |
|---|---|---|---|---|---|---|---|
| 631 | H | OCH₃ | OC₂H₅ | O | 1 | CH₃ | 4-Cl-phenyl |
| 632 | H | OCH₃ | NHC₂H₅ | O | 1 | CH₃ | 4-Cl-phenyl |
| 633 | H | OC₂H₅ | OCH₃ | O | 1 | CH₃ | 4-Cl-phenyl |
| 634 | H | OC₂H₅ | NHCH₃ | O | 1 | CH₃ | 4-Cl-phenyl |
| 635 | H | OC₄H₉ | NHCH₃ | O | 1 | CH₃ | 4-Cl-phenyl |
| 636 | H | OC₄H₉ | OCH₃ | O | 1 | CH₃ | 4-Cl-phenyl |
| 637 | H | OCH₃ | OH | O | 1 | CH₃ | 4-Cl-phenyl |
| 638 | H | OCH₃ | N(CH₃)₂ | O | 1 | CH₃ | 4-Cl-phenyl |
| 639 | H | OCOCH₃ | NHCH₃ | O | 1 | CH₃ | 4-Cl-phenyl |
| 640 | H | OTHP | NHCH₃ | O | 1 | CH₃ | 4-Cl-phenyl |
| 641 | H | OTHP | OCH₃ | O | 1 | CH₃ | 4-Cl-phenyl |
| 642 | H | OCH₃ | NHCH₃ | O | 1 | C₂H₅ | 3-Cl-phenyl |
| 643 | H | OCH₃ | NHCH₃ | O | 1 | C₂H₅ | 2-Cl-phenyl |
| 644 | H | OCH₃ | NHCH₃ | O | 1 | C₂H₅ | 2-CH₃-phenyl |
| 645 | H | OCH₃ | NHCH₃ | O | 1 | C₂H₅ | 3-CH₃-phenyl |
| 646 | H | OCH₃ | NHCH₃ | O | 1 | C₂H₅ | 2-OCH₃-phenyl |
| 647 | H | OCH₃ | NHCH₃ | O | 1 | C₂H₅ | 3-OCH₃-phenyl |
| 648 | H | OCH₃ | NHCH₃ | O | 2 | CH₃ | 4-Cl-phenyl |
| 649 | H | OCH₃ | NHCH₃ | O | 2 | CH₃ | 4-CH₃-phenyl |
| 650 | H | OCH₃ | NHCH₃ | O | 2 | CH₃ | 4-OCH₃-phenyl |
| 651 | H | OCH₃ | NHCH₃ | O | 2 | CH₃ | 4-CF₃-phenyl |
| 652 | 5-Cl | OH | NHCH₃ | O | 1 | CH₃ | 4-Cl-phenyl |
| 653 | 5-CH₃ | OCH₃ | NHCH₃ | O | 1 | CH₃ | 4-Cl-phenyl |
| 654 | 5-OCH₃ | OCH₃ | OCH₃ | O | 1 | CH₃ | 4-Cl-phenyl |
| 655 | 5-Cl | OH | NHCH₃ | O | 1 | CH₃ | 4-OCH₃-phenyl |
| 656 | 5-CH₃ | OCH₃ | NHCH₃ | O | 1 | CH₃ | 4-OCH₃-phenyl |
| 657 | 5-OCH₃ | OCH₃ | OCH₃ | O | 1 | CH₃ | 4-OCH₃-phenyl |
| 658 | 5-Cl | OH | NHCH₃ | O | 1 | CH₃ | 2-Pyridyl |
| 659 | 5-CH₃ | OCH₃ | NHCH₃ | O | 1 | CH₃ | 2-Pyridyl |
| 660 | 5-OCH₃ | OCH₃ | OCH₃ | O | 1 | CH₃ | 2-Pyridyl |
| 661 | 5-Cl | OH | NHCH₃ | O | 1 | CH₃ | 2-Pyrazinyl |
| 662 | 5-CH₃ | OCH₃ | NHCH₃ | O | 1 | CH₃ | 2-Pyrazinyl |
| 663 | 5-OCH₃ | OCH₃ | OCH₃ | O | 1 | CH₃ | 2-Pyrazinyl |
| 664 | 5-Cl | OH | NHCH₃ | O | 1 | CH₃ | 4-CH₃-phenyl |
| 665 | 5-CH₃ | OCH₃ | NHCH₃ | O | 1 | CH₃ | 4-CH₃-phenyl |
| 666 | 5-OCH₃ | OCH₃ | OCH₃ | O | 1 | CH₃ | 4-CH₃-phenyl |
| 667 | 5-Cl | OH | NHCH₃ | O | 1 | CH₃ | CH₃ |
| 668 | 5-CH₃ | OCH₃ | NHCH₃ | O | 1 | CH₃ | CH₃ |
| 669 | 5-OCH₃ | OCH₃ | OCH₃ | O | 1 | CH₃ | CH₃ |
| 670 | H | OH | NHCH₃ | O | 1 | | CH₃, C₂H₅ EZ mixture |
| 671 | H | OCH₃ | NHCH₃ | O | 1 | | CH₃, C₂H₅ EZ mixture |
| 672 | H | OCH₃ | OCH₃ | O | 1 | | CH₃, C₂H₅ EZ mixture |
| 673 | H | OCH₃ | OCH₃ | O | 1 | CH₃ | 2-Cl-4-OCH₃-phenyl |
| 674 | H | OCH₃ | NHCH₃ | O | 1 | CH₃ | 2-Cl-4-OCH₃-phenyl |
| 675 | H | OCH₃ | OCH₃ | O | 1 | CH₃ | 2-Cl-4-CH₃-phenyl |
| 676 | H | OCH₃ | NHCH₃ | O | 1 | CH₃ | 2-Cl-4-CH₃-phenyl |
| 677 | H | OCH₃ | OCH₃ | O | 1 | CH₃ | 3-Cl-4-OCH₃-phenyl |
| 678 | H | OCH₃ | NHCH₃ | O | 1 | CH₃ | 3-Cl-4-OCH₃-phenyl |
| 679 | H | OCH₃ | OCH₃ | O | 1 | CH₃ | 3-CH₃-4-Cl-phenyl |
| 680 | H | OCH₃ | NHCH₃ | O | 1 | CH₃ | 3-CH₃-4-Cl-phenyl |
| 681 | H | OCH₃ | NHCH₃ | O | 1 | CH₃ | 4-CH₂OCH₃-phenyl |
| 682 | H | OCH₃ | NHCH₃ | O | 1 | CH₃ | 4-OCHF₂-phenyl |
| 683 | H | OCH₃ | NHCH₃ | O | 1 | CH₃ | 2,4-(OCH₃)₂-phenyl |
| 684 | H | OCH₃ | NHCH₃ | O | 1 | CH₃ | 3,4-(OCH₃)₂-phenyl |
| 685 | H | OCH₃ | NHCH₃ | O | 1 | CH₃ | 2,5-(OCH₃)₂-phenyl |
| 686 | H | OCH₃ | NHCH₃ | O | 1 | CH₃ | 2,4-(CH₃)₂-phenyl |
| 687 | H | OCH₃ | OCH₃ | O | 1 | CH₃ | 2,4-(CH₃)₂-phenyl |
| 688 | H | OCH₃ | NHCH₃ | O | 1 | CH₃ | 4-Phenoxyphenyl |
| 689 | H | OCH₃ | OCH₃ | O | 1 | CH₃ | 2-F-4-OCH₃-phenyl |
| 690 | H | OCH₃ | NHCH₃ | O | 1 | CH₃ | 2-F-4-OCH₃-phenyl |

|     |   |                   |                    |   |   |                      |                                            |
| --- | - | ----------------- | ------------------ | - | - | -------------------- | ------------------------------------------ |
| 691 | H | OCH$_3$           | OCH$_3$            | O | 1 | CH$_3$               | 3-F-4-OCH$_3$-phenyl                       |
| 692 | H | OCH$_3$           | NHCH$_3$           | O | 1 | CH$_3$               | 3-F-4-OCH$_3$-phenyl                       |
| 693 | H | OCH$_3$           | NHCH$_3$           | O | 1 | H                    | 4-OCH$_3$-phenyl                           |
| 694 | H | OCH$_3$           | NHCH$_3$           | O | 1 | H                    | 4-CH$_3$-phenyl                            |
| 695 | H | OCH$_3$           | NHCH$_3$           | O | 1 | H                    | 4-CF$_3$-phenyl                            |
| 696 | H | OCH$_3$           | NHCH$_3$           | O | 1 | CH$_3$               | 2-Br-phenyl                                |
| 697 | H | OCH$_3$           | NHCH$_3$           | O | 1 | CH$_3$               | 3-Br-phenyl                                |
| 698 | H | OCH$_3$           | NHCH$_3$           | O | 1 | CH$_3$               | 4-Br-phenyl                                |
| 699 | H | OCH$_3$           | NHCH$_3$           | O | 1 | CH$_3$               | 2-F-phenyl                                 |
| 700 | H | OCH$_3$           | NHCH$_3$           | O | 1 | CH$_3$               | 3-F-phenyl                                 |
| 701 | H | OCH$_3$           | OCH$_3$            | O | 1 | CH$_3$               | 4-F-phenyl                                 |
| 702 | H | OCH$_3$           | NHCH$_3$           | O | 1 | CH$_3$               | 4-OC$_2$H$_5$-phenyl                       |
| 703 | H | OCH$_3$           | NHCH$_3$           | O | 1 | CH$_3$               | 4-OC$_3$H$_7$-phenyl                       |
| 704 | H | OCH$_3$           | NHCH$_3$           | O | 1 | CH$_3$               | 4-OC$_4$H$_9$-phenyl                       |
| 705 | H | OCH$_3$           | NHCH$_3$           | O | 1 | CH$_3$               | 4-OCH$_2$CH=CH$_2$-phenyl                  |
| 706 | H | OCH$_3$           | NHCH$_3$           | O | 1 | CH$_3$               | 4-OCH$_2$C≡CH-phenyl                       |
| 707 | H | OCH$_3$           | OCH$_3$            | O | 1 | CH$_3$               | 4-C$_2$H$_5$-phenyl                        |
| 708 | H | OCH$_3$           | NHCH$_3$           | O | 1 | CH$_3$               | 4-C$_3$H$_7$-phenyl                        |
| 709 | H | OCH$_3$           | OCH$_3$            | O | 1 | CH$_3$               | 4-C$_4$H$_9$-phenyl                        |
| 710 | H | OCH$_3$           | NHCH$_3$           | O | 1 | CH$_3$               | 4-C(CH$_3$)$_3$-phenyl                     |
| 711 | H | OCH$_3$           | OCH$_3$            | O | 1 | CH$_3$               | 2,3,5-(CH$_3$)$_3$-phenyl                  |
| 712 | H | OCH$_3$           | NHCH$_3$           | O | 1 | CH$_3$               | 3,4,5-(CH$_3$)$_3$-phenyl                  |
| 713 | H | OCH$_3$           | NHC$_2$H$_5$       | O | 1 | CH$_3$               | 4-F-phenyl                                 |
| 714 | H | OC$_2$H$_5$       | NHCH$_3$           | O | 1 | CH$_3$               | 4-F-phenyl                                 |
| 715 | H | OCH$_3$           | NHC$_2$H$_5$       | O | 1 | CH$_3$               | 4-Br-phenyl                                |
| 716 | H | OC$_2$H$_5$       | NHCH$_3$           | O | 1 | CH$_3$               | 4-Br-phenyl                                |
| 717 | H | OCH$_3$           | NHC$_2$H$_5$       | O | 1 | CH$_3$               | 4-CH$_3$-phenyl                            |
| 718 | H | OC$_2$H$_5$       | NHCH$_3$           | O | 1 | CH$_3$               | 4-CH$_3$-phenyl                            |
| 719 | H | OCH$_3$           | NHC$_2$H$_5$       | O | 1 | C$_2$H$_5$           | 4-CH$_3$-phenyl                            |
| 720 | H | OC$_2$H$_5$       | NHCH$_3$           | O | 1 | C$_2$H$_5$           | 4-CH$_3$-phenyl                            |
| 721 | H | OCH$_3$           | NHC$_2$H$_5$       | O | 1 | CH$_3$               | 4-OCH$_3$-phenyl                           |
| 722 | H | OC$_2$H$_5$       | NHCH$_3$           | O | 1 | CH$_3$               | 4-OCH$_3$-phenyl                           |
| 723 | H | OCH$_3$           | NHC$_2$H$_5$       | O | 1 | C$_2$H$_5$           | 4-OCH$_3$-phenyl                           |
| 724 | H | OC$_2$H$_5$       | NHCH$_3$           | O | 1 | C$_2$H$_5$           | 4-OCH$_3$-phenyl                           |
| 725 | H | OCH$_3$           | NHC$_2$H$_5$       | O | 1 | CH$_3$               | 4-CF$_3$-phenyl                            |
| 726 | H | OC$_2$H$_5$       | NHCH$_3$           | O | 1 | CH$_3$               | 4-CF$_3$-phenyl                            |
| 727 | H | OCH$_3$           | NHC$_2$H$_5$       | O | 1 | C$_2$H$_5$           | 4-CF$_3$-phenyl                            |
| 728 | H | OC$_2$H$_5$       | NHCH$_3$           | O | 1 | C$_2$H$_5$           | 4-CF$_3$-phenyl                            |
| 729 | H | OCH$_3$           | NHC$_2$H$_5$       | O | 1 | CH$_3$               | 4-OC$_2$H$_5$-phenyl                       |
| 730 | H | CC$_2$H$_5$       | NHCH$_3$           | O | 1 | CH$_3$               | 4-OC$_2$H$_5$-phenyl                       |
| 731 | H | OCH$_3$           | NHC$_2$H$_5$       | O | 1 | C$_2$H$_5$           | 4-OC$_2$H$_5$-phenyl                       |
| 732 | H | OC$_2$H$_5$       | NHCH$_3$           | O | 1 | C$_2$H$_5$           | 4-OC$_2$H$_5$-phenyl                       |
| 733 | H | OCH$_3$           | OCH$_3$            | O | 1 | C$_3$H$_7$           | 4-Cl-phenyl                                |
| 734 | H | OCH$_3$           | OCH$_3$            | O | 1 | 2-Thienyl            | CH$_3$                                     |
| 735 | H | OCH$_3$           | NHCH$_3$           | O | 1 | 2-Thienyl            | CH$_3$                                     |
| 736 | H | OCH$_3$           | NHCH$_3$           | O | 1 | C$_3$H$_7$           | 4-Cl-phenyl                                |
| 737 | H | OCH$_3$           | OCH$_3$            | O | 1 | CH$_2$OCH$_3$        | Phenyl                                     |
| 738 | H | OCH$_3$           | NHCH$_3$           | O | 1 | CH$_2$OCH$_3$        | Phenyl                                     |
| 739 | H | OCH$_3$           | NHC$_2$H$_5$       | O | 1 | C$_2$H$_5$           | 4-Cl-phenyl                                |
| 740 | H | OC$_2$H$_5$       | NHCH$_3$           | O | 1 | CH$_3$               | 2,4-(CH$_3$)$_2$-phenyl                    |
| 741 | H | OC$_2$H$_5$       | NHCH$_3$           | O | 1 | CH$_3$               | 3,4-(CH$_3$)$_2$-phenyl                    |
| 742 | H | OC$_2$H$_5$       | NHCH$_3$           | O | 1 | CH$_3$               | 2-CH$_3$-4-OCH$_3$-phenyl                  |
| 743 | H | CC$_2$H$_5$       | NHCH$_3$           | O | 1 | CH$_3$               | 2-OCH$_3$-4-CH$_3$-phenyl                  |
| 744 | H | OC$_2$H$_5$       | NHCH$_3$           | O | 1 | CH$_3$               | 2-Cl-4-OCH$_3$-phenyl                      |
| 745 | H | OCH$_3$           | NHCH$_3$           | O | 1 | C$_2$H$_5$           | 2,4-(CH$_3$)$_2$-phenyl                    |
| 746 | H | OCH$_3$           | NHCH$_3$           | O | 1 | C$_2$H$_5$           | 3,4-(CH$_3$)$_2$-phenyl                    |
| 747 | H | OCH$_3$           | NHCH$_3$           | O | 1 | C$_2$H$_5$           | 2-CH$_3$-4-OCH$_3$-phenyl                  |
| 748 | H | OCH$_3$           | NHCH$_3$           | O | 1 | C$_2$H$_5$           | 2-OCH$_3$-4-CH$_3$-phenyl                  |
| 749 | H | OCH$_3$           | NHCH$_3$           | O | 1 | C$_3$H$_7$           | 2,4-(CH$_3$)$_2$-phenyl                    |
| 750 | H | OCH$_3$           | NHCH$_3$           | O | 1 | C$_3$H$_7$           | 3,4-(CH$_3$)$_2$-phenyl                    |
| 751 | H | OCH$_3$           | NHCH$_3$           | O | 1 | C$_3$H$_7$           | 2-CH$_3$-4-OCH$_3$-phenyl                  |
| 752 | H | OCH$_3$           | NHCH$_3$           | O | 1 | C$_3$H$_7$           | 2-OCH$_3$-4-CH$_3$-phenyl                  |
| 753 | H | OC$_2$H$_5$       | NHCH$_3$           | O | 1 | CH$_3$               | 4-CH$_3$-phenyl                            |
| 754 | H | OC$_2$H$_5$       | NHCH$_3$           | O | 1 | CH$_3$               | 4-OCH$_3$-phenyl                           |
| 755 | H | OC$_2$H$_5$       | NHCH$_3$           | O | 1 | CH$_3$               | 4-CF$_3$-phenyl                            |
| 756 | H | OC$_3$H$_7$       | NHCH$_3$           | O | 1 | CH$_3$               | 4-Cl-phenyl                                |
| 757 | H | OC$_3$H$_7$       | NHCH$_3$           | O | 1 | CH$_3$               | 4-CH$_3$-phenyl                            |
| 758 | H | OC$_3$H$_7$       | NHCH$_3$           | O | 1 | CH$_3$               | 4-OCH$_3$-phenyl                           |
| 759 | H | OC$_3$H$_7$       | NHCH$_3$           | O | 1 | CH$_3$               | 4-CF$_3$-phenyl                            |
| 760 | H | OCH$_3$           | NHCH$_3$           | O | 1 | C$_2$H$_5$           | 4-CF$_3$-phenyl                            |
| 761 | H | OCH$_3$           | NHCH$_3$           | O | 1 | C$_3$H$_7$           | 4-Cl-phenyl                                |
| 762 | H | OCH$_3$           | NHCH$_3$           | O | 1 | C$_3$H$_7$           | 4-CH$_3$-phenyl                            |
| 763 | H | OCH$_3$           | NHCH$_3$           | O | 1 | C$_3$H$_7$           | 4-OCH$_3$-phenyl                           |
| 764 | H | OCH$_3$           | NHCH$_3$           | O | 1 | C$_3$H$_7$           | 4-CF$_3$-phenyl                            |
| 765 | H | OC$_2$H$_5$       | NHCH$_3$           | S | 1 | CH$_3$               | 4-Cl-phenyl                                |
| 766 | H | OC$_2$H$_5$       | NHCH$_3$           | S | 1 | CH$_3$               | 4-CH$_3$-phenyl                            |
| 767 | H | OC$_2$H$_5$       | NHCH$_3$           | S | 1 | CH$_3$               | 4-OCH$_3$-phenyl                           |
| 768 | H | OC$_2$H$_5$       | NHCH$_3$           | S | 1 | CH$_3$               | 4-CF$_3$-phenyl                            |
| 769 | H | OC$_2$H$_5$       | NHCH$_3$           | S | 1 | C$_2$H$_5$           | 4-Cl-phenyl                                |

-continued

| | | | | | | | |
|---|---|---|---|---|---|---|---|
| 770 | H | OC$_2$H$_5$ | NHCH$_3$ | S | 1 | C$_2$H$_5$ | 4-CH$_3$-phenyl |
| 771 | H | OC$_2$H$_5$ | NHCH$_3$ | S | 1 | C$_2$H$_5$ | 4-OCH$_3$-phenyl |
| 772 | H | OC$_2$H$_5$ | NHCH$_3$ | S | 1 | C$_2$H$_5$ | 4-CF$_3$-phenyl |
| 773 | H | OCH$_3$ | NHCH$_3$ | O | 1 | CH$_3$ | 2,5-(CH$_3$)$_2$-phenyl |
| 774 | H | OC$_2$H$_5$ | NHCH$_3$ | O | 1 | CH$_3$ | 2,5-(CH$_3$)$_2$-phenyl |
| 775 | H | OCH$_3$ | NHCH$_3$ | O | 1 | C$_2$H$_5$ | 2,5-(CH$_3$)$_2$-phenyl |
| 776 | H | OCH$_3$ | NHCH$_3$ | S | 1 | CH$_3$ | 2,5-(CH$_3$)$_2$-phenyl |
| 777 | H | OCH$_3$ | NHCH$_3$ | O | 1 | CH$_3$ | 3,5-(CH$_3$)$_2$-phenyl |
| 778 | H | OC$_2$H$_5$ | NHCH$_3$ | O | 1 | CH$_3$ | 3,5-(CH$_3$)$_2$-phenyl |
| 779 | H | OCH$_3$ | NHCH$_3$ | S | 1 | CH$_3$ | 3,5-(CH$_3$)$_2$-phenyl |
| 780 | H | OCH$_3$ | NHCH$_3$ | O | 1 | C$_2$H$_5$ | 3,5-(CH$_3$)$_2$-phenyl |
| 781 | H | OCH$_3$ | NHCH$_3$ | O | 1 | CH$_3$ | 3-CH$_3$-4-OCH$_3$-phenyl |
| 782 | H | OC$_2$H$_5$ | NHCH$_3$ | O | 1 | CH$_3$ | 3-CH$_3$-4-OCH$_3$-phenyl |
| 783 | H | OCH$_3$ | NHCH$_3$ | O | 1 | C$_2$H$_5$ | 3-CH$_3$-4-OCH$_3$-phenyl |
| 784 | H | OCH$_3$ | NHCH$_3$ | S | 1 | CH$_3$ | 3-CH$_3$-4-OCH$_3$-phenyl |
| 785 | H | OCH$_3$ | NHCH$_3$ | O | 1 | CH$_3$ | 2-Naphthyl |
| 786 | H | OCH$_3$ | NHCH$_3$ | O | 1 | C$_2$H$_5$ | 2-Naphthyl |
| 787 | H | OCH$_3$ | NHCH$_3$ | S | 1 | CH$_3$ | 2-Naphthyl |
| 788 | H | OC$_2$H$_5$ | NHCH$_3$ | O | 1 | CH$_3$ | 2-Naphthyl |
| 789 | H | OCH$_3$ | SCH$_3$ | O | 1 | C$_2$H$_5$ | 4-Cl-phenyl |
| 790 | H | OCH$_3$ | SCH$_3$ | O | 1 | C$_2$H$_5$ | 4-CH$_3$-phenyl |
| 791 | H | OCH$_3$ | SCH$_3$ | O | I | C$_2$H$_5$ | 4-OCH$_3$-phenyl |
| 792 | H | OCH$_3$ | SCH$_3$ | O | 1 | C$_2$H$_5$ | 4-CF$_3$-phenyl |
| 793 | H | Cl | NHCH$_3$ | O | 1 | CH$_3$ | 4-Cl-phenyl |
| 794 | H | SCH$_3$ | NHCH$_3$ | O | 1 | CH$_3$ | 4-Cl-phenyl |
| 795 | H | SCH$_3$ | NHCH$_3$ | O | 1 | C$_2$H$_5$ | 4-Cl-phenyl |
| 796 | H | NHCH$_3$ | NHCH$_3$ | O | 1 | CH$_3$ | 4-Cl-phenyl |
| 797 | H | SCH$_3$ | NHCH$_3$ | O | 1 | CH$_3$ | 4-CF$_3$-phenyl |
| 798 | H | NHCH$_3$ | NHCH$_3$ | O | 1 | CH$_3$ | 4-CF$_3$-phenyl |
| 799 | H | SCH$_3$ | NHCH$_3$ | O | 1 | CH$_3$ | 3-CF$_3$-phenyl |
| 800 | H | NHCH$_3$ | NHCH$_3$ | O | 1 | CH$_3$ | 3-CF$_3$-phenyl |
| 801 | H | SCH$_3$ | NHCH$_3$ | O | 1 | CH$_3$ | 4-CH$_3$-phenyl |
| 802 | H | NHCH$_3$ | NHCH$_3$ | O | 1 | CH$_3$ | 4-CH$_3$-phenyl |
| 803 | H | SCH$_3$ | NHCH$_3$ | O | 1 | CH$_3$ | 4-OCH$_3$-phenyl |
| 804 | H | NHCH$_3$ | NHCH$_3$ | O | 1 | CH$_3$ | 4-OCH$_3$-phenyl |
| 805 | H | SCH$_3$ | NHCH$_3$ | O | 1 | CH$_3$ | 4-OCHF$_2$-phenyl |
| 806 | H | NHCH$_3$ | NHCH$_3$ | O | 1 | CH$_3$ | 4-OCHF$_2$-phenyl |
| 867 | H | Cl | NHCH$_3$ | O | 1 | CH$_3$ | 4-NO$_2$-phenyl |
| 808 | H | SCH$_3$ | NHCH$_3$ | O | 1 | CH$_3$ | 4-NO$_2$-phenyl |
| 809 | H | SCH$_3$ | NHCH$_3$ | O | 1 | CH$_3$ | 3,4-(CH$_3$)$_2$-phenyl |
| 810 | H | NHCH$_3$ | NHCH$_3$ | O | 1 | CH$_3$ | 3,4-(CH$_3$)$_2$-phenyl |
| 811 | H | SCH$_3$ | NHCH$_3$ | O | 1 | CH$_3$ | 3,4-Cl$_2$-phenyl |
| 812 | H | NHCH$_3$ | NHCH$_3$ | O | 1 | CH$_3$ | 3,4-Cl$_2$-phenyl |
| 813 | H | OCH$_3$ | NHCH$_3$ | O | 1 | SCH$_3$ | 4-Cl-phenyl |
| 814 | H | OC$_2$H$_5$ | NHCH$_3$ | O | 1 | SCH$_3$ | 4-Cl-phenyl |
| 815 | H | OCH$_3$ | NHCH$_3$ | O | 1 | SC$_2$H$_5$ | 4-Cl-phenyl |
| 816 | H | OCH$_3$ | NHCH$_3$ | O | 1 | SC$_4$H$_9$ | 4-Cl-phenyl |
| 817 | H | OCH$_3$ | OCH$_3$ | O | 1 | SCH$_3$ | 4-Cl-phenyl |
| 818 | H | OCH$_3$ | NHCH$_3$ | S | 1 | SCH$_3$ | 4-Cl-phenyl |
| 819 | H | OCH$_3$ | NHCH$_3$ | O | 1 | SCH$_3$ | 4-CH$_3$-phenyl |
| 820 | H | OC$_2$H$_5$ | NHCH$_3$ | O | 1 | SCH$_3$ | 4-CH$_3$-phenyl |
| 821 | H | OCH$_3$ | OCH$_3$ | O | 1 | SCH$_3$ | 4-CH$_3$-phenyl |
| 822 | H | OCH$_3$ | NHCH$_3$ | O | 1 | SC$_2$H$_5$ | 4-CH$_3$-phenyl |
| 823 | H | OCH$_3$ | NHCH$_3$ | S | 1 | SCH$_3$ | 4-CH$_3$-phenyl |
| 824 | H | OCH$_3$ | NHCH$_3$ | O | 1 | SCH$_3$ | 4-CF$_3$-phenyl |
| 825 | H | OC$_2$H$_5$ | NHCH$_3$ | O | 1 | SCH$_3$ | 4-CF$_3$-phenyl |
| 826 | H | OCH$_3$ | NHCH$_3$ | O | 1 | SC$_2$H$_5$ | 4-CF$_3$-phenyl |
| 827 | H | OCH$_3$ | NHCH$_3$ | S | 1 | SCH$_3$ | 4-CF$_3$-phenyl |
| 828 | H | OCH$_3$ | OCH$_3$ | O | 1 | SCH$_3$ | 4-CF$_3$-phenyl |
| 829 | H | OCH$_3$ | NHCH$_3$ | O | 1 | SCH$_3$ | 3-CF$_3$-phenyl |
| 830 | H | OC$_2$H$_5$ | NHCH$_3$ | O | 1 | SCH$_3$ | 3-CF$_3$-phenyl |
| 831 | H | OCH$_3$ | NHCH$_3$ | O | 1 | SC$_2$H$_5$ | 3-CF$_3$-phenyl |
| 832 | H | OCH$_3$ | NHCH$_3$ | S | 1 | SCH$_3$ | 3-CF$_3$-phenyl |
| 833 | H | OCH$_3$ | NHCH$_3$ | O | 1 | SOCH$_3$ | 4-Cl-phenyl |
| 834 | H | OCH$_3$ | NHCH$_3$ | O | 1 | SO$_2$CH$_3$ | 4-Cl-phenyl |
| 835 | H | OCH$_3$ | NHCH$_3$ | O | 1 | SOC$_2$H$_5$ | 4-Cl-phenyl |
| 836 | H | OCH$_3$ | NHCH$_3$ | O | 1 | SO$_2$C$_2$H$_5$ | 4-Cl-phenyl |
| 837 | H | OCH$_3$ | NHCH$_3$ | O | 1 | SCH$_3$ | 4-OCH$_3$-phenyl |
| 838 | H | OCH$_3$ | NHCH$_3$ | S | 1 | SCH$_3$ | 4-OCH$_3$-phenyl |
| 839 | H | OCH$_3$ | NHCH$_3$ | O | 1 | SC$_2$H$_5$ | 4-OCH$_3$-phenyl |
| 840 | H | OC$_2$H$_5$ | NHCH$_3$ | O | 1 | SCH$_3$ | 4-OCH$_3$-phenyl |
| 841 | H | OCH$_3$ | NHCH$_3$ | O | 1 | SCH$_3$ | 4-OCHF$_2$-phenyl |
| 842 | H | OCH$_3$ | NHCH$_3$ | O | 1 | SC$_2$H$_5$ | 4-OCHF$_2$-phenyl |
| 843 | H | OCH$_3$ | NHCH$_3$ | S | 1 | SCH$_3$ | 4-OCHF$_2$-phenyl |
| 844 | H | OC$_2$H$_5$ | NHCH$_3$ | O | 1 | SCH$_3$ | 4-OCHF$_2$-phenyl |
| 845 | H | OCH$_3$ | NHCH$_3$ | O | 1 | SCH$_3$ | 3-Cl-phenyl |
| 846 | H | OCH$_3$ | NHCH$_3$ | O | 1 | SC$_2$H$_5$ | 3-Cl-phenyl |
| 847 | H | OCH$_3$ | NHCH$_3$ | O | 1 | SCH$_3$ | 2-Cl-phenyl |
| 848 | H | OCH$_3$ | NHCH$_3$ | O | 1 | SC$_2$H$_5$ | 2-Cl-phenyl |

-continued

| No. | | | | | | | |
|---|---|---|---|---|---|---|---|
| 849 | H | OCH$_3$ | NHCH$_3$ | O | 1 | SCH$_3$ | 4-C$_2$H$_5$-phenyl |
| 850 | H | OC$_2$H$_5$ | NHCH$_3$ | O | 1 | SCH$_3$ | 4-C$_2$H$_5$-phenyl |
| 851 | H | OCH$_3$ | NHCH$_3$ | O | 1 | SC$_2$H$_5$ | 4-OC$_2$H$_5$-phenyl |
| 852 | H | OCH$_3$ | NHCH$_3$ | O | 1 | SCH$_3$ | 4-OC$_2$H$_5$-phenyl |
| 853 | H | OCH$_3$ | NHCH$_3$ | O | 1 | SCH$_3$ | 3,4-(CH$_3$)$_2$-phenyl |
| 854 | H | OCH$_3$ | NHCH$_3$ | O | 1 | SC$_2$H$_5$ | 3,4-(CH$_3$)$_2$-phenyl |
| 855 | H | OCH$_3$ | NHCH$_3$ | O | 1 | SCH$_3$ | 3-Cl-4-OCH$_3$-phenyl |
| 856 | H | OCH$_3$ | NHCH$_3$ | O | 1 | SC$_2$H$_5$ | 3-Cl-4-OCH$_3$-phenyl |
| 857 | H | OCH$_3$ | NHCH$_3$ | O | 1 | SCH$_3$ | 3,4-Cl$_2$-phenyl |
| 858 | H | OCH$_3$ | NHCH$_3$ | O | 1 | SC$_2$H$_5$ | 3,4-Cl$_2$-phenyl |
| 859 | H | OCH$_3$ | NHCH$_3$ | O | 1 | SC$_2$H$_5$ | 4-NO$_2$-phenyl |
| 860 | H | OCH$_3$ | NHCH$_3$ | O | 1 | SCH$_3$ | 4-NO$_2$-phenyl |
| 861 | H | OCH$_3$ | NHCH$_3$ | O | 1 | SCH$_3$ | 4-Phenoxyphenyl |
| 862 | H | OCH$_3$ | NHCH$_3$ | O | 1 | SC$_2$H$_5$ | 4-Phenoxyphenyl |
| 863 | H | OCH$_3$ | NHCH$_3$ | O | 1 | SCH$_3$ | 2-Furyl |
| 864 | H | OCH$_3$ | NHCH$_3$ | O | 1 | SCH$_3$ | 2-Thienyl |
| 865 | H | OCH$_3$ | NHCH$_3$ | O | 1 | SCH$_3$ | 2-Pyridyl |
| 866 | H | OCH$_3$ | NHCH$_3$ | O | 1 | SCH$_3$ | 3-Pyridyl |
| 867 | H | OCH$_3$ | NHCH$_3$ | O | 1 | SCH$_3$ | 4-Pyridyl |
| 868 | H | OCH$_3$ | NHCH$_3$ | O | 1 | SCH$_3$ | 2-Pyridazinyl |
| 869 | H | OCH$_3$ | NHCH$_3$ | O | 1 | SCH$_3$ | 2-Pyrimidinyl |
| 870 | H | OCH$_3$ | NHCH$_3$ | O | 1 | SCH$_3$ | 5-Pyrimidinyl |
| 871 | H | OCH$_3$ | NHCH$_3$ | O | 1 | SCH$_3$ | 1-Naphthyl |
| 872 | H | OCH$_3$ | NHCH$_3$ | O | 1 | SCH$_3$ | 2-Naphthyl |
| 873 | H | OCH$_3$ | NHCH$_3$ | O | L | CH$_3$, SCH$_3$ | |
| 874 | H | OCH$_3$ | NHCH$_3$ | O | 1 | CH$_3$, SC$_2$H$_5$ | |
| 875 | H | OCH$_3$ | NHCH$_3$ | O | 1 | CH$_3$, SC$_4$H$_9$ | |
| 876 | H | OCH$_3$ | NHCH$_3$ | O | 1 | C$_2$H$_5$, SCH$_3$ | |
| 877 | H | OCH$_3$ | NHCH$_3$ | O | 1 | C$_2$H$_5$, SC$_2$H$_5$ | |
| 878 | H | OCH$_3$ | NHCH$_3$ | O | 1 | C$_2$H$_5$, SC$_4$H$_9$ | |
| 879 | H | OCH$_3$ | NHCH$_3$ | O | 1 | C$_4$H$_9$, SCH$_3$ | |
| 880 | H | OCH$_3$ | NHCH$_3$ | O | 1 | C$_4$H$_9$, SC$_2$H$_5$ | |
| 881 | H | OCH$_3$ | NHCH$_3$ | O | 1 | C$_4$H$_9$, SC$_4$H$_9$ | |
| 882 | H | OCH$_3$ | NHCH$_3$ | O | 1 | CH$_3$ | N-morpholinyl |
| 883 | H | OCH$_3$ | NHCH$_3$ | O | 1 | CH$_3$ | 2,6-dimethylmorpholinyl (cis) |
| 884 | H | OCH$_3$ | NHCH$_3$ | O | 1 | CH$_3$ | 2,6-dimethylmorpholinyl (trans) |
| 885 | H | OCH$_3$ | NHCH$_3$ | O | 1 | CH$_3$ | 4-methylpiperazinyl |
| 886 | H | OCH$_3$ | NHCH$_3$ | O | 1 | C$_2$H$_5$ | N-morpholinyl |
| 887 | H | OCH$_3$ | NHCH$_3$ | O | 1 | C$_2$H$_5$ | 2,6-dimethylmorpholinyl |

-continued

| | | | | | | | |
|---|---|---|---|---|---|---|---|
| 888 | H | OCH₃ | NHCH₃ | O | 1 | C₂H₅ | 2,6-dimethyl-4-N-morpholinyl |
| 889 | H | OCH₃ | NHCH₃ | O | 1 | C₂H₅ | 4-methylpiperazin-1-yl |
| 890 | H | OCH₃ | NHCH₃ | O | 1 | C₄H₉ | morpholinyl |
| 891 | H | OCH₃ | NHCH₃ | O | 1 | C₄H₉ | 2,6-dimethyl-4-N-morpholinyl |
| 892 | H | OCH₃ | NHCH₃ | O | 1 | C₄H₉ | 2,6-dimethyl-4-N-morpholinyl |
| 893 | H | OCH₃ | NHCH₃ | O | 1 | C₄H₉ | 4-methylpiperazin-1-yl |
| 894 | H | OCH₃ | NHCH₃ | O | 1 | CF₃ | morpholinyl |
| 895 | H | OCH₃ | NHCH₃ | O | 1 | CF₃ | 2,6-dimethyl-4-N-morpholinyl |
| 896 | H | OCH₃ | NHCH₃ | O | 1 | CF₃ | 2,6-dimethyl-4-N-morpholinyl |
| 897 | H | OCH₃ | NHCH₃ | O | 1 | CF₃ | 4-methylpiperazin-1-yl |

-continued
| | | | | | | | |
|---|---|---|---|---|---|---|---|
| 898 | H | OCH₃ | NHCH₃ | O | 1 | 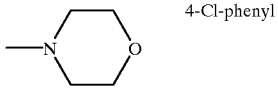 | 4-Cl-phenyl |
| 899 | H | OCH₃ | NHCH₃ | O | 1 | 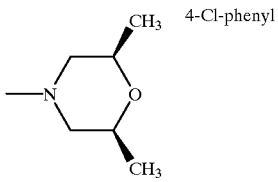 | 4-Cl-phenyl |
| 900 | H | OCH₃ | NHCH₃ | O | 1 | 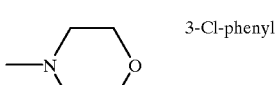 | 3-Cl-phenyl |
| 901 | H | OCH₃ | NHCH₃ | O | 1 | 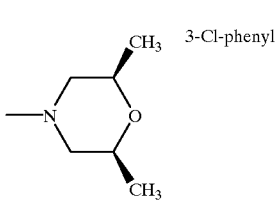 | 3-Cl-phenyl |
| 902 | H | OCH₃ | NHCH₃ | O | 1 | CH₃ | 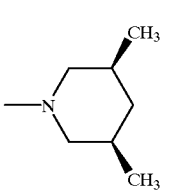 |
| 903 | H | OCH₃ | NHCH₃ | O | 1 | CH₃ | 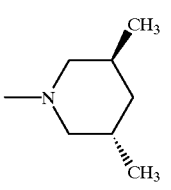 |
| 904 | H | OCH₃ | NHCH₃ | O | 1 | 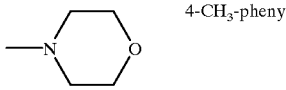 | 4-CH₃-phenyl |
| 905 | H | OCH₃ | NHCH₃ | O | 1 | 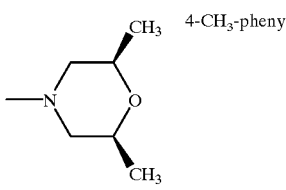 | 4-CH₃-phenyl |
| 906 | H | OCH₃ | NHCH₃ | O | 1 | 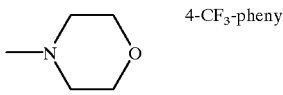 | 4-CF₃-phenyl |
| 907 | H | OCH₃ | NHCH₃ | O | 1 | 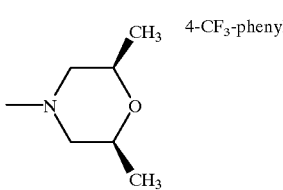 | 4-CF₃-phenyl |

-continued

| | | | | | | | |
|---|---|---|---|---|---|---|---|
| 908 | H | OCH$_3$ | NHCH$_3$ | O | 1 | 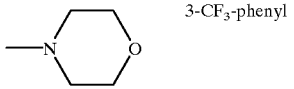 | 3-CF$_3$-phenyl |
| 909 | H | OCH$_3$ | NHCH$_3$ | O | 1 | 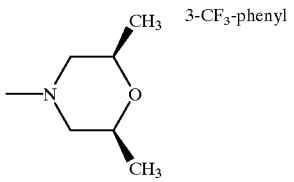 | 3-CF$_3$-phenyl |
| 910 | H | OCH$_3$ | NHCH$_3$ | O | 1 | 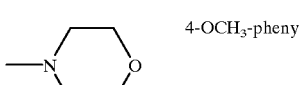 | 4-OCH$_3$-phenyl |
| 911 | H | OCH$_3$ | NHCH$_3$ | O | 1 | 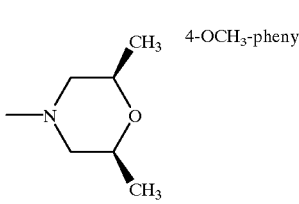 | 4-OCH$_3$-phenyl |
| 912 | H | OCH$_3$ | NHCH$_3$ | O | 1 | 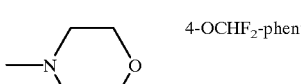 | 4-OCHF$_2$-phenyl |
| 913 | H | OCH$_3$ | NHCH$_3$ | O | 1 | 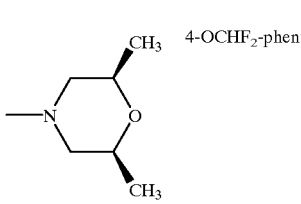 | 4-OCHF$_2$-phenyl |
| 914 | H | OCH$_3$ | NHCH$_3$ | O | 1 | 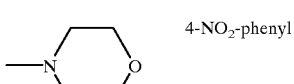 | 4-NO$_2$-phenyl |
| 915 | H | OCH$_3$ | NHCH$_3$ | O | 1 | 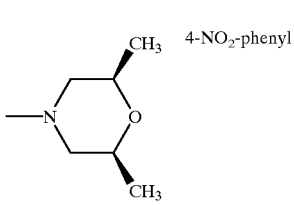 | 4-NO$_2$-phenyl |
| 916 | H | OCH$_3$ | NHCH$_3$ | O | 1 | NHCH$_3$ | 4-Cl-phenyl |
| 917 | H | OC$_2$H$_5$ | NHCH$_3$ | O | 1 | NHCH$_3$ | 4-Cl-phenyl |
| 918 | H | OCH$_3$ | NHCH$_3$ | O | 1 | NHC$_2$H$_5$ | 4-Cl-phenyl |
| 919 | H | OCH$_3$ | NHCH$_3$ | O | 1 | NHC$_4$H$_9$ | 4-Cl-phenyl |
| 920 | H | OCH$_3$ | NHCH$_3$ | O | 1 | NHCH$_3$ | 4-CF$_3$-phenyl |
| 921 | H | OCH$_3$ | NHCH$_3$ | O | 1 | NHC$_2$H$_5$ | 4-CF$_3$-phenyl |
| 922 | H | OCH$_3$ | NHCH$_3$ | O | 1 | NHCH$_3$ | 3-CF$_3$-phenyl |
| 923 | H | OCH$_3$ | NHCH$_3$ | O | 1 | NHC$_2$H$_5$ | 3-CF$_3$-phenyl |
| 924 | H | OCH$_3$ | OCH$_3$ | O | 1 | NHCH$_3$ | 4-CH$_3$-phenyl |
| 925 | H | OCH$_3$ | NHCH$_3$ | O | 1 | NHC$_2$H$_5$ | 4-CH$_3$-phenyl |
| 926 | H | OCH$_3$ | NHCH$_3$ | O | 1 | NHCH$_3$ | 4-OCH$_3$-phenyl |
| 927 | H | OCH$_3$ | NHCH$_3$ | O | 1 | NHC$_2$H$_5$ | 4-OCH$_3$-phenyl |
| 928 | H | OCH$_3$ | NHCH$_3$ | O | 1 | NHCH$_3$ | 4-OCHF$_2$-phenyl |
| 929 | H | OCH$_3$ | NHCH$_3$ | O | 1 | NHC$_2$H$_5$ | 4-OCHF$_2$-phenyl |
| 930 | H | OCH$_3$ | NHCH$_3$ | O | 1 | NHCH$_3$ | 4-NO$_2$-phenyl |
| 931 | H | OCH$_3$ | OCH$_3$ | O | 1 | NHC$_2$H$_5$ | 4-NO$_2$-phenyl |
| 932 | H | OCH$_3$ | NHCH$_3$ | O | 1 | NHCH$_3$ | 3,4-(CH$_3$)$_2$-phenyl |
| 933 | H | OCH$_3$ | NHCH$_3$ | O | 1 | NHC$_2$H$_5$ | 3,4-(CH$_3$)$_2$-phenyl |
| 934 | H | OCH$_3$ | NHCH$_3$ | O | 1 | NHCH$_3$ | 3,4-Cl$_2$-phenyl |

-continued

| Comp. No. | X | R¹ | Y | Z | n | R² | R¹² | R¹³ |
|---|---|---|---|---|---|---|---|---|
| 935 | H | OCH₃ | NHCH₃ | O | 1 | NHC₂H₅ | | 3,4-Cl₂-phenyl |
| 936 | H | OCH₃ | NHCH₃ | O | 1 | COCH₃ | CH₃ | 2,6-dimethylmorpholin-4-yl |
| 937 | H | OCH₃ | NHCH₃ | O | 1 | COCH₃ | CH₃ | 2,6-dimethylmorpholin-4-yl (cis/trans) |
| 938 | H | OCH₃ | NHCH₃ | O | 1 | COCH₃ | CH₃ | 2,6-dimethylmorpholin-4-yl (trans) |
| 939 | H | OCH₃ | NHCH₃ | O | 1 | COCH₃ | CH₃ | 3,5-dimethylpiperidin-1-yl |
| 940 | H | OCH₃ | NHCH₃ | O | 1 | CH₃ | CH₃ | 4-Cl-phenyl |
| 941 | H | OCH₃ | NHCH₃ | O | 1 | COCH₃ | CH₃ | 4-Cl-phenyl |
| 942 | H | OCH₃ | NHCH₃ | O | 1 | COC₂H₅ | CH₃ | 4-Cl-phenyl |
| 943 | H | OCH₃ | NHCH₃ | S | 1 | COCH₃ | CH₃ | 4-Cl-phenyl |
| 944 | H | OCH₃ | NHCH₃ | O | 1 | CO-phenyl | CH₃ | 4-Cl-phenyl |
| 945 | H | OC₂H₅ | NHCH₃ | O | 1 | COCH₃ | CH₃ | 4-Cl-phenyl |
| 946 | H | OCH₃ | NHCH₃ | O | 1 | COCH₃ | C₂H₅ | 4-Cl-phenyl |
| 947 | H | OCH₃ | OCH₃ | O | 1 | COCH₃ | CH₃ | 4-Cl-phenyl |
| 948 | H | OCH₃ | SCH₃ | O | 1 | COCH₃ | CH₃ | 4-Cl-phenyl |
| 949 | H | OCH₃ | NHCH₃ | O | 1 | CH₃ | CH₃ | 4-CH₃-phenyl |
| 950 | H | OCH₃ | NHCH₃ | O | 1 | COCH₃ | CH₃ | 4-CH₃-phenyl |
| 951 | H | OCH₃ | NHCH₃ | O | 1 | COCH₃ | C₂H₅ | 4-CH₃-phenyl |
| 952 | H | OCH₃ | OCH₃ | O | 1 | COCH₃ | CH₃ | 4-CH₃-phenyl |
| 953 | H | OCH₃ | SCH₃ | O | 1 | COCH₃ | CH₃ | 4-CH₃-phenyl |
| 954 | H | OCH₃ | NHCH₃ | S | 1 | COCH₃ | CH₃ | 4-CH₃-phenyl |
| 955 | H | OCH₃ | NHCH₃ | O | 1 | CH₃ | CH₃ | 4-CF₃-phenyl |
| 956 | H | OCH₃ | NHCH₃ | O | 1 | COCH₃ | CH₃ | 4-CF₃-phenyl |
| 957 | H | OCH₃ | NHCH₃ | O | 1 | COCH₃ | C₂H₅ | 4-CF₃-phenyl |
| 958 | H | OCH₃ | OCH₃ | O | 1 | COCH₃ | CH₃ | 4-CF₃-phenyl |
| 959 | H | OCH₃ | SCH₃ | O | 1 | COCH₃ | CH₃ | 4-CF₃-phenyl |
| 960 | H | OCH₃ | NHCH₃ | S | 1 | COCH₃ | CH₃ | 4-CF₃-phenyl |
| 961 | H | OCH₃ | NHCH₃ | O | 1 | CH₃ | CH₃ | 4-OCH₃-phenyl |
| 962 | H | OCH₃ | NHCH₃ | O | 1 | COCH₃ | CH₃ | 4-OCH₃-phenyl |
| 963 | H | OCH₃ | NHCH₃ | O | 1 | COCH₃ | C₂H₅ | 4-OCH₃-phenyl |
| 964 | H | OCH₃ | OCH₃ | O | 1 | COCH₃ | CH₃ | 4-OCH₃-phenyl |
| 965 | H | OCH₃ | SCH₃ | O | 1 | COCH₃ | CH₃ | 4-OCH₃-phenyl |
| 966 | H | OCH₃ | NHCH₃ | S | 1 | COCH₃ | CH₃ | 4-OCH₃-phenyl |
| 967 | H | OCH₃ | NHCH₃ | O | 1 | COCH₃ | CH₃ | 3-CF₃-phenyl |
| 968 | H | OCH₃ | NHCH₃ | O | 1 | COCH₃ | CH₃ | 3,4-Cl₂-phenyl |
| 969 | H | OCH₃ | NHCH₃ | O | 1 | COCH₃ | CH₃ | 3,4-(CH₃)₂-phenyl |
| 970 | H | OCH₃ | NHCH₃ | O | 1 | COCH₃ | CH₃ | 4-OCHF₂-phenyl |
| 971 | H | OCH₃ | NHCH₃ | O | 1 | COCH₃ | CH₃ | 4-Phenoxyphenyl |
| 972 | H | OCH₃ | NHCH₃ | O | 1 | COCH₃ | CH₃ | CH₃ |
| 973 | H | OCH₃ | NHCH₃ | O | 1 | COCH₃ | CH₃ | C₄H₉ |
| 974 | H | OCH₃ | NHCH₃ | O | 1 | COCH₃ | COCH₃ | 4-Cl-phenyl |

-continued

| | | | | | | | |
|---|---|---|---|---|---|---|---|
| 975 | H | OCH₃ | NHCH₃ | O | 1 | COCH₃ | CO-phenyl | 4-Cl-phenyl |
| 976 | H | OCH₃ | NHCH₃ | O | 1 | COCH₃ | SCH₃ | 4-Cl-phenyl |
| 977 | H | OCH₃ | NHCH₃ | S | 1 | COCH₃ | SCH₃ | 4-Cl-phenyl |
| 978 | H | OCH₃ | NHCH₃ | O | 1 | COCH₃ | SCH₃ | 4-CH₃-phenyl |
| 979 | H | OCH₃ | NHCH₃ | O | 1 | COCH₃ | SCH₃ | 4-CF₃-phenyl |
| 980 | H | OCH₃ | NHCH₃ | O | 1 | COCH₃ | SCH₃ | 4-OCH₃-phenyl |

| Comp. No. | X | $R^1$ | Y | Z | n | M | $R^{14}$ | $R^{15}$ |
|---|---|---|---|---|---|---|---|---|
| 981 | H | OCH₃ | NHCH₃ | O | 1 | O | CH₃ | 4-Cl-phenyl |
| 982 | H | OCH₃ | NHCH₃ | O | 1 | O | Cyclopropyl | 4-Cl-phenyl |
| 983 | H | OCH₃ | NHCH₃ | O | 1 | S | CH₃ | 4-Cl-phenyl |
| 984 | H | OCH₃ | NHCH₃ | O | 1 | S | Cyclopropyl | 4-Cl-phenyl |
| 985 | H | OCH₃ | NHCH₃ | O | 1 | S | SCH₃ | 4-Cl-phenyl |
| 986 | H | OCH₃ | NHCH₃ | O | 1 | S | Phenyl | 4-Cl-phenyl |
| 987 | H | OCH₃ | NHCH₃ | O | 1 | NH | Cyclopropyl | 4-Cl-phenyl |
| 988 | H | OCH₃ | OCH₃ | O | 1 | S | CH₃ | 4-Cl-phenyl |
| 989 | H | OCH₃ | OCH₃ | O | 1 | S | Cyclopropyl | 4-Cl-phenyl |
| 990 | H | OCH₃ | OCH₃ | O | 1 | S | SCH₃ | 4-Cl-phenyl |
| 991 | H | OCH₃ | SCH₃ | O | 1 | S | CH₃ | 4-Cl-phenyl |
| 992 | H | OCH₃ | SCH₃ | O | 1 | S | Cyclopropyl | 4-Cl-phenyl |
| 993 | H | OCH₃ | SCH₃ | O | 1 | S | SCH₃ | 4-Cl-phenyl |
| 994 | H | OCH₃ | NHCH₃ | O | 1 | S | CH₃ | 4-CH₃-phenyl |
| 995 | H | OCH₃ | NHCH₃ | O | 1 | S | Cyclopropyl | 4-CH₃-phenyl |
| 996 | H | OCH₃ | NHCH₃ | O | 1 | S | SCH₃ | 4-CH₃-phenyl |
| 997 | H | OCH₃ | NHCH₃ | O | 1 | S | CH₃ | 4-CF₃-phenyl |
| 998 | H | OCH₃ | NHCH₃ | O | 1 | S | Cyclopropyl | 4-CF₃-phenyl |
| 999 | H | OCH₃ | NHCH₃ | O | 1 | S | SCH₃ | 4-CF₃-phenyl |
| 1006 | H | OCH₃ | NHCH₃ | O | 1 | S | CH₃ | 4-OCH₃-phenyl |
| 1001 | H | OCH₃ | NHCH₃ | O | 1 | S | Cyclopropyl | 4-OCH₃-phenyl |
| 1002 | H | OCH₃ | NHCH₃ | O | 1 | S | SCH₃ | 4-OCH₃-phenyl |
| 1003 | H | OCH₃ | NHCH₃ | O | 1 | S | CH₃ | CH₃ |
| 1004 | H | OCH₃ | NHCH₃ | O | 1 | S | Cyclopropyl | CH₃ |
| 1005 | H | OCH₃ | NHCH₃ | O | 1 | S | SCH₃ | CH₃ |
| 1006 | H | OCH₃ | NHCH₃ | O | 1 | S | CH₃ | C₄H₉ |
| 1007 | H | OCH₃ | NHCH₃ | O | 1 | S | Cyclopropyl | C₄H₉ |
| 1008 | H | OCH₃ | NHCH₃ | O | 1 | S | SCH₃ | C₄H₉ |
| 1009 | H | OCH₃ | NHCH₃ | O | 1 | S | Cyclopropyl | 4-OC₂H₅-phenyl |
| 1010 | H | OCH₃ | NHCH₃ | O | 1 | S | Cyclopropyl | 4-Phenoxyphenyl |

| Comp. No. | X | $R^1$ | Y | Z | n | M | Q |
|---|---|---|---|---|---|---|---|
| 1011 | H | OCH₃ | NHCH₃ | O | 1 | O | C₄H₉ |
| 1012 | H | OCH₃ | NHCH₃ | O | 1 | O | CH₂CH₂CH₂CH₂Cl |
| 1013 | H | OCH₃ | NHCH₃ | O | 1 | O | CH₂CH₂OC₂H₅ |
| 1014 | H | OCH₃ | NHCH₃ | O | 1 | O | CH₂CH₂SC₂H₅ |
| 1015 | H | OCH₃ | NHCH₃ | O | 1 | O | CH₂CH₂NHC₂H₅ |
| 1016 | H | OCH₃ | NHCH₃ | O | 1 | O | Benzyl |
| 1017 | H | OCH₃ | NHCH₃ | O | 1 | O | 2-CH₃-benzyl |
| 1018 | H | OCH₃ | NHCH₃ | O | 1 | O | 3-CH₃-benzyl |
| 1019 | H | OCH₃ | NHCH₃ | O | 1 | O | 4-CH₃-benzyl |
| 1020 | H | OCH₃ | NHCH₃ | O | 1 | O | Phenethyl |
| 1021 | H | OCH₃ | NHCH₃ | O | 1 | S | Benzyl |
| 1022 | H | OCH₃ | NHCH₃ | O | 1 | NH | Benzyl |
| 1023 | H | OCH₃ | NHCH₃ | O | 1 | O | 3-Pyridylmethyl |
| 1024 | H | OCH₃ | NHCH₃ | O | 1 | O | CH₂CH=CH₂ |
| 1025 | H | OCH₃ | NHCH₃ | O | 1 | O | CH₂CH=CCl₂ |
| 1026 | H | OCH₃ | NHCH₃ | O | 1 | O | CH₂CH=CH-phenyl |
| 1027 | H | OCH₃ | NHCH₃ | O | 1 | O | CH₂C≡CH |
| 1028 | H | OCH₃ | NHCH₃ | O | 1 | O | CH₂C≡C—CH₃ |
| 1029 | H | OCH₃ | NHCH₃ | O | 1 | O | CH₂C≡C-phenyl |
| 1030 | H | OCH₃ | NHCH₃ | O | 1 | O | Benzoyl |
| 1031 | H | OCH₃ | NHCH₃ | O | 1 | O | 4-Cl-benzoyl |
| 1032 | H | OCH₃ | NHCH₃ | O | 1 | O | 4-CH₃-benzoyl |
| 1033 | H | OCH₃ | NHCH₃ | O | 1 | O | 4-CF₃-benzoyl |
| 1034 | H | OCH₃ | NHCH₃ | O | 1 | O | 4-OCH₃-benzoyl |
| 1035 | H | OCH₃ | NHCH₃ | O | 1 | O | CO-benzyl |
| 1036 | H | OCH₃ | NHCH₃ | O | 1 | S | CO-benzyl |
| 1037 | H | OCH₃ | NHCH₃ | O | 1 | NH | CO-benzyl |
| 1038 | H | OCH₃ | NHCH₃ | O | 1 | O | 4-Toluenesulfonyl |
| 1039 | H | OCH₃ | NHCH₃ | O | 1 | O | Benzylsulfonyl |
| 1040 | H | OCH₃ | NHCH₃ | O | 1 | NH | 4-Toluenesulfonyl |

| Comp. No. | Physical data |
|---|---|
| 474 | 84–87° C. |
| 475 | 105–106° C. |
| 476 | 117–118° C. |
| 477 | 2.23(3H, s), 3.39(3H, s), 3.71(3H, s), 5.24(1H, s), 5.27(1H, d, J=12.2), 5.51(1H, d, J=12.2), 7.30–7.54(6H, m), 7.58(2H, m) |
| 478 | 120–122° C. |
| 479 | 2.23(3H, s), 3.75(3H, s), 3.77(1H, d, J=5.5), 5.34(1H, d, J=12.2), 5.42(1H, d, J=12.2), 7.29–7.38(5H, m), 7.43–7.48(1H, m), 7.56(2H, d, J=8.6) |
| 480 | 2.84(3H, d, J=4.9), 3.34(3H, s), 5.13(1H, s), 5.23(1H, d, J=12.2), 5.65(1H, d, J=12.2), 6.80(1H, brs), 7.27–7.40(6H, m), 7.41–7.48(1H, m), 7.53–7.58(2H, m), 8.10(1H, s) |
| 481 | 2.80(3H, d, J=4.9), 4.66(1H, brs), 5.25(1H, d, J=12.2), 5.41(1H, d, J=12.2), 5.42(1H, s), 6.60(1H, brs), 7.32–7.57(9H, m), 8.06(1H, s) |
| 482 | 3.40(3H, s), 3.72(3H, s), 5.25(1H, s), 5.25(1H, d, J=12.2), 5.50(1H, d, J=12.2), 7.31–7.65(9H, m), 8.12(1H, s) |
| 483 | 3.74(1H, 4, J=5.5), 3.75(3H, s), 5.31(1H, d, J=12.2), 5.42(1H, d, J=12.2), 5.59(1H, d, J=5.5), 7.34–7.49(6H, m), 7.41–7.50(1H, m), 7.52–7.66(2H, m), 8.11(1H, s) |
| 484 | 144–145° C. |
| 486 | 123–125° C. |
| 487 | 111.5–112.5° C. |
| 488 | 2.26(3H, s), 3.39(3H,s), 3.71(3H, s), 5.27(1H, s), 5.28(1H, d, J=12.2), 5.52(1H, d, J=12.2), 7.32–7.40(5H, m), 7.43–7.56(2H, m), 7.61–7.69(2H, m) |
| 489 | 2.24(3H, s), 2.65(3H, d, J=4.9), 4.83(1H, brs), 5.23(1H, d, J=12.2), 5.43(1H, d, J=12.2), 5.45(1H, s), 6.59(1H, brs), 7.31–7.40(6H, m), 7.44–7.48(1H, m), 7.52–7.58(2H, m) |
| 490 | 93–94° C. |
| 491 | 2.26(3H, s), 3.75(3H, s), 5.35(1H, d, J=12.2), 5.42(1H, d, J=12.2), 5.59(1H, s), 7.32–7.41(6H, m), 7.45–7.50(1H, m), 7.58–7.65(2H, m) |
| 492 | 99–101.5° C. |
| 493 | 141.5–142.5° C. |
| 494 | 74–74.5° C. |
| 495 | 2.21(3H, s), 2.68(3H, d, J=4.9), 3.82(3H, s), 4.95(1H, brs), 5.20(1H, d, J=12.2) 5.40(1H, d, J=12.2), 5.45(1H, s), 6.64(1H, brs), 6.89(2H, d, J=8.5), 7.31–7.48(4H, m), 7.50(2H, d, J=8.5) |
| 496 | 2.20(3H, s), 3.82(3H,s), 5.21(1H, d, J=12.2), 5.39(1H, brs), 5.43 (1H, d, J=12.2), 5.48(1H, s), 6.79(1H, brs), 6.88(2H, d, J=8.5), 7.28–7.46(4H, m), 7.49(2H, d, J=8.5) |
| 497 | 72.5–73.5° C. |
| 498 | 2.22(3H, s), 2.35(3H, s), 2.81(3H, d, J=5.5), 3.33(3H, s), 5.15(1H, s) 5.26(1H, d, J=12.2), 5.63(1H, d, J=12.2), 6.77(1H, brs), 7.15(2H, d, J=7.9), 7.28–7.48(4H, m), 7.52(2H, d, J=7.9) |
| 499 | 122–123° C. |
| 500 | 2.23(3H, s), 2.36(3H, s), 3.39(3H, s), 3.71(3H, s), 5.26(1H, d, J=12.2), 5.27(1H, s), 5.38(1H, d, J=12.2), 7.16(2H, d, J=7.9), 7.32–7.51(4H, m), 7.54(2H, d, J=7.9) |
| 501 | 2.22(3H, s), 2.35(3H, s), 2.66(3H, d, J=4.9), 4.91(1H, brs), 5.21 (1H, d, J=12.2), 5.41(1H, d, J=12.2), 5.45(1H, s), 6.62(1H, brs), 7.17(2H, d, J=7.9), 7.31–7.47(6H, m) |
| 502 | 105–106° C. |
| 504 | 2.22(3H, s), 2.83(3H, d, J=4.9), 3.32(3H, s), 5.11(1H, s), 5.26(1H, d, J=12.2), 5.63(1H, d, J=12.2), 6.78(1H, brs), 7.23–7.46(7H, m) |
| 505 | 118–120.5° C. |
| 506 | 2.22(3H, s), 3.38(3H, s), 3.71(3H, s), 5.22(1H, s), 5.26(1H, d, J=12.2), 5.50(1H, d, J=12.2), 7.24–7.65(7H, m) |
| 507 | 2.21(3H, s), 2.66(3H, d, J=4.9), 5.23 (1H, d, J=12.2), 5.39 (1H, d, J=12.2), 5.39(1H, s), 6.55(1H, brs), 7.15–7.47(7H, m) |
| 510 | 2.23(3H, s), 2.56(3H, d, J=4.9), 4.72(1H, d, J=3.1), 5.22(1H, d, J=12.2), 5.41(1H, s), 5.42(1H, d, J=12.2), 6.58–6.68(1H, m), 7.19–7.49 (8H, m) |
| 513 | 2.24(3H, s), 2.81(3H, d, J=4.9), 3.32(3H, s), 5.12(1H, s), 5.28(1H, d, J=12.2), 5.62(1H, d, J=12.2), 6.78(1H, brs), 7.21–7.48(8H, m) |
| 515 | 2.25(3H, s), 3.39(3H, s), 3.71(3H, s), 5.24(1H, s), 5.27(1H, d, J=12.8), 5.51(1H, d, J=12.2), 7.22–7.65(8H, m) |
| 516 | 2.22(3H, s), 2.72(3H, d, J=4.9), 4.62(1H, brs), 5.26(1H, d, J=12.2), 5.43(1H, s), 6.48(1H, brs), 7.27–7.65(8H, m) |
| 517 | 87–88° C. |
| 518 | 2.23(3H, s), 3.40(3H, s), 3.72(3H, s), 5.24(1H, s), 5.28(1H, d, J=12.2), 5.52(1H, d, J=12.2), 7.25–7.66(8H, m) |
| 520 | 2.21(3H, s), 2.80(3H, d, J=4.9), 3.31(3H, s), 5.09(1H, s), 5.25(1H, d, J=12.2), 5.59(1H, d, J=12.2), 6.76(1H, brs), 7.29–7.57(7H, m), 7.67(1H, d, J=7.3) |
| 523 | 2.27(3H, s), 2.83(3H, d, J=4.9), 3.33(3H, s), 5.13(1H, s), 5.29(1H, d, J=12.2), 5.70(1H, d, J=12.2), 6.78(1H, brs), 7.29–7.50(5H, m), 7.60(1H, d, J=7.9), 7.82(1H, d, J=7.9), 7.89(1H, s) |
| 526 | 2.26(3H, s), 2.84(3H, d, J=4.9), 3.33(3H, s), 5.12(1H, s), 5.29(1H, d, J=12.2), 5.70(1H, d, J=12.2), 6.80(1H, brs), 7.29–7.48(4H, m), 7.60(2H, d, J=7.9), 7.75(2H, d, J=7.9) |
| 527 | 2.27(3H, s), 3.40(3H, s), 3.72(3H, s), 5.24(1H, s), 5.30(1H, d, J=12.2), 5.54(1H, d, J=12.2), 7.32–7.57(4H, m), 7.61(2H, d, J=8.5), 7.76(2H, d, J=8.5) |
| 529 | 2.28(3H, s), 2.84(3H, d, J=4.9), 3.33(3H, s), 5.11(1H, s), 5.32(1H, d, J=12.8), 5.74(1H, d, J=12.8), 6.84(1H, brs), 7.29–7.41(3H, m), 7.42–7.47(1H, m), 7.80(2H, d, J=8.6), 8.18(2H, d, J=8.6) |
| 532 | 2.19(3H, s), 2.26(3H, s), 2.76(3H, d, J=4.9), 3.31(3H, s), 5.13(1H, s), 5.26(1H, d, J=12.2), 5.57(1H, d, J=12.2), 6.75(1H, brs), 7.10–7.28(4H, m), 7.29–7.38(3H, m), 7.42–7.47(1H, m) |
| 535 | 2.23((3H, s), 2.36(3H, s), 2.82(3FH, d, J=4.9), 3.32(3H, s), 5.14(1H, s), 5.27(1H, d, J=12.2), 5.63(1H, d, J=12.2), 6.76(1H, brs), 7.10–7.45(8H, m) |
| 541 | 1.10(3H, t, J=7.3), 2.74(2H, q, J=7.3), 2.83(3H, d, J=4.9), 3.32(3H, s), 5.12(1H, s), 5.25(1H, d, J=12.2), 5.65(1H, d, J=12.2), 6.78(1H, brs), 7.32(2H, d, J=8.5), 7.35–7.53(4H, m), 7.56(2H, d, J=8.5) |
| 542 | 1.11(3H, t, J=7.9), 2.75(2H, q, J=7.9), 3.39(3H, s), 3.71(3H, s), 5.24(1H, s), 5.25(1H, d, J=12.2), 5.50(1H, d, J=12.2), 7.33(2H, d, J=8.5), 7.36–7.65(4H, m), 7.57(2H, d, J=8.5) |
| 544 | 1.10(3H, t, J=7.6), 2.73(2H, q, J=7.6), |

| Comp. No. | Physical data |
|---|---|
|  | 3.32(3H, s), 3.81(3H, s), 5.14 (1H, s), 5.24(1H, d, J=12.2), 5.61(1H, d, J=12.2), 6.75(1H, brs), 6.84(2H, d, J=8.6), 7.30–7.40(3H, m), 7.45–7.50(1H, m), 7.56(2H, d, J=8.6) |
| 547 | 1.86(6H, s), 2.82(3H, d, J=4.9), 3.33(3H, s), 5.09(1H, s), 5.11(1H d J=12.2), 5.43(1H, d, J=12.2), 6.72(1H, brs), 7.30–7.40(4H, m) |
| 548 | 1.87(6H, s), 3.38(3H, s), 3.70(3H, s), 5.08(1H, d, J=12.2), 5.22(1H, s), 5.32(1H, d, J=12.2), 7.31–7.39(3H, m), 7.46–7.48(1H, m) |
| 550 | 0.89(3H, t, J=7.3), 1.23–1.35(2H, m), 1.40–1.50(2H, m), 1.83(3H, s), 2.14 & 2.35 (2H in total, each t, J=7.3), 2.83(3H, d, J=4.9), 3.33(3H, s), 5.08(1H, s), 5.09 & 5.11 (1H in total, each d, J=12.2), 5.42 & 5.43 (1H in total, each d, J=12.2), 6.80(1H, brs), 7.31–7.39(4H, m) |
| 551 | 0.87–0.92(3H, m), 1.25–1.40(2H, m), 1.45–1.55(2H, m), 1.85 & 1.86 (3H in total, each s), 2.16 & 2.35(2H in total, each t, J=7.3), 3.37(3H, s), 3.70(3H, s), 5.07 & 5.10(1H in total, each d, J=12.2), 5.21(1H, s), 5.33 & 5.34(1H in total, each d, J=12.2), 7.31–7.39(3H, m), 7.42–7.44(1H, m) |
| 553 | 2.19(3H, s), 2.78(3H, d, J=4.9), 3.32(3H, s), 3.80(3H, s), 5.14(1H, s) 5.25(1H, d, J=12.2), 5.57(1H, d, J=12.2), 6.76(1H, brs), 6.87–6.95 (2H, m), 7.25–7.40(5H, m), 7.45–7.50(1H, m) |
| 556 | 2.23(3H, s), 2.82(3H, d, J=4.9), 3.32(3H, s), 3.82(3H, s), 5.13(1H, s) 5.27(1H, d, J=12.2), 5.65(1H, d, J=12.2), 6.85(1H, brs), 6.90–6.92 (1H, m), 7.20–7.26(3H, m), 7.30–7.45(3H, m), 7.48–7.52(1H, m) |
| 559 | 2.22(3H, s), 2.26(3H, s), 2.27(3H, s), 2.81(3H, d, J=4.9), 3.33(3H, s) 5.14(1H, s), 5.27(1H, d, J=12.2), 5.63(1H, d, J=12.2), 6.74–6.75(1H, m), 7.10(1H, d, J=7.9), 7.28–7.49(6H, m) |
| 562 | 2.21(3H, s), 2.84(3H, d, J=4.9), 3.33(3H, s), 5.11(1H, s), 5.27(1H, d, J=12.2), 5.68(1H, d, J=12.2), 6.78–6.79(1H, m), 7.28–7.49(6H, m), 7.73(1H, brs) |
| 571 | 1.93(3H, s), 2.35(3H, s), 2.85(3H, d, J=4.9), 3.32(3H, s), 5.50(1H, s), 5.30(1H, d, J=12.2), 5.79(1H, d, J=12.2), 6.82(1H, brs), 7.29–7.43(4H, m) |
| 572 | 1.94(3H, s), 2.36(3H, s), 3.39(3H, s), 3.72(3H, s), 5.15(1H, s), 5.34 (1H, d, J=12.2), 5.56(1H, d, J=12.2), 7.33–7.65(4H, m) |
| 575 | 2.16(3H, s), 3.33(3H, s), 3.67(3H, s), 5.15(1H, s), 5.31(1H, d, J= 12.2), 5.55(1H, d, J=12.2), 7.33–7.55(7H, m), 7.79–7.83(2H, m) |
| 577 | 2.28(3H, s), 2.83(3H, d, J=4.9), 3.34(3H, s), 5.16(1H, s), 5.30(1H, d J=12.2), 5.68(1H, d, J=12.2), 6.77(1H, brs), 7.31(7H, m), 7.57–7.62 (4H, m), 7.71(2H, d, J=8.5) |
| 580 | 2.38(3H, s), 2.75(3H, d, J=4.9), 3.30(3H, S0, 5.18(1H, s), 5.34(1H, d, J=12.2), 5.68(1H, d, J=12.2), 6.75(1H, brs), 7.33–7.55(8H, m), 7.81–7.93(3H, m) |
| 581 | 2.38(3H, s), 3.39(3H, s), 3.69(3H, s), 5.31(1H, s), 5.32(1H, d, J= 12.2), 5.56(1H, d, J=12.2), 7.36–7.60(8H, m), 7.83–7.95(3H, m) |
| 583 | 2.17(3H, s), 2.83(3H, d, J=4.9), 3.34(3H, s), 5.10(1H, s), 5.29(1H, d, J=12.2), 5.62(1H, d, J=12.2), 6.43(1H, dd, J=3.7, 1.8), 6.62(1H, d, J=3.7), 6.79(1H, brs), 7.28–7.47(5H, m) |
| 584 | 2.18(3H, s), 3.40(3H, s), 3.71(3H, s), 5.23(1H, s), 5.28(1H, d, J= 12.2), 5.52(1H, d, J=12.2), 6.44(1H, dd, J=3.7, 1.8), 6.64(1H, 4, J= 3.7), 7.32–7.55(5H, m) |
| 586 | 2.25(3H, s), 2.84(3H, d, J=4.9), 3.35(3H, s), 5.13(1H, s), 5.23(1H, d, J=12.2), 5.62(1H, d, J=12.2), 6.79(1H, brs), 6.99(1H, dd, J=4.9, 3.7), 6.98–7.47(6H, m) |
| 587 | 2.26(3H, s), 3.40(3H, s), 3.71(3H, s), 5.24(1H, d, J=12.2), 5.25(1H, s), 5.47(1H, d, J=12.2), 7.00(1H, dd, J=5.5, 3.7), 7.21–7.53(6H, m) |
| 589 | 2.35(3H, s), 2.84(3H, d, J=5.5), 3.33(3H, s), 5.14(1H, s), 5.30(1H, d, J=12.2), 5.73(1H, d, J=12.2), 6.80(1H, brs), 7.21–7.49(5H, m), 7.65(1H, dt, J=1.8, 7.9), 7.90(1H, d, J=7.9), 8.56–8.59(1H, m) |
| 590 | 2.36(3H, s), 3.40(3H, s), 3.71(3H, s), 5.25(1H, s), 5.31(1H, d, J= 12.2), 5.55(1H, d, J=12.2), 7.22–7.56(5H, m), 7.65(1H, dt, J=1.8, 7.9), 7.89(1H, d, J=7.9), 8.59(1H, dd, J=4.9, 1.8) |
| 592 | 81–83° C. |
| 593 | 2.33(3H, s), 3.41(3H, s), 3.73(3H, s), 5.24(1H, s), 5.35(1H, d, J= 12.2), 5.58(1H, d, J=12.2), 7.32–7.56(4H, m), 8.49–8.53(2H, m), 9.15(1H, d, J=1.2) |
| 603 | 2.23(3H, s), 3.25(3H, d, J=4.9), 3.33(3H, s), 5.29(1H, d, J=12.2), 5.51(1H, s), 5.80(1H, d, J=12.2), 7.25–7.36(5H, m), 7.42–7.47(1H, m), 7.58(2H, d, J=9.2), 8.77(1H, s) |
| 606 | 105–107° C. |
| 609 | 94.5–95.5° C. |
| 610 | 2.27(3H, s), 3.26(3H, d, J=4.9), 3.33(3H, s), 5.32(1H, s), 5.32(1H, d, J=12.2), 5.51(1H, s), 5.84(1H, d, J=12.2), 7.27–7.48(4H, m), 7.60(2H, d, J=7.9), 7.75(2H, d, J=7.9) |
| 616 | 1.10(3H, t, J=7.6), 2.34(3H, s), 2.76(2H, q, J=7.6), 2.81(3H, d, J= 4.9), 3.32(3H, s), 5.14(1H, s), 5.26(1H, d, J=12.2), 5.63(1H, d, J= 12.2), 6.76(1H, brs), 7.14(2H, d, J=7.8), 7.30–7.40(3H, m), 7.45–7.50(1H, m), 7.51(2H, d, J=7.8) |
| 627 | 1.55–1.68(6H, m), 2.19(2H, t, J=6.1), 2.44–2.49(2H, m), 2.83(3H, d, J=4.9), 3.33(3H, s), 5.09(1H, s), 5.10(1H, d, J=12.2), 5.42(1H, d, J=12.2), 6.75(1H, brs), 7.28–7.42(4H, m) |
| 628 | 1.55–1.69(6H, m), 2.08(2H, t, d=6.1), 2.40–2.52(2H, m), 3.38(3H, s), 3.70(3H, s), 5.07(1H, d, J=12.2), 5.22(1H, s), 5.33(1H, d, J=12.2), 7.28–7.62(4H, m) |
| 629 | 137.5–138.5° C. |
| 630 | 2.88–2.93(2H, m), 3.01–3.05(2H, m), 3.41(3H, s), 3.72(3H, s), 5, 26 (1H, d, J=12.2), 5.30(1H, s), 5.49(1H, d, J=12.2), 7.24–7.37(5H, m), 7.45–7.54(2H, m), 7.69(2H, d, J=7.3) |
| 631 | 1.20(3H, t, J=7.3), 2.23(3H, s), 3.39(3H, s), 4.14–4.22(2H, m), 5.22 (1H, s), 5.27(1H, d, J=12.2), 5.52(1H, d, J=12.2), 7.30–7.40(4H, m), 7.41–7.43(1H, m), 7.51–7.56(1H, m), |

-continued

| Comp. No. | Physical data |
|---|---|
| | 7.58(2H, d, J=8.6) |
| 632 | 1.16(3H, t, J=7.3), 2.22(3H, s), 3.28–3.32(2H, m), 3.32(3H, s), 5.10 (1H, s), 5.25(1H, d, J=12.2), 5.66(1H, d, J=12.2), 6.72(1H, brs), 7.29–7.38(5H, m), 7.43–7.46(1H, m), 7.58(2H, d, J=8.6) |
| 633 | 1.22–1.28(3H, m), 2.22(3H, s), 3.45–3.65(2H, m), 3.70(3H, s), 5.27 (1H, d, J=12.2), 5.32(1H, s), 5.50(1H, d, J=12.2), 7.29–7.38(4H, m), 7.41–7.43(1H, m), 7.53–7.55(1H, m), 7.57(2H, d, J=8.6) |
| 634 | 1.23(3H, t, J=7.3), 2.21(3H, s), 2.83(3H, d, J=4.9), 3.45(2H, q, J=7.3), 5.21(1H, s), 5.25(1H, d, J=12.2), 5.67(1H, d, J=12.2), 6.80(1H, brs), 7.29–7.32(4H, m), 7.37–7.42(2H, m), 7.57(2H, d, J=8.6) |
| 635 | 0.87(3H, t, J=7.3), 1.29–1.35(2H, m), 1.53–1.58(2H, m), 2.21(3H, s), 2.83(3H, d, J=4.9), 3.40(2H, t, J=7.3), 5.19(1H, s), 5.25(1H, d, J=12.2), 5.68(1H, d, J=12.2), 6.80(1H, brs), 7.29–7.43(6H, m), 7.57 (2H, d, J=8.6) |
| 636 | 0.87(3H, t, J=7.3), 1.23–1.45(2H, m), 1.56–1.63(2H, m), 2.22(3H, s), 3.39–3.58(2H, m), 3.69(3H, s), 5.27(1H, d, J=12.2), 5.30(1H, s), 5.49(1H, d, J=12.2), 7.29–7.39(4H, m), 7.41–7.43(1H, m), 7.52–7.59 (3H, m) |
| 637 | 102–103° C. |
| 638 | 2.20(3H, s), 2.83(3H, s), 3.00(3H, s), 3.46(3H, s), 5.25(1H, d, J= 12.2), 5.38(1H, s), 5.45(1H, d, J=12.2), 7.30–7.35(5H, m), 7.44–7.47 (1H, m), 7.58(2H, d, J=8.6) |
| 639 | 2.15(3H, s), 2.22(3H, s), 2.62(3H, d, J=4.9), 5.33(1H, d, J=12.2), 5.52(1H, d, J=12.2), 6.22(1H, brs), 6.47(1H, s), 7.31(2H, d, J=8.6), 7.34–7.39(2H, m), 7.42–7.53(2H, m), 7.56(2H, d, J=8.6) |
| 671 | 1.06(3H, t, J=7.3), 1.84(3H, s), 2.16 & 2.35(2H in total, each q, J=7.3), 2.82(3H, d, J=4.9), 3.33(3H, s), 5.09 & 5.11(1H in total, each d, J=12.2), 5.11(1H, s), 5.40 & 5.42(1H in total, each d, J=12.2), 6.80(1H, brs), 7.30–7.39(4H, m) |
| 672 | 1.04–1.10(3H, m), 1.84 & 1.85(3H in total, each s), 2.16 & 2.34(2H in total, each q, J=7.3), 3.38(3H, s), 3.70(3H, s), 5.07 & 5.12(1H in total, each d, J=12.2), 5.27(1H, s), 5.34 & 5.36(1H in total, each d, J=12.2), 7.30–7.38(3H, m), 7.42–7.45(1H, m) |
| 678 | 2.20(3H, s), 2.83(3H, d, J=4.9), 3.33(3H, s), 3.91(3H, s), 5.13(1H, s), 5.25(1H, d, J=12.2), 5.65(1H, d, J=12.2), 6.77(1H, brs), 6.89(1H, d, J=8.5), 7.29–7.46(4H, m), 7.50(1H, dd, J=8.5, 2.4), 7.69(1H, d, J=2.4) |
| 680 | 2.21(3H, s), 2.38(3H, s), 2.83(3H, d, J=4.9), 3.33(3H, s), 5.12(1H, s) 5.27(1H, d, J=12.2), 5.65(1H, d, J=12.2), 6.78(1H, brs), 7.29–7.51 (7H, m) |
| 682 | 2.23(3H, s), 2.81(3H, d, J=4.9), 3.32(3H, s), 5.12(1H, s), 5.27(1H, d, J=12.2), 5.66(1H, d, J=12.2), 6.51(1H, t, J=73.8), 6.81(1H, brs), 7.08(2H, d, J=8.6), 7.30–7.39(3H, m), 7.42–7.47(1H, m), 7.63(2H, d, |

| Comp. No. | Physical data |
|---|---|
| | J=8.6) |
| 684 | 2.22(3H, s), 2.82(3H, d, J=4.9), 3.33(3H, s), 3.89(3H, s), 3.91(3H, s), 5.14(1H, s), 5.26(1H, d, J=12.2), 5.65(1H, d, J=12.2), 6.76–6.78(1H, m), 6.83(1H, d, J=8.5), 7.13(1H, dd, J=8.5, 2.4), 7.29(1H, d, J=2.4), 7.29–7.49(4H, m) |
| 686 | 2.18(3H, s), 2.23(3H, s), 2.30(3H, s), 2.78(3H, d, J=4.9), 3.32(3H, s), 5.13(1H, s), 5.25(1H, d, J=12.2), 5.58(1H, d, J=12.2), 6.75(1H, brs), 6.97–7.47(7H, m) |
| 688 | 2.22(3H, s), 2.78(3H, d, J=4.9), 3.31(3H, s), 5.14(1H, s), 5.27(1H, d, J=12.2), 5.66(1H, d, J=12.2), 6.80(1H, brs), 6.93–7.01(4H, m), 7.10(1H, t, J=7.3), 7.28–7.39(5H, m), 7.41–7.67(1H, m), 7.60(2H, d, J=9.2) |
| 690 | 2.23(3H, d, J=3.1), 2.81(3H, d, J=4.9), 3.33(3H, s), 3.80(3H, s), 5.13(1H, s), 5.25(1H, d, J=12.2), 5.62(1H, d, J=12.2), 6.60(1H, dd, J=12.8, 2.4), 6.66(1H, dd, J=8.5, 2.4), 7.29–7.47(5H, m) |
| 692 | 2.20(3H, s), 2.83(3H, d, J=4.9), 3.33(3H, s), 3.90(3H, s), 5.13(1H, s), 5.25(1H, d, J=12.2), 5.64(1H, d, J=12.2), 6.77–6.79(1H, m), 6.92(1H, t, J=8.5), 7.29–7.49(6H, m) |
| 698 | 2.21(3H, s), 2.82(3H, d, J=4.9), 3.32(3H, s), 5.12(1H, s), 5.26(1H, d, J=12.2), 5.66(1H, d, J=12.2), 6.75(1H, brs), 7.28–7.40(3H, m), 7.42–7.55(5H, m) |
| 701 | 2.22(3H, s), 2.82(3H, d, J=4.9), 3.32(3H, s), 5.13(1H, s), 5.25(1H, d, J=12.2), 5.65(1H, d, J=12.2), 6.73(1H, brs), 7.00–7.05(2H, m), 7.27–7.36(3H, m), 7.43–7.45(1H, m), 7.58–7.62(2H, m) |
| 702 | 1.41(3H, t, J=7.3), 2.21(3H, s), 2.81(3H, d, J=4.9), 3.33(3H, s), 4.05(2H, q, J=7.3), 5.15(1H, s), 5.25(1H, d, J=12.2), 5.62(1H, d, J=12.2), 6.75(1H, brs), 6.86(2H, d, J=8.5), 7.30–7.48(4H, m), 7.56(2H, d, J=8.5) |
| 704 | 0.97(3H, t, J=7.3), 1.49(2H, sextet, J=7.3), 1.77(2H, quintet, J=7.3), 2.21(3H, s), 2.81(3H, d, J=4.9), 3.33(3H, s), 3.97(2H, t, J=7.3), 5.15(1H, s), 5.25(1H, d, J=12.2), 5.62(1H, d, J=12.2), 6.75(1H, brs), 6.86(2H, d, J=8.5), 7.28–7.48(4H, m), 7.56(2H, d, J=8.5) |
| 707 | 1.31(9H, s), 2.23(3H, s), 2.80(3H, d, J=4.9), 3.32(3H, s), 5.14(1H, s), 5.26(1H, d, J=12.2), 5.63(1H, d, J=12.2), 6.75(1H, brs), 7.30–7.38(5H, m), 7.42–7.47(1H, m), 7.56(2H, d, J=8.6) |
| 710 | 1.22(3H, t, J=7.6), 2.22(3H, s), 2.65(2H, q, J=7.6), 2.81(3H, d, J=4.9), 3.32(3H, s), 5.14(1H, s), 5.26(1H, d, J=12.2), 5.63(1H, d, J=12.2), 6.75(1H, brs), 7.17(2H, d, J=8.6), 7.30–7.38(3H, m), 7.44–7.47 (1H, m), 7.54(2H, d, J=8.6) |
| 717 | 1.15(3H, t, J=7.3), 2.22(3H, s), 2.34(3H, s), 3.21–3.40(2H, m), 3.32 (3H, s), 5.13(1H, s), 5.26(1H, d, J=12.2), 5.65(1H, d, J=12.2), 6.77 (1H, brs), 7.14(2H, d, J=8.5), 7.28–7.39(3H, m), 7.44–7.48(1H, m), 7.52(2H, d, J=8.5) |
| 718 | 1.19(3H, t, J=7.0), 2.21(3H, s), 2.34(3H, s), 2.82(3H, d, J=4.9), 3.47 |

| Comp. No. | Physical data |
|---|---|
| | (2H, q, J=7.0), 5.23(1H, s), 5.26(1H, d, J=12.2), 5.67(1H, d, J=12.2) 6.85(1H, brs), 7.20–7.53(8H, m) |
| 721 | 1.15(3H, t, J=7.3), 2.22(3H, s), 2.34(3H, s), 3.22–3.36(2H, m), 3.32 (3H, s), 3.81(3H, s), 5.13(1H, s), 5.25(1H, d, J=12.2), 5.63(1H, d, J=12.2), 6.76(1H, brs), 6.86(2H, d, J=9.2), 7.29–7.38(3H, m), 7.43–7.48(1H, m), 7.58(2H, d, J=9.2) |
| 722 | 1.18(3H, t, J=7.0), 2.20(3H, s), 2.82(3H, d, J=4.9), 3.48(2H, q, J=7.0), 3.81(3H, s), 5.23(1H, s), 5.25(1H, d, J=12.2), 5.64(1H, d, J=12.2), 6.80(1H, brs), 6.87(2H, d, J=8.3), 7.29–7.46(4H, m), 7.58(2H, d, J=8.3) |
| 725 | 1.16(3H, t, J=7.3), 2.26(3H, s), 3.24–3.37(2H, m), 3.33(3H, s), 5.11(1H, s), 5.29(1H, d, J=12.2), 5.71(1H, d, J=12.2), 6.78(1H, brs), 7.29–7.40(3H, m), 7.44–7.47(1H, m), 7.59(2H, d, J=8.5), 7.75(2H, d, J=8.5) |
| 726 | 88~90° C. |
| 733 | 0.93(3H, t, J=7.3), 1.54(2H, sextet, J=7.3), 2.72(2H, t, J=7.3), 3.39 (3H, s), 3.71(3H, s), 5.24(1H, s), 5.25(1H, d, J=12.2), 5.49(1H, d, J=12.2), 7.29–7.53(4H, m), 7.32(2H, d, J=8.5), 7.56(2H, d, J=8.5) |
| 734 | 2.34(3H, s), 3.34(3H, s), 3.67(3H, s), 5.29(1H, s), 5.30(1H, d, J=12.2), 5.58(1H, d, J=12.2), 7.70(1H, dd, J=5.5, 3.7), 7.32–7.56(6H, m) |
| 735 | 2.32(3H, s), 2.79(3H, d, J=4.9), 3.29(3H, s), 5.18(1H, s), 5.31(1H, d, J=12.2), 5.72(1H, d, J=12.2), 6.74(1H, brs), 7.05–7.08(1H, m), 7.27–7.52(6H, m) |
| 736 | 0.92(3H, t, J=7.3), 1.53(2H, sextet, J=7.3), 2.71(2H, t, J=7.3), 2.83 (3H, d, J=4.9), 3.32(3H, s), 5.12(1H, s), 5.25(1H, d, J=12.2), 5.65 (1H, d, J=12.2), 6.75–6.78(1H, m), 7.28–7.53(4H, m), 7.31(2H, d, J=8.5), 7.55(2H, d, J=8.5) |
| 737 | 3.29(3H, s), 3.39(3H,s), 3.71(3H, s), 4.62(2H, s), 5.22(1H, s), 5.28 (1H, d, J=12.2), 5.53(1H, d, J=12.2), 7.30–7.36(5H, m), 7.39–7.44 (1H, m), 7.45–7.50(1H, m), 7.62–7.67(2H, m) |
| 738 | 2.81(3H, d, J=4.9), 3.29(3H, s), 3.32(3H, s), 4.62(2H, s), 5.11(1H, s), 5.27(1H, d, J=12.2), 5.57(1H, d, J=12.2), 6.78(1H, brs), 7.30–7.45(6H, m), 7.56–7.59(1H, m), 7.65–7.67(2H, m) |
| 739 | 1.10(3H, t, J=7.3), 1.16(3H, t, J=7.3), 2.74(2H, q, J=7.3), 3.22–3.35 (2H, m), 3.32(3H, s), 5.10(1H, s), 5.26(1H, d, J=12.2), 5.66(1H, d, J=12.2), 6.78(1H, brs), 7.27–7.39(3H, m), 7.31(2H, d, J=8.6), 7.42–7.47(1H, m), 7.56(2H, d, J=8.6) |
| 740 | 1.11(3H, t, J=7.3), 2.76(2H, q, J=7.3), 2.82(3H, d, J=4.9), 3.32(3H, s), 5.12(1H, s), 5.25(1H, d, J=12.8), 5.65(1H, d, J=12.8), 6.51(1H, t, J=73.9), 6.77(1H, brs), 7.09(2H, d, J=8.6), 7.28–7.39(3H, m), 7.40–7.48(1H, m), 7.63(2H, d, J=8.6) |
| 741 | 2.51–2.89(7H, m), 3.31 & 3.35(3H in total, each s), 3.50 & 3.79(2H in total, each s), 5.08–5.20(2H, m), 5.44–5.55(1H, m), 6.75(1H, brs), 7.09–7.20(4H, m), 7.25–7.45(4H, m) |
| 756 | 0.89(3H, t, J=7.3), 1.56–1.63(2H, m), 2.21(3H, s), 2.84(3H, d, J=4.9), 3.36(2H, t, J=7.3), 5.20(1H, s), 5.25(1H, d, J=12.2), 5.69(1H, d, J=12.2), 6.85(1H, brs), 7.29–7.44(6H, m), 7.58(2H, dd, J=8.6, 1.8) |
| 757 | 0.88(3H, t, J=1.3), 1.56–1.63(2H, m), 2.21(3H, s), 2.34(3H, s), 2.83 (3H, d, J=4.9), 3.37(2H, t, J=7.3), 5.22(1H, s), 5.24(1H, d, J=12.2), 5.67(1H, d, J=12.2), 6.80(1H, brs), 7.14(2H, d, J=8.0), 7.29–7.43(4H, m), 7.52(2H, d, J=8.0) |
| 758 | 0.88(3H, t, J=7.3), 1.56–1.64(2H, m), 2.21(3H, s), 2.83(3H, d, J=4.9), 3.37(2H, t, J=7.3), 3.81(3H, s), 5.22(1H, s), 5.24(1H, d, J=12.2), 5.67(1H, d, J=12.2), 6.80(1H, brs), 6.86(2H, d, J=8.3), 7.29–7.46(4H, m), 7.56(2H, d, J=8.3) |
| 759 | 0.88(3H, t, J=7.3), 1.56–1.63(2H, m), 2.25(3H, s), 2.84(3H, d, J=4.9), 3.36(2H, t, J=7.3), 5.20(1H, s), 5.28(1H, d, J=12.2), 5.73(1H, d, J=12.2), 6.85(1H, brs), 7.29–7.46(4H, m), 7.59(2H, d, J=8.0), 7.73(2H, d, J=8.0) |
| 773 | 2.18(3H, s), 2.21(3H, s), 2.30(3H, s), 2.78(3H, d, J=4.9), 3.32(3H, s), 5.13(1H, s), 5.26(1H, d, J=12.2), 5.58(1H, d, J=12.2), 6.76(1H, brs), 7.00–7.08(3H, m), 7.30–7.48(4H, m) |
| 777 | 2.22(3H, s), 2.32(6H, s), 2.81(3H, d, J=4.9), 3.33(3H, s), 5.14(1H, s) 5.28(1H, d, J=12.2), 5.64(1H, d, J=12.2), 6.77(1H, brs), 6.99(1H, s), 7.24–7.48(6H, m) |
| 781 | 2.21(3H, s), 2.22(3H, s), 2.81(3H, d, J=4.9), 3.33(3H, s), 3.83(3H, s) 5.14(1H, s), 5.26(1H, d, J=12.2), 5.62(1H, d, J=12.2), 6.75(1H, brs), 6.79(1H, d, J=8.5), 7.28–7.49(6H, m) |
| 785 | 2.35(3H, s), 2.80(3H, d, J=4.9), 3.33(3H, s), 5.17(1H, s), 5.33(1H, d, J=12.2), 5.73(1H, d, J=12.2), 6.79(1H, brs), 7.29–7.40(3H, m), 7.43–7.51(3H, m), 7.78–7.86(3H, m), 7.91(1H, dd, J=8.8, 1.8), 7.97(1H, s) |
| 813 | 2.05(3H, s), 2.81(3H, d, J=4.9), 3.34(3H, s), 5.15(1H, s), 5.30(1H, d, J=12.2), 5.68(1H, s, J=12.2), 6.75(1H, brs), 7.30–7.47(8H, m) |
| 819 | 2.02(3H, s), 2.37(3H, s), 2.78(3H, d, J=4.9), 3.35(3H, s), 5.16(1H, s) 5.30(1H, d, J=12.2), 5.63(1H, d, J=12.2), 6.73(1H, brs), 7.18–7.58(8H, m) |
| 824 | 2.06(3H, s), 2.82(3H, d, J=4.9), 3.34(3H, s), 5.15(1H, s), 5.31(1H, d, J=12.2), 5.71(1H, d, J=12.2), 6.75(1H, brs), 7.29–7.47(4H, m), 7.54 (2H, d, J=7.9), 7.67(2H, d, J=7.9) |
| 837 | 2.05(3H, s), 2.78(3H, d, J=4.9), 3.35(3H, s), 3.82(3H, s), 5.16(1H, s), 5.30(1H, d, J=12.2), 5.63(1H, d, J=12.2), 6.73(1H, brs), 6.92(2H, d, J=8.6), 7.27–7.48(6H, m) |
| 873 | 2.12(3H, s), 2.32(3H, s), 2.81(3H, d, J=4.9), 3.36(3H, s), 5.11(1H, s), 5.17(1H, d, J=12.2), 5.51(1H, d, J=12.2), 6.74(1H, brs), 7.26–7.42(4H, m) |
| 879 | 0.91(3H, t, J=7.3), 1.33(2H, sextet, J=7.3), 1.56(2H, quintet, J=7.3), 2.31(3H, s), 2.40(2H, t, J=7.3), 2.81(3H, d, J=4.9), 3.36(3H, s), 5.10 (1H, s), 5.18(1H, d, J=12.2), 5.50(1H, d, J=12.2), 6.73(1H, brs), 7.26– |

| Comp. No. | Physical data |
|---|---|
|  | 7.42(4H, m) |
| 882 | 134–135° C. |
| 883 | 1.18(6H, d, J=6.7), 1.95(3H, s), 2.27–2.36(2H, m), 2.83(3H, d, J=4.9), 3.34(3H, s), 3.45–3.49(2H, m), 3.59–3.67(2H, m), 5.00(1H, d, J= 12.2), 5.09(1H, s), 5.30(1H, d, J=12.2), 6.75(1H, brs), 7.28–7.43(4H, m) |
| 891 | 0.88(3H, t, J=7.3), 1.18(6H, d, J=6.7), 1.26–1.44(4H, m), 2.28–2.44 (4H, m), 2.83(3H, d, J=4.9), 3.33(3H, s), 3.42–3.46(2H, m), 3.58– 3.64(2H, m), 4.98(1H, d, J=12.2), 5.09(1H, s), 5.29(1H, d, J=12.2), 6.75 (1H, brs), 7.27–7.43(4H, m) |
| 898 | 2.76(3H, d, J=4.9), 2.99(4H, t, J=4.3), 3.04(3H, s), 3.68(4H, t, J=4.3), 4.90(1H, s), 4.97(1H, d, J=12.2), 5.33(1H, d, J=12.2), 6.61(1H, brs), 7.20–7.43(8H, m) |
| 904 | 2.34(3H, s), 2.70(3H, d, J=4.9), 3.01(4H, t, J=4.9), 3.04(3H, s), 3.67 (4H, t, J=4.9), 4.91(1H, s), 4.99(1H, d, J=12.2), 5.28(1H, d, J=12.2), 6.51(1H, brs), 7.15–7.36(8H, m) |
| 905 | 1.12(6H, d, J=6.7), 2.29–2.39(2H, m), 2.35(3H, s), 2.69(3H, d, J= 4.9), 3.04(3H, s), 3.22–3.30(2H, m), 3.59–3.70(2H, m), 4.90(1H, s), 4.98(1H, d, J=12.2), 5.26(1H, d, J=12.2), 6.50(1H, brs), 7.14–7.39 (8H, m) |
| 906 | 130–131° C. |
| 907 | 1.13(6H, d, J=6.7), 2.32–2.42(2H, m), 2.77(3H, d, J=4.9), 2.98(3H, s), 3.15–3.23(2H, m), 3.59–3.71(2H, m), 4.86(1H, s), 4.96(1H, d, J=12.2), 5.34(1H, d, J=12.2), 6.64(1H, brs), 7.25–7.28(4H, m), 7.47(2H, d, J=7.9), 7.63(2H, d, J=7.9) |
| 910 | 2.71(3H, d, J=4.9), 3.01(4H, t, J=4.9), 3.05(3H, s), 3.68(4H, t, J=4.9), 3.80(3H, s), 4.93(1H, s), 5.00(1H, d, J=12.2), 5.29(1H, d, J=12.2), 6.53(1H, brs), 6.87(2H, d, J=8.5), 7.23–7.39(6H, m) |
| 911 | 1.12(3H, d, J=6.7), 1.13(3H, d, J=6.7), 2.28–2.38(2H, m), 2.70(3H, d J=4.9), 3.06(3H, s), 3.22–3.27(2H, m), 3.56–3.70(2H, m), 3.81.(3H, s), 4.92(1H, s), 5.00(1H, d, J=12.2), 5.28(1H, d, J=12.2), 6.52(1H, brs), 6.87(2H, d, J=9.2), 7.23–7.34(6H, m) |
| 941 | 2.21(3H, s), 2.36(3H, s), 2.85(3H, d, J=4.9), 3.36(3H, s), 5.05(1H, s), 5.34(1H, d, J=12), 5.64(1H, d, J=12), 6.82(1H, brs), 7.33–7.40(5H, m), 7.48–7.50(1H, m), 7.81(2H, d, J=8.8) |
| 982 | 0.72–0.74(2H, m), 1.00–1.05(2H, m), 1.61(1H, m), 2.82(3H, d, J=4.9), 3.54(3H, s), 4.26–4.31(1H, m), 4.55–4.60(1H, m), 5.07(1H, s), 6.85 (1H, brs), 6.84–6.88(2H, m), 7.30–7.41(6H, m) |
| 995 | 0.68–0.70(2H, m), 1.00–1.05(2H, m), 1.80–1.85(1H, m), 2.30(3H, s), 2.81(3H, d, J=4.9), 3.31(3H, s), 4.20(1H, d, J=13.0), 4.60(1H, d, J=13.0), 5.09(1H, s), 6.60(1H, brs), 6.75(2H, m), 7.00–7.20(2H, m), 7.30–7.55(4H, m) |
| 1017 | 2.33(3H, s), 2.68(3H, d, J=4.9), 3.30(3H, s), 4.59(2H, s), 4.67(1H, d, J=12.0), 4.91(1H, d, J=12.0), 5.01(1H, s), 6.70(1H, brs), 7.10– 7.20(2H, m), 7.29–7.41(6H, m) |
| 1030 | 2.82(3H, d, J=4.9), 3.35(3H, s), 5.10(1H, s), 5.44(1H, d, J=12.8), 5.74(1H, d, J=12.8), 6.83(1H, brs), |

| Comp. No. | Physical data |
|---|---|
|  | 7.30–7.58(7H, m), 8.07(2H, d, J=7.9) |

2-Oxo-2-[2-(tetrahydropyran-2-yloxymethyl)phenyl] acetic acid derivatives were synthesized by the method in Reference Examples 1 to 3 described below.

Reference Example 1

Synthesis of 1-bromo-2-(tetrahydropyran-2-yloxymethyl)benzene

Pyridinium p-toluenesulfonate (0.30 g) was added to a solution of 2-bromobenzylalcohol (25.00 g, 0.134 mol) in methylene chloride (100 ml), and the mixture was stirred at room temperature. 3,4-Dihydro-2H-pyran (16.86 g, 0.200 mol) was added thereto. The mixture was stirred at room temperature for 2 hours, and saturated aqueous sodium bicarbonate solution (200 ml) was added. The resulting mixture was extracted with methylene chloride and dried over anhydrous magnesium sulfate. Evaporation of the solvent gave the desired compound 1-bromo-2-(tetrahydropyran-2-yloxymethyl)benzene (36.00 g, 99.3%) as an oil.

NMR ($\delta$ ppm, TMS/CDCl$_3$): 1.45–1.80(6H,m), 3.45–3.55 (1H,m), 3.80–3.90(1H,m), 4.52(1H,d,J=15.0), 4.80(1H,m), 4.90 (1H,d,J=15.0), 7.16(1H,t,J=7.3), 7.31(1H,t,J=7.3), 7.51 (1H,d,J=7.3), 7.54(1H,d,J=7.3).

Reference Example 2

Synthesis of ethyl 2-oxo-2-(2-(tetrahydropyran-2-yloxymethyl)phenyl]acetate

Magnesium (2.67 g, 0.110 mol) and bromoethane (0.20 ml) were added to a solution of 1-bromo-2-(tetrahydropyran-2-yloxymethyl)benzene (27.11 g, 0.100 mol) in tetrahydrofuran (50 ml) under an atmosphere of nitrogen, and the mixture was stirred at room temperature for 1 hour to prepare a Grignard reagent. The Grignard reagent was added dropwise to a solution of diethyl oxalate (29.23 g, 0.200 mol) in tetrahydrofuran (100 ml) cooled to −78° C. After stirring for 1 hour at −78° C., water (150 ml) was added. The mixture was extracted with ether, dried over anhydrous magnesium sulfate. The solvent was evaporated, and the residue was purified by column chromatography on silica gel (n-hexane/ethyl acetate=4/1) to give the desired compound ethyl 2-oxo-2-[2-(tetrahydropyran-2-yloxymethyl)phenyl]acetate (22.60 g, 77.3%) as an oil.

NMR ($\delta$ ppm, TMS/CDCl$_3$): 1.38(3H,t,J=7.0), 1.40–1.85 (6H,m), 3.50–3.60(1H,m), 3.80–3.90(1H,m), 4.32–4.40(2H, m), 4.69(1H,m), 4.85(1H,d,J=14.6), 5.09(1H,d,J=14.6), 7.43 (1H,t,J=7.3), 7.58–7.70(3H,m).

Reference Example 3

Synthesis of 2-oxo-N-methyl-2-[2-(tetrahydropyran-2-yloxymethyl)phenyl]acetamide 40% monomethylamine-methanol (2.65 g, 34.1 mmol) solution was added to a solution of ethyl 2-oxo-2-[2-(tetrahydropyran-2-yloxymethyl)phenyl]acetate (2.00 g, 6.8 mmol) in methanol (20 ml), and the mixture was stirred at room temperature for 2 hours. The solvent was evaporated, and the residue was purified by column chromatography on silica gel (n-hexane/ethyl acetate=4/1) to give the desired compound 2-oxo-N-methyl-2-[2-(tetrahydropyran-2-yloxymethyl)phenyl]acetamide (1.30 g, 69%) as an oil.

NMR (δ ppm, TMS/CDCl$_3$): 1.56–1.80(6H,m), 2.96 (3H, d,J=5.5), 3.40–3.50(1H,m), 3.75–3.85(1H,m), 4.60(1H,m), 4.75(1H,d,J=14.0), 4.97(1H,d,J=14.0), 7.04(1H,brs), 7.35–7.39(1H,m), 7.51(2H,m), 7.79(1H,d,J=7.9).

The following pot experiments illustrate the controlling effects of foliage application of the various compounds of the present invention on various plant diseases.

Experimental Method

All the tests assessed controlling effects. That is, the tests were carried out by spraying a liquid sample to a test plant and inoculating the plant with a pathogen 24 hours thereafter. A test compound was dissolved in a small amount of N,N-dimethylformamide, and the solution was diluted to 500 ppm with distilled water containing a spreader to prepare a liquid sample. The percent control was calculated according to the following equation:

Percent control (%)=((severity, number of lesions, etc. in untreated plot–severity, number of lesions, etc. in treated plot)/severity, number of lesions, etc. in untreated plot}×100

Test Example 1

Controlling effect on *Pyricularia orvzae*

Two-week rice seedlings (var.: AICHIASAHI) were transplanted in plastic cups (each 9 cm in diameter) and cultivated another 2 weeks. The test compound in the form of a solution or a suspension was sprayed to the foliage of the rice-seedlings. The inoculation of the pathogen was carried out by spraying to the foliage a conidia suspension of *Pyricularia oryzae* cultured in an oatmeal medium. After the inoculation, the test plant was kept in a moist chamber (28° C., 100% R.H.) for 24 hours and then in a greenhouse for 5 days. Six days after the inoculation, the number of lesions on the leaves of the inoculated plant was measured to calculate the percent control.

The compound showed high percent control to *Pyricularia oryzae*. For example, the following compounds showed a percent control of not less than 90% at 500 ppm: Compound Nos. 75, 139, 140, 161, 163, 165, 166, 170, 175, 176, 186, 193, 194, 196, 197, 211, 212, 214, 217, 219, 221, 223, 233, 267, 372, 423, 427, 429, 432, 448, 459, 465, 466, 467, 472, 474, 475, 476, 477, 486, 488, 491, 492, 494, 495, 499, 500, 501, 503, 513, 516, 517, 518, 526, 529, 532,535, 544, 553, 556, 559, 562,580, 609, 616, 639, 678, 680, 682, 684, 686, 688, 690, 692, 698, 701, 702, 704, 707, 710, 717, 718, 721, 722, 725, 726, 733, 736, 739, 740, 773, 781, 785, 813, 819, 824, 837, 883 and 982.

Test Example 2

Controlling Effect on Cucumber Powdery Mildew (*Sphaerotheca fuliginea*)

Seeds of cucumber (var.: TSUKUBASHIROIBO) were sown in plastic cups (each 9 cm in diameter), followed by cultivation for 2 to 3 weeks. The liquid test sample in the form of a solution or suspension was sprayed on the surface of their first leaves. The pathogen was inoculated by spraying to the leaves a conidia suspension of *Sphaerotheca fuliginea* which had been cultured on the cucumber leaves. After the inoculation, the plants were kept in a greenhouse at 20° C. Ten days after the inoculation, the infected area on the leaf was observed, and the percent control was calculated.

The compound showed high percent control to *Sphaerotheca fuliginea*. For example, the following compounds showed a percent control of not less than 97% at 500 ppm: Compound Nos. 64, 75, 78, 113, 139, 140, 141, 142, 143, 144, 145, 149, 151, 152, 155, 156, 161, 165, 170, 173, 174, 176, 179, 180, 183, 185, 186, 189, 193, 194, 195, 196, 197, 198, 205, 206, 207, 208, 209, 210, 211, 212, 213, 214, 215, 216, 217, 218, 219, 221, 223, 231, 233, 262, 263, 267, 291, 292, 296, 297, 362, 372, 417, 420, 423, 427, 429, 432, 433, 436, 437, 443, 448, 453, 454, 459, 461, 465, 466, 467, 468, 469, 472, 474, 475, 476, 477, 482, 486, 488, 489, 491, 492, 494, 497, 498, 500, 501, 503, 504, 506, 513, 515, 516, 517, 518, 520, 523, 526, 527, 529, 532, 535, 541, 542, 544, 553, 556, 559, 577, 580, 586, 587, 589, 590, 592, 593, 603, 606, 609, 616, 627, 639, 678, 680, 682, 684, 686, 688, 690, 692, 698, 701, 702, 704, 707, 710, 717, 718, 721, 722, 725, 726, 733, 734, 736, 737, 738, 739, 740, 756, 759, 773, 777, 781, 785, 813, 819, 824 and 883.

Test Example 3

Controlling Effect on *Pseudoperonospora cubensis*

The seeds of cucumber (var.: TSUKUBASHIROIBO) were sown in plastic cups (each 9 cm in diameter), followed by cultivation for 2 to 3 weeks. The test compound in the form of a solution or suspension was sprayed to the surface of their first leaves, and a zoosporangia suspension of *Pseudoperonospora cubensis* cultured on cucumber leaves was dropped on the above leaf surfaces to inoculate the test plants with the pathogen. After the inoculation, the plants were kept in a moist chamber at 20° C. for 10 days. Then, the increased diameters of the lesions around the inoculated part were measured and the percent control was calculated.

The compound showed high percent control to *Pseudoperonospora cubensis*. For example, the following compounds showed a percent control of not less than 90% at 500 ppm: Compound Nos. 74, 113, 139, 140, 156, 161, 165, 170, 176, 186, 189, 193, 194, 196, 197, 206, 207, 209, 210, 212, 216, 217, 218, 219, 221, 223, 231, 233, 263, 267, 291, 362, 372, 417, 420, 423, 427, 429, 432, 433, 443, 448, 453, 459, 465, 466, 467, 468, 472, 474, 476, 477, 478, 482, 487, 488, 489, 491, 492, 494, 495, 496, 497, 498, 499, 500, 501, 503, 504, 505, 506, 507, 508, 509, 512, 513, 515, 516, 517, 518, 523, 526, 527, 529, 535, 541, 542, 544, 553, 556, 559, 562, 576, 580, 581, 583, 586, 587, 589, 590, 606, 609, 616, 627, 639, 678, 680, 682, 684, 686, 688, 690, 692, 698, 701, 702, 704, 707, 710, 717, 718, 721, 722, 725, 726, 733, 734, 735, 736, 737, 739, 740, 756, 757, 758, 759, 773, 777, 781, 785, 813, 819, 824, 837, 883, 982, 995, 1016, 1019, 1030, 1031, 1033 and 1034.

Test Example 4

Controlling Effect on *Erysiphe graminis f.* sp. *tritici*

The seeds of wheat (var.: NORIN No. 61) were sown in plastic cups (each 9 cm in diameter), followed by cultivation for 2 to 3 weeks. The test compound in the form of a solution or suspension was sprayed to the seedlings, and conidia of *Erysiphe araminis f.* sp. *tritici* cultured on wheat leaves were dropped on the test plants to inoculate the plants with the pathogen. After the inoculation, the plants were kept in a greenhouse at 20° C. Ten days after the inoculation, the infected area on the leaf was observed, and the percent control was calculated.

The compound showed high percent control to *Erysiphe graminis f.* sp. *tritici*. For example, the following compounds showed a percent control of not less than 90% at 500 ppm: Compound Nos. 2, 75, 113, 139, 140, 141, 142, 143, 144, 145, 151, 152, 161, 170, 174, 175, 176, 179, 184, 185, 186, 188, 189, 193, 194, 195, 196, 197, 198, 206, 212, 216, 217, 218, 219, 223, 263, 297, 362, 372, 417, 420, 423, 427, 429, 432, 433, 443, 448, 454, 459, 465, 466, 467, 474, 477, 488, 492, 498, 500, 517, 518, 526, 527, 541, 542, 590, 603, 627, 686, 701, 726, 739 and 883.

As described above, the present invention provides a novel α-substituted phenylacetic acid derivative having fungicidal-activity, a process for producing it, intermediates for the process, and an agricultural fungicide containing it as an active ingredient.

What is claimed is:

1. A compound of the formula (I):

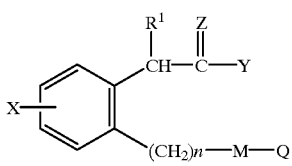

(I)

wherein $R^1$ is a halogen atom, optionally substituted alkyl, hydroxyl, optionally substituted alkoxy, alkylthio, alkylsulfinyl, alkylsulfonyl, optionally substituted amino or nitro; Q is an optionally substituted pyridyl; Y is hydroxyl, optionally substituted alkoxy, alkylthio or optionally substituted amino, provided that, when $R^1$ is hydroxyl, Y is not alkoxy; Z is an oxygen atom or sulfur atom; M is an oxygen atom, $S(O)_i$ (in which i is 0, 1 or 2), $NR^2$ (in which $R^2$ is a hydrogen atom, alkyl or acyl) or a single bond; and n is 0, 1 or 2; or a salt thereof.

2. A compound according to claim 1, wherein $R^1$ is a halogen atom, alkyl, haloalkyl, alkoxyalkyl, hydroxyl, alkoxy, alkenyloxy, alkynyloxy, haloalkoxy, haloalkenyloxy, haloalkynyloxy, alkoxyalkoxy, alkylcarbonyloxy, (alkylthio)carbonyloxy, alkylsulfonyloxy, arylsulfonyloxy, mono- or di-alkyl-substituted carbamoyloxy, aryloxy, alkylthio, alkylsulfinyl, alkylsulfonyl, amino optionally substituted by alkyl, nitro or tetrahydropyranyloxy, or a salt thereof.

3. A compound according to claim 1, wherein $R^1$ is alkoxy, or a salt thereof.

4. A compound according to claim 1, wherein $R^1$ is methoxy, or a salt thereof.

5. A compound according to claim 1, wherein Q is optionally substituted pyridyl, or a salt thereof.

6. A compound according to claim 1, wherein X is a hydrogen atom, or a salt thereof.

7. A compound according to claim 1, wherein Y is alkoxy, or a salt thereof.

8. A compound according to claim 1, wherein Y is methoxy, or a salt thereof.

9. A compound according to claim 1, wherein Y is monoalkylamino, or a salt thereof.

10. A compound according to claim 1, wherein Y is monomethylamino, or a salt thereof.

11. A compound according to claim 1, wherein Z is an oxygen atom, or a salt thereof.

12. A compound according to claim 1, wherein M is an oxygen atom, sulfur atom or $NR^2$, or a salt thereof.

13. A compound according to claim 1, wherein n is 0, or a salt thereof.

14. A compound according to claim 1, wherein n is 1, or a salt thereof.

15. A compound according to claim 1, wherein X is a hydrogen atom, $R^1$ is hydroxy, Z is an oxygen atom, Y is amino optionally substituted with alkyl, M is an oxygen atom, Q is an optionally substituted pyridyl group, and n is 0 or 1, or a salt thereof.

16. A compound according to claim 1, wherein X is a hydrogen atom, $R^1$ is alkoxy, Z is an oxygen atom, Y is alkoxy or optionally substituted amino, M is an oxygen atom, Q is an optionally substituted pyridyl group, and n is 0 or 1, or a salt thereof.

17. A compound according to claim 1, wherein:

X is a hydrogen atom, $R^1$ is methoxy, Z is an oxygen atom, Y is monomethylamino, M is an oxygen atom, Q is 3-chloro-5-trifluoromethylpyridin-2-yl, and n is 1;

X is a hydrogen atom, $R^1$ is methoxy, Z is an oxygen atom, Y is monomethylamino, M is an oxygen atom, Q is 3,5-dichloropyridin-2-yl, and n is 1;

X is a hydrogen atom, $R^1$ is methoxy, Z is an oxygen atom, Y is monomethylamino, M is an oxygen atom, Q is 3-trifluoromethyl-5-chloropyridin-2-yl, and n is 1;

X is a hydrogen atom, $R^1$ is methoxy, Z is an oxygen atom, Y is monomethylamino, M is an oxygen atom, Q is 3-chloropyridin-2-yl, and n is 1; or a salt thereof.

18. An agricultural fungicidal composition comprising a compound according to claim 1 as an active ingredient.

19. A method for controlling phytopathogenic fungi which comprises applying a fungicidally effective amount of a compound according to claim 1 or a salt thereof as an active ingredient to a locus where phytopathogenic fungi propagate or will propagate.

20. An agricultural fungicidal composition comprising a fungicidally effective amount of the compound according to claim 1 and an agriculturally acceptable carrier.

* * * * *